United States Patent
Brownhill et al.

(10) Patent No.: US 11,839,464 B2
(45) Date of Patent: Dec. 12, 2023

(54) NEUROSTIMULATION AND MONITORING USING SENSOR ENABLED WOUND MONITORING AND THERAPY APPARATUS

(71) Applicant: Smith & Nephew PLC, Watford (GB)

(72) Inventors: Varuni Rachindra Brownhill, Swanland (GB); Victoria Jody Hammond, Hull (GB); Allan Kenneth Frazer Grugeon Hunt, Beverley (GB); Charlotte Urwin, Hull (GB)

(73) Assignee: Smith & Nephew, PLC, Watford (GB)

( * ) Notice: Subject to any disclaimer, the term of this patent is extended or adjusted under 35 U.S.C. 154(b) by 899 days.

(21) Appl. No.: 16/651,119

(22) PCT Filed: Sep. 24, 2018

(86) PCT No.: PCT/EP2018/075819
§ 371 (c)(1),
(2) Date: Mar. 26, 2020

(87) PCT Pub. No.: WO2019/072531
PCT Pub. Date: Apr. 18, 2019

(65) Prior Publication Data
US 2020/0297244 A1    Sep. 24, 2020

Related U.S. Application Data

(60) Provisional application No. 62/564,467, filed on Sep. 28, 2017.

(51) Int. Cl.
*A61N 5/10* (2006.01)
*A61B 5/11* (2006.01)
(Continued)

(52) U.S. Cl.
CPC .......... *A61B 5/1109* (2013.01); *A61B 5/1032* (2013.01); *A61B 5/1104* (2013.01);
(Continued)

(58) Field of Classification Search
CPC . A61F 13/00051; A61F 13/02; A61N 1/0456; A61N 1/0468; A61N 1/0476;
(Continued)

(56) References Cited

U.S. PATENT DOCUMENTS

| | | |
|---|---|---|
| 3,896,802 A | 7/1975 | Williams |
| 4,334,530 A | 6/1982 | Hassell |

(Continued)

FOREIGN PATENT DOCUMENTS

| | | |
|---|---|---|
| CN | 105232229 A | 1/2016 |
| CN | 105395184 A | 3/2016 |

(Continued)

OTHER PUBLICATIONS

Mehmood N., et al., "Applications Of Modern Sensors And Wireless Technology In Effective Wound Management: Modern Sensors And Wireless Technology," Journal of Biomedical Materials Research Part B, vol. 102, May 1, 2014, XP055739544, pp. 885-895.
(Continued)

*Primary Examiner* — Amanda K Hulbert
(74) *Attorney, Agent, or Firm* — Knobbe, Martens, Olson & Bear, LLP

(57) ABSTRACT

An apparatus for monitoring neural response and/or providing treatment includes an electrical stimulator configured to apply electrical stimulation, and one or more processors configured to analyze stimulation response. The one or more processors can be further configured to operate the electrical stimulator, adjust the electrical stimulation, and determine one or more wound characteristics based at least in part on at least one of the electrical stimulation or the stimulation response, e.g. a movement of a patient, a color absorption characteristic, or other physiological responses. An indication of the one or more wound characteristics can be provided.

21 Claims, 20 Drawing Sheets

(51) Int. Cl.
  *A61B 5/103*  (2006.01)
  *A61B 5/00*  (2006.01)
  *A61F 13/02*  (2006.01)
  *A61N 1/04*  (2006.01)
  *A61B 5/395*  (2021.01)

(52) U.S. Cl.
  CPC .............. *A61B 5/395* (2021.01); *A61B 5/445* (2013.01); *A61B 5/4836* (2013.01); *A61B 5/4842* (2013.01); *A61B 5/4848* (2013.01); *A61B 5/6802* (2013.01); *A61F 13/02* (2013.01); *A61N 1/0456* (2013.01); *A61N 1/0468* (2013.01); *A61N 1/0476* (2013.01); *A61B 2562/0219* (2013.01)

(58) Field of Classification Search
  CPC .............. A61N 1/0492; A61N 1/36014; A61B 2562/0219; A61B 5/1032; A61B 5/1104; A61B 5/1109; A61B 5/1116; A61B 5/1123; A61B 5/445; A61B 5/4836; A61B 5/4842; A61B 5/4848; A61B 5/6802; A61B 5/389
  See application file for complete search history.

(56) References Cited

U.S. PATENT DOCUMENTS

| | | |
|---|---|---|
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,077,832 B2 | 7/2006 | Fleischmann |
| 7,088,591 B2 | 8/2006 | Kishimoto et al. |
| 7,201,063 B2 | 4/2007 | Taylor |
| 7,206,623 B2 | 4/2007 | Blank et al. |
| 7,289,205 B2 | 10/2007 | Yaroslavsky et al. |
| 7,316,152 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,569,742 B2 | 8/2009 | Haggstrom et al. |
| 7,625,117 B2 | 12/2009 | Haslett et al. |
| 7,687,678 B2 | 3/2010 | Jacobs |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,238,996 B2 | 8/2012 | Burnes et al. |
| 8,241,231 B2 | 8/2012 | Bausewein et al. |
| 8,332,053 B1 | 12/2012 | Patterson et al. |
| 8,333,874 B2 | 12/2012 | Currie |
| 8,366,692 B2 | 2/2013 | Weston et al. |
| 8,480,641 B2 | 7/2013 | Jacobs |
| 8,579,872 B2 | 11/2013 | Coulthard et al. |
| 8,644,911 B1 | 2/2014 | Panasyuk et al. |
| 8,663,106 B2 | 3/2014 | Stivoric et al. |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,220,455 B2 | 12/2015 | Sarrafzadeh et al. |
| 9,226,402 B2 | 12/2015 | Hsu |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Macia Barber et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,907,103 B2 | 2/2018 | Chen et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov et al. |
| 10,152,789 B2 | 12/2018 | Carnes et al. |
| 10,182,740 B2 | 1/2019 | Tonar et al. |
| 10,207,031 B2 | 2/2019 | Toth |
| 10,209,213 B2 | 2/2019 | Kang et al. |
| 10,285,620 B2 | 5/2019 | Jung et al. |
| 10,321,862 B2 | 6/2019 | Dalene et al. |
| 10,463,773 B2 | 11/2019 | Haggstrom et al. |
| 10,857,038 B2 | 12/2020 | Zamierowski et al. |
| 11,013,910 B2 | 5/2021 | Lawson et al. |
| 11,026,847 B2 * | 6/2021 | Piotrowski ........ A61F 13/00068 |
| 11,229,553 B2 | 1/2022 | Chen et al. |
| 11,647,922 B2 | 5/2023 | Scherer |
| 2002/0016536 A1 | 2/2002 | Benni |
| 2002/0135752 A1 | 9/2002 | Sokolov et al. |
| 2003/0033032 A1 | 2/2003 | Lind et al. |
| 2003/0208148 A1 | 11/2003 | Sullivan |
| 2003/0210810 A1 | 11/2003 | Gee, Jr. et al. |
| 2003/0216630 A1 | 11/2003 | Jersey-Willuhn et al. |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2006/0052678 A1 | 3/2006 | Drinan et al. |
| 2006/0058690 A1 | 3/2006 | Bartnik et al. |
| 2006/0181791 A1 | 8/2006 | Van Beek et al. |

(56) References Cited

U.S. PATENT DOCUMENTS

| | | |
|---|---|---|
| 2006/0234383 A1 | 10/2006 | Gough |
| 2006/0241495 A1 | 10/2006 | Kurtz |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner, Jr. et al. |
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0130697 A1* | 6/2011 | Nagle .................. A61N 1/0492 602/53 |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | Mckenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0112347 A1 | 5/2012 | Eckhardt et al. |
| 2012/0165717 A1 | 6/2012 | Al Khaburi |
| 2012/0190956 A1 | 7/2012 | Connolly |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274563 A1 | 10/2013 | Duesterhoft et al. |
| 2013/0274629 A1 | 10/2013 | Duesterhoft et al. |
| 2013/0317367 A1 | 11/2013 | Shuler |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh et al. |
| 2016/0022223 A1 | 1/2016 | Grundfest et al. |
| 2016/0029900 A1 | 2/2016 | Laplante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandani et al. |
| 2016/0081580 A1* | 3/2016 | Bergelin ................ A61B 5/445 600/554 |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0165719 A1 | 6/2016 | Li et al. |
| 2016/0166438 A1 | 6/2016 | Rovaniemi |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0086519 A1 | 3/2017 | Vigano' et al. |
| 2017/0086709 A1 | 3/2017 | Khine et al. |
| 2017/0095208 A1 | 4/2017 | Oberleitner et al. |
| 2017/0146474 A1 | 5/2017 | Bedell et al. |
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |
| 2017/0164876 A1 | 6/2017 | Hyde et al. |

(56) References Cited

U.S. PATENT DOCUMENTS

| | | |
|---|---|---|
| 2017/0172439 A1 | 6/2017 | Zhu et al. |
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0008177 A1 | 1/2018 | Shimuta et al. |
| 2018/0055359 A1 | 3/2018 | Shamim et al. |
| 2018/0055697 A1 | 3/2018 | Mihali et al. |
| 2018/0056087 A1 | 3/2018 | Ribeiro et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2019/0021911 A1 | 1/2019 | Askem et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0290496 A1 | 9/2019 | Brownhill et al. |
| 2019/0374387 A1 | 12/2019 | Ribble et al. |
| 2020/0054218 A1 | 2/2020 | Xi |
| 2020/0078482 A1 | 3/2020 | Yoon et al. |
| 2020/0078499 A1 | 3/2020 | Gadde et al. |
| 2020/0147407 A1 | 5/2020 | Efremkin |
| 2020/0330258 A1 | 10/2020 | Hansen et al. |
| 2021/0212855 A1 | 7/2021 | Hansen et al. |

FOREIGN PATENT DOCUMENTS

| | | |
|---|---|---|
| CN | 106102322 A | 11/2016 |
| DE | 102012211015 A1 | 1/2014 |
| DE | 102013013013 A1 | 2/2015 |
| EP | 2274047 A1 | 1/2011 |
| EP | 2454990 A2 | 5/2012 |
| EP | 2565630 A1 | 3/2013 |
| EP | 3231478 A1 | 10/2017 |
| EP | 3409190 A1 | 12/2018 |
| EP | 3499510 A1 | 6/2019 |
| EP | 3837520 A1 | 6/2021 |
| GB | 1476894 A | 6/1977 |
| GB | 2316171 A | 2/1998 |
| GB | 2563602 A | 12/2018 |
| JP | 2009225863 A | 10/2009 |
| KR | 20120119523 A | 10/2012 |
| KR | 101224629 B1 | 1/2013 |
| KR | 20140024743 A | 3/2014 |
| KR | 20140058041 A | 5/2014 |
| KR | 20160071044 A | 6/2016 |
| KR | 20190105898 A | 9/2019 |
| NL | 1027236 C2 | 4/2006 |
| WO | WO-0021433 A1 | 4/2000 |
| WO | WO-0043046 A2 | 7/2000 |
| WO | WO-03067229 A1 | 8/2003 |
| WO | WO-2006041997 A2 | 4/2006 |
| WO | WO-2007030379 A2 | 3/2007 |
| WO | WO-2008006150 A1 | 1/2008 |
| WO | WO-2008010604 A1 | 1/2008 |
| WO | WO-2009052607 A1 | 4/2009 |
| WO | WO-2009120951 A2 | 10/2009 |
| WO | WO-2009141777 A1 | 11/2009 |
| WO | WO-2010020919 A1 | 2/2010 |
| WO | WO-2010105053 A2 | 9/2010 |
| WO | WO-2011082420 A1 | 7/2011 |
| WO | WO-2011113070 A1 | 9/2011 |
| WO | WO-2011123848 A1 | 10/2011 |
| WO | WO-2012141999 A1 | 10/2012 |
| WO | WO-2013026999 A1 | 2/2013 |
| WO | WO-2013044226 A2 | 3/2013 |
| WO | WO-2013155193 A1 | 10/2013 |
| WO | WO-2014036577 A1 | 3/2014 |
| WO | WO-2014116816 A1 | 7/2014 |
| WO | WO-2015112095 A1 | 7/2015 |
| WO | WO-2015168720 A1 | 11/2015 |
| WO | WO-2016025438 A1 | 2/2016 |
| WO | WO-2016030752 A1 | 3/2016 |
| WO | WO-2016058032 A1 | 4/2016 |
| WO | WO-2016073777 A1 | 5/2016 |
| WO | WO-2016100218 A1 | 6/2016 |
| WO | WO-2016109744 A1 | 7/2016 |
| WO | WO-2016110564 A1 | 7/2016 |
| WO | WO-2016187136 A1 | 11/2016 |
| WO | WO-2016205872 A1 | 12/2016 |
| WO | WO-2016205881 A1 | 12/2016 |
| WO | WO-2017021006 A1 | 2/2017 |
| WO | WO-2017021965 A2 | 2/2017 |
| WO | WO-2017033058 A1 | 3/2017 |
| WO | WO-2017037479 A1 | 3/2017 |
| WO | WO-2017041014 A1 | 3/2017 |
| WO | WO-2017041385 A1 | 3/2017 |
| WO | WO-2017041386 A1 | 3/2017 |
| WO | WO-2017041387 A1 | 3/2017 |
| WO | WO-2017119996 A1 | 7/2017 |
| WO | WO-2017205728 A1 | 11/2017 |
| WO | WO-2017214188 A1 | 12/2017 |
| WO | WO-2018035612 A1 | 3/2018 |
| WO | WO-2018060417 A1 | 4/2018 |
| WO | WO-2018064569 A1 | 4/2018 |
| WO | WO-2018115461 A1 | 6/2018 |
| WO | WO-2018144938 A1 | 8/2018 |
| WO | WO-2018144941 A1 | 8/2018 |
| WO | WO-2018144943 A1 | 8/2018 |
| WO | WO-2018144946 A1 | 8/2018 |
| WO | WO-2018162728 A2 | 9/2018 |
| WO | WO-2018162732 A1 | 9/2018 |
| WO | WO-2018162735 A1 | 9/2018 |
| WO | WO-2018162736 A1 | 9/2018 |
| WO | WO-2018185138 A1 | 10/2018 |
| WO | WO-2018189265 A1 | 10/2018 |
| WO | WO-2018209090 A1 | 11/2018 |
| WO | WO-2018210692 A1 | 11/2018 |
| WO | WO-2018211458 A1 | 11/2018 |
| WO | WO-2018234443 A1 | 12/2018 |
| WO | WO-2019020550 A2 | 1/2019 |
| WO | WO-2019020551 A1 | 1/2019 |
| WO | WO-2019020666 A1 | 1/2019 |
| WO | WO-2019030384 A2 | 2/2019 |
| WO | WO-2019048624 A1 | 3/2019 |
| WO | WO-2019048626 A1 | 3/2019 |
| WO | WO-2019048638 A1 | 3/2019 |
| WO | WO-2019063481 A1 | 4/2019 |
| WO | WO-2019063488 A2 | 4/2019 |
| WO | WO-2019067264 A1 | 4/2019 |
| WO | WO-2019072531 A1 | 4/2019 |
| WO | WO-2019076967 A2 | 4/2019 |
| WO | WO-2019096828 A1 | 5/2019 |
| WO | WO-2019140441 A2 | 7/2019 |
| WO | WO-2019140444 A1 | 7/2019 |
| WO | WO-2019140448 A1 | 7/2019 |
| WO | WO-2019140449 A1 | 7/2019 |
| WO | WO-2019193141 A1 | 10/2019 |
| WO | WO-2019216883 A1 | 11/2019 |
| WO | WO-2019230183 A1 | 12/2019 |
| WO | WO-2019238180 A1 | 12/2019 |
| WO | WO-2019238181 A1 | 12/2019 |
| WO | WO-2019238182 A1 | 12/2019 |
| WO | WO-2019238195 A1 | 12/2019 |
| WO | WO-2019238196 A1 | 12/2019 |
| WO | WO-2019238197 A1 | 12/2019 |

(56) References Cited

FOREIGN PATENT DOCUMENTS

WO   WO-2019238198 A1   12/2019
WO   WO-2020043806 A1   3/2020

OTHER PUBLICATIONS

Aubakir B., et al., "Vital Sign Monitoring Utilizing Eulerian Video Magnification and Thermography," 38th Annual International Conference of the IEEE Engineering in Medicine and Biology Society, Aug. 16, 2016, pp. 3527-3530 (4 pages).

Cauwe M., et al., "Technology Development for a Low-Cost, Roll-to-Roll Chip Embedding Solution Based on PET Foils," 18th European Microelectronics and Packaging Conference (EMPC), IEEE, Sep. 12, 2011, 6 pages.

Farooqui M.F., et al., "Low Cost Inkjet Printed Smart Bandage for Wireless Monitoring of Chronic Wounds," Scientific Reports, vol. 6, Jun. 29, 2016, 14 pages.

Geng Y., et al., "A Hybrid Low Power Biopatch for Body Surface Potential Measurement," IEEE Journal of Biomedical and Health Informatics, vol. 17 (3), May 1, 2013, pp. 591-599.

Iannetta Jr. R.A., et al., "Successful Case Histories of Polymer Based Circuitry on Flexible Film Substrates," Electro/94 International Conference Proceedings Combined Volumes, IEEE, XP010149465, May 10-12, 1994, pp. 885-889.

International Preliminary Report on Patentability for Application No. PCT/EP2018/075819, dated Apr. 9, 2020, 12 pages.

International Search Report and Written Opinion for Application No. PCT/EP2018/075819, dated Feb. 5, 2019, 17 pages.

Jinto G., et al., "Reliability of Plastic-Encapsulated Electronic Components in Supersaturated Steam Environments," IEEE Transactions on Components, Packaging and Manufacturing Technology, vol. 5 (10), Oct. 2015, pp. 1423-1431.

Little Miss Plasters, kidstravelclub.co.uk., retrieved from http://www.kidstravelclub.co.uk/little-miss-girls-childrens-plasters on Aug. 26, 2016, 2 pages.

Lu B., et al., "A Study of the Autofluorescence of Parylene Materials for µTAS Applications," Lab on Chip, vol. 10 (14), Jul. 2010, pp. 1826-1834.

McLeod A.J., et al., "Motion Magnification for Endoscopic Surgery," Progress in Biomedical Optics and Imaging, SPIE—International Society for Optical Engineering, Mar. 12, 2014, vol. 9036, 8 pages.

Mostafalu P., et al., "Wireless Flexible Smart Bandage for Continuous Monitoring of Wound Oxygenation," IEEE Transactions on Biomedical Circuits and Systems, vol. 9 (5), Oct. 2015, pp. 670-677 (8 pages).

Narusawa H., "The Corona Discharge Causes Short Destruction that had Bad Influence on a Power Switching Circuit," Adphox Corporation, Jan. 1, 2009, retrieved from http://www.adphox.co.jp/keisokuki/ke-english-corona/CORONA_DISCHARGE_EN.pdf, 12 pages.

Raviglione A., et al., "Real-Time Smart Textile-Based System to Monitor Pressure Offloading of Diabetic Foot Ulcers," Journal of Diabetes Science and Technology, vol. 11 (5), Sep. 2017, pp. 894-898.

Rose D.P., et al., "Adhesive RFID Sensor Patch for Monitoring of Sweat Electrolytes," IEEE Transactions on Biomedical Engineering, vol. 62 (6), Jun. 2015, first published on Nov. 11, 2015, pp. 1457-1465.

Wakita J., et al., "Variations in Optical Absorption and Fluorescence Spectra for Polyimide Thin Films Caused by Structural Isomerism," Journal of Photopolymer Science and Technology, Jan. 1, 2003, 1 page.

Willis B., "Conformal Coating Inspection & Coating Faults," Vision Engineering, Jul. 21, 2016, retrieved from http://www.visioneng.com/wp-content/uploads/2017/11/Conformal-Coating-Inspection-and-Defects.21JUL16.pdf, 35 pages.

Willis B., "Guide to Conformal Coating & Cleaning Defects Contents," Mar. 1, 2014, retrieved from http://coatingguide.smartgroup.org/Files%20pdf/Coating%20Defects%20V2%2014March2014.pdf, vol. 1, 31 pages.

* cited by examiner

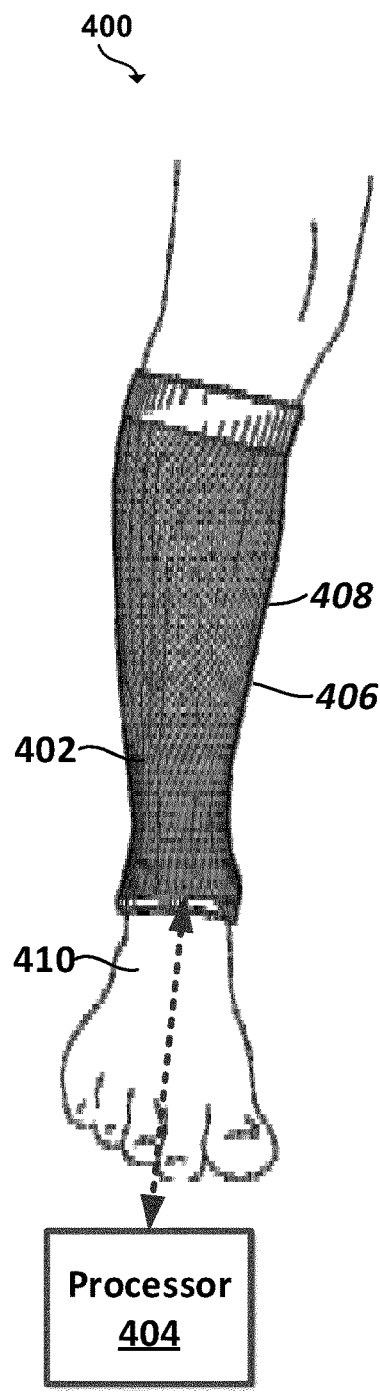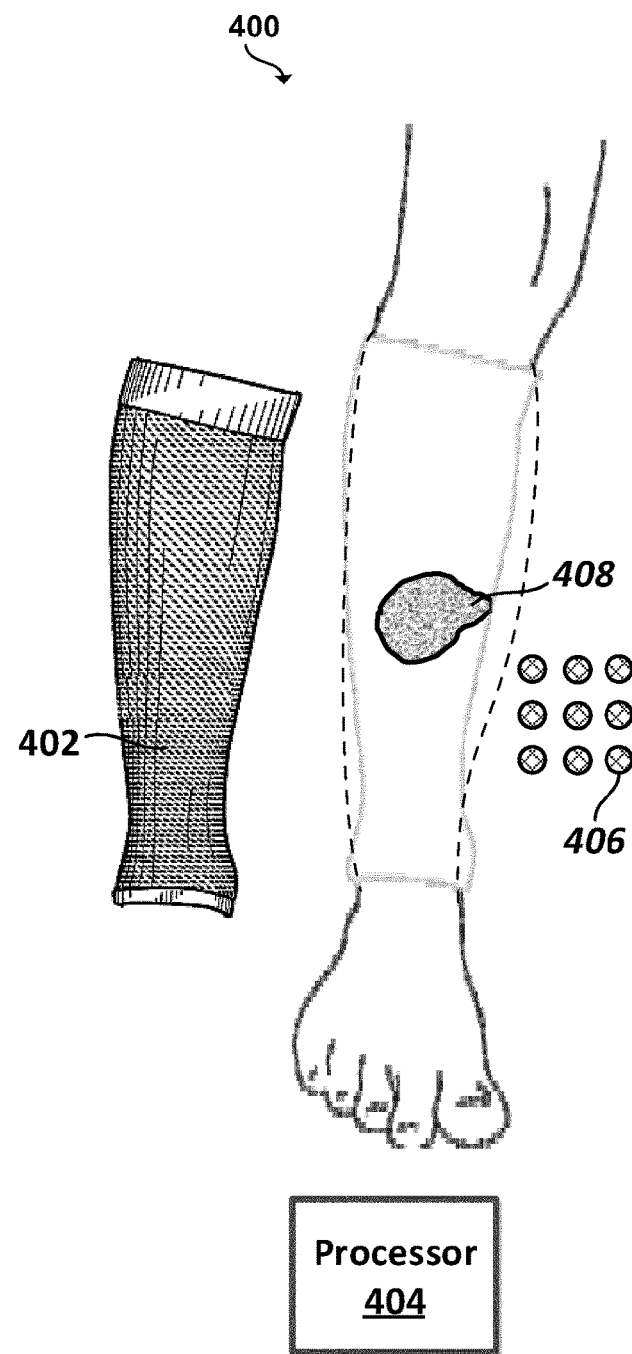
FIG. 4A  FIG. 4B

NEUROSTIMULATION AND MONITORING USING SENSOR ENABLED WOUND MONITORING AND THERAPY APPARATUS

CROSS-REFERENCE TO RELATED APPLICATIONS

This application is a U.S. national stage application of International Patent Application No. PCT/EP2018/075819, entitled "NEUROSTIMULATION AND MONITORING USING SENSOR ENABLED WOUND MONITORING AND THERAPY APPARATUS," filed Sep. 24, 2018, which claims priority to U.S. Provisional Patent Application No. 62/564,467, filed on Sep. 28, 2017, entitled "NEUROSTIMULATION AND MONITORING USING SENSOR ENABLED WOUND MONITORING AND THERAPY APPARATUS," each of which is hereby incorporated herein by reference in its entirety.

BACKGROUND

Field

Embodiments of the present disclosure relate to apparatuses, systems, and methods for the treatment of tissues via sensor-enabled monitoring in communication with various therapy regimes.

Description of the Related Art

Nearly all areas of medicine may benefit from improved information regarding the state of the tissue, organ, or system to be treated, particularly if such information is gathered in real-time during treatment. Many types of treatments are still routinely performed without the use of sensor data collection; instead, such treatments rely upon visual inspection by a caregiver or other limited means rather than quantitative sensor data. For example, in the case of wound treatment via dressings and/or negative pressure wound therapy, data collection is generally limited to visual inspection by a caregiver and often the underlying wounded tissue may be obscured by bandages or other visual impediments. Even intact, unwounded skin may have underlying damage that is not visible to the naked eye, such as a compromised vascular or deeper tissue damage that may lead to an ulcer. Similar to wound treatment, during orthopedic treatments requiring the immobilization of a limb with a cast or other encasement, only limited information is gathered on the underlying tissue. In instances of internal tissue repair, such as a bone plate, continued direct sensor-driven data collection is not performed. Further, braces and/or sleeves used to support musculoskeletal function do not monitor the functions of the underlying muscles or the movement of the limbs. Outside of direct treatments, common hospital room items such as beds and blankets could be improved by adding capability to monitor patient parameters.

Therefore, there is a need for improved sensor monitoring, particularly through the use of sensor-enabled substrates which can be incorporated into existing treatment regimes.

SUMMARY

Some embodiments of the present disclosure provide an improved wound monitoring and/or therapy apparatus. A wound monitoring and/or therapy apparatus can include an electrical stimulator configured to apply electrical stimulation to a patient, a motion detector configured to detect movement of a patient, a wound dressing configured to be positioned over and/or in contact with a wound of the patient and configured to support the electrical stimulator, and one or more processors. The one or more processors can be coupled to or in communication with the electrical stimulator and/or the motion detector. The one or more processors can be configured to operate the electrical stimulator or adjust the electrical stimulation. The operation or adjustment can be based at least in part on at least one of a stimulation response or the patient movement. The one or more processors can be configured to determine one or more wound characteristics. For example, the determination can be based at least in part on at least one of the applied electrical stimulation or the stimulation response. The one or more processors can be configured to provide an indication of the one or more wound characteristics.

The apparatus of the preceding paragraph may also include any combination of the following features described in this paragraph, among other features described herein. The electrical stimulator can be configured to detect the stimulation response. The stimulation response can include at least one of patient movement responsive to the electrical stimulation or an electrical signal that is reactive to the electrical stimulation. The motion detector can include at least one of an accelerometer, an electromyography (EMG) detector, a magnetometer, or a gyroscope. The electrical stimulator can include one or a plurality of electrodes. The plurality of electrodes can be mounted on or supported by the wound dressing, for example, as an array.

The apparatus of any of the preceding paragraphs may also include any combination of the following features described in this paragraph, among other features described herein. The one or more processors can be configured to operate each electrode in turn and can identify which electrode causes the greatest, least, or other muscle contraction. The one or more wound characteristics can be determined based at least in part on the stimulation response to the electrical stimulation from the electrode identified as causing the greatest or least muscle contraction. The one or more processors can be configured to reduce intensity of or pause the electrical stimulation responsive to the patient movement satisfying one or more movement thresholds. The one or more processors can be configured to adjust the electrical stimulation. For example, the adjustment can be based on a determination that the stimulation response does not satisfy a stimulation response threshold. The one or more processors can be further configured to determine one or more areas of neuropathy or nerve growth in the wound. For example, the determination can be based at least in part on the one or more wound characteristics. The indication of the one or more wound characteristics can include a visual map of the one or more areas of neuropathy or nerve growth.

Some embodiments provide an improved method for controlling a wound monitoring and/or therapy apparatus. The method can include applying electrical stimulation to a wound at a first stimulation level via an electrical stimulator. The electrical stimulation can be supported by a wound dressing configured to be positioned over and/or in contact with the wound. The method can further include detecting a first stimulation response to the electrical stimulation at the first stimulation level. The method can further include adjusting the electrical stimulation to a second stimulation level, applying the electrical stimulation to the wound at the second stimulation level, or detecting a second stimulation response to the electrical stimulation at the second stimulation level. The adjusting, applying, or detecting can be based at least in part on a determination that the stimulation response does not satisfy a stimulation response threshold. The method can further include determining a wound status. The determining can be based at least in part on at least one of the first or second stimulation levels or the first or second stimulation responses. The method can further include providing an indication of the wound status. The method can be performed under control of a processor or a controller.

The method of any of the preceding paragraphs may also include any combination of the following steps or features described in this paragraph, among other features described herein. The method can further include monitoring a patient movement. The method can include adjusting the electrical stimulation to the second stimulation level responsive to the patient movement satisfying a movement threshold. The wound status can include an indication of nerve health. In some cases, providing the indication of the wound status can include displaying a map corresponding to the nerve health. The method can further include determining a nerve response in at least a portion of the wound. The determination of the nerve response can be based at least in part on at least one of the first or second stimulation levels or the first or second stimulation responses.

The method of any of the preceding paragraphs may also include any combination of the following steps or features described in this paragraph, among other features described herein. The electrical stimulator can include one or a plurality of electrodes. The plurality of electrodes can be mounted on or supported by the wound dressing, for example, as an array. Monitoring a patient movement can be performed using at least one of an accelerometer, an electromyography (EMG) detector, a magnetometer or a gyroscope. An electrical impulse can be provided by one or more of the plurality of electrodes. Each electrode of the plurality of electrodes can be configured to transmit a different intensity level of electrical stimulation. In some cases, adjusting the electrical stimulation comprises operating a different electrode. The method can further include identifying an electrode that caused the stimulation response to satisfy the stimulation response threshold and/or determining a progress of wound healing based on the determined stimulation response to that electrode. The method can further include determining one or more areas of neuropathy or nerve growth in the wound based at least in part on a determined nerve response. The indication of the progress of the wound healing can include a visual map of the one or more areas of neuropathy or nerve growth.

Some embodiments provide an improved monitoring and/or therapy system. The system can include a compression apparatus configured to trigger muscle activity, such as calf muscle activity. The system can include an electrical stimulator configured to be positioned on a patient. The electrical stimulator can be configured to apply electrical stimulation to the patient, and detect a response due to at least one of calf muscle activity triggered by the calf pump or the electrical stimulation. The system can further include one or more processors coupled to the electrical stimulator and the compression apparatus. The one or more processors can be configured to determine a nerve response, for example, based on the response detected due to calf muscle activity triggered by the compression apparatus and/or the electrical stimulation, and activate the compression apparatus, for example, based at least in part on a determination that the nerve response does not satisfy a response threshold.

The system of any of the preceding paragraphs may also include any combination of the following features described in this paragraph, among other features described herein. The compression apparatus can include a calf muscle pump configured to be positioned at least partly on the calf. The system can include a wound dressing configured to be positioned over and/or in contact with a wound of the patient and configured to support the electrical stimulator. The system can include a motion detector configured to detect movement of a patient. The one or more processors can be further configured to activate at least one of the compression apparatus or the electrical stimulator, for example, based at least in part on a determination that patient movement detected by the motion detector satisfies a patient movement threshold. The one or more processors can be further configured to at least one of operate the compression apparatus to adjust the calf muscle activity triggered by the compression apparatus or adjust the electrical stimulation applied by the electrical stimulator, for example, based at least in part on a determination that at least one of the nerve response does not satisfy a response threshold or patient movement detected by the motion detector satisfies a patient movement threshold.

Some embodiments provide an improved method for controlling a wound monitoring and/or therapy apparatus. The method can include triggering calf muscle activity via a calf muscle pump positioned at least partly on a calf of a patient, and applying electrical stimulation to a wound at a first stimulation level via an electrical stimulator supported by a wound dressing configured to be positioned over and/or in contact with the wound. The method can further include detecting a nerve response due to at least one of the calf muscle activity triggered by the compression apparatus or the electrical stimulation.

The method of any of the preceding paragraphs may also include any combination of the following steps or features described in this paragraph, among other features described herein. The compression apparatus can include a calf muscle pump configured to be positioned at least partly on the calf. The method can further include adjusting the electrical stimulation to a second stimulation level, applying the electrical stimulation to the wound at the second stimulation level, and/or detecting a second nerve response to the electrical stimulation at the second stimulation level. The adjusting, applying or detecting can be based at least in part on a determination that the nerve response due to the electrical stimulation does not satisfy a stimulation response threshold. The method can further include determining that the detected nerve response does not satisfy a stimulation response threshold, and activating the compression apparatus based at least in part on the determination.

Any of the features, components, or details of any of the arrangements or embodiments disclosed in this application, including without limitation any of the pump embodiments, any of the negative pressure wound therapy embodiments, any of the wound dressing embodiments, or any of the optical sensor embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which:

FIGS. 4A-4B illustrate an example wound therapy and/or treatment system;

DETAILED DESCRIPTION

Figure 1A:
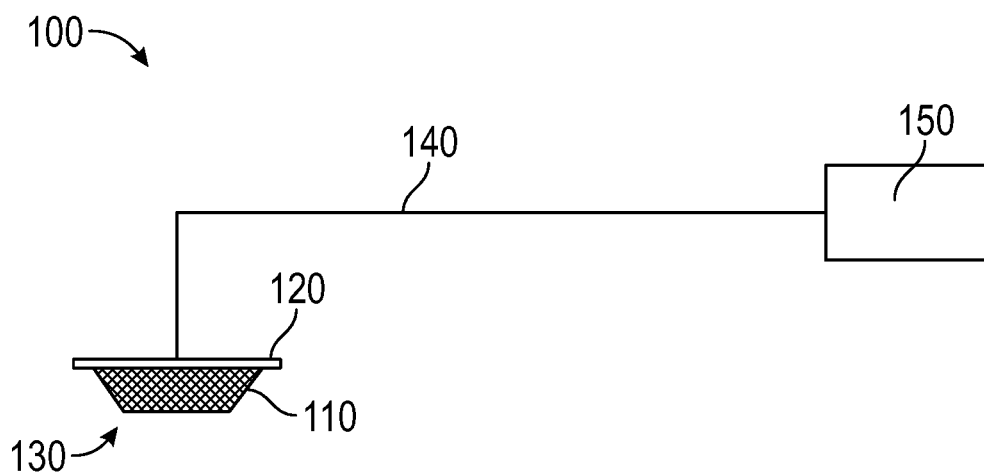
FIG. 1A illustrates a negative pressure wound treatment system according to some embodiments.

Embodiments disclosed herein relate to apparatuses and methods of monitoring and treating biological tissue with sensor-enabled substrates. The embodiments disclosed herein are not limited to treatment or monitoring of a particular type of tissue or injury, instead the sensor-enabled technologies disclosed herein are broadly applicable to any type of therapy that may benefit from sensor-enabled substrates. Some implementations utilize sensors and data collection relied upon by health care providers to make both diagnostic and patient management decisions.

Some embodiments disclosed herein relate to the use of sensors mounted on or embedded within substrates configured to be used in the treatment of both intact and damaged human or animal tissue. Such sensors may collect information about the surrounding tissue and transmit such information to a computing device or a caregiver to be utilized in further treatment. In certain embodiments, such sensors may be attached to the skin anywhere on the body, including areas for monitoring arthritis, temperature, or other areas that may be prone to problems and require monitoring. Sensors disclosed herein may also incorporate markers, such as radiopaque markers, to indicate the presence of the device, for example prior to performing an MRI or other technique.

The sensor embodiments disclosed herein may be used in combination with clothing. Non-limiting examples of clothing for use with embodiments of the sensors disclosed herein include shirts, pants, trousers, dresses, undergarments, outer-garments, gloves, shoes, hats, and other suitable garments. In certain embodiments, the sensor embodiments disclosed herein may be welded into or laminated into/onto the particular garments. The sensor embodiments may be printed directly onto the garment and/or embedded into the fabric. Breathable and printable materials such as microporous membranes may also be suitable.

Sensor embodiments disclosed herein may be incorporated into cushioning or bed padding, such as within a hospital bed, to monitor patient characteristics, such as any characteristic disclosed herein. In certain embodiments, a disposable film containing such sensors could be placed over the hospital bedding and removed/replaced as needed.

In some implementations, the sensor embodiments disclosed herein may incorporate energy harvesting, such that the sensor embodiments are self-sustaining. For example, energy may be harvested from thermal energy sources, kinetic energy sources, chemical gradients, or any suitable energy source.

The sensor embodiments disclosed herein may be utilized in rehabilitation devices and treatments, including sports medicine. For example, the sensor embodiments disclosed herein may be used in braces, sleeves, wraps, supports, and other suitable items. Similarly, the sensor embodiments disclosed herein may be incorporated into sporting equipment, such as helmets, sleeves, and/or pads. For example, such sensor embodiments may be incorporated into a protective helmet to monitor characteristics such as acceleration, which may be useful in concussion diagnosis.

The sensor embodiments disclosed herein may be used in coordination with surgical devices, for example, the NAVIO surgical system by Smith & Nephew Inc. In implementations, the sensor embodiments disclosed herein may be in communication with such surgical devices to guide placement of the surgical devices. In some implementations, the sensor embodiments disclosed herein may monitor blood flow to or away from the potential surgical site or ensure that there is no blood flow to a surgical site. Further surgical data may be collected to aid in the prevention of scarring and monitor areas away from the impacted area.

To further aid in surgical techniques, the sensors disclosed herein may be incorporated into a surgical drape to provide information regarding tissue under the drape that may not be immediately visible to the naked eye. For example, a sensor embedded flexible drape may have sensors positioned advantageously to provide improved area-focused data collection. In certain implementations, the sensor embodiments disclosed herein may be incorporated into the border or interior of a drape to create fencing to limit/control the surgical theater.

Sensor embodiments as disclosed herein may also be utilized for pre-surgical assessment. For example, such sensor embodiments may be used to collect information about a potential surgical site, such as by monitoring skin and the underlying tissues for a possible incision site. For example, perfusion levels or other suitable characteristics may be monitored at the surface of the skin and deeper in the tissue to assess whether an individual patient may be at risk for surgical complications. Sensor embodiments such as those disclosed herein may be used to evaluate the presence of microbial infection and provide an indication for the use of antimicrobials. Further, sensor embodiments disclosed herein may collect further information in deeper tissue, such as identifying pressure ulcer damage and/or the fatty tissue levels.

The sensor embodiments disclosed herein may be utilized in cardiovascular monitoring. For example, such sensor embodiments may be incorporated into a flexible cardiovascular monitor that may be placed against the skin to monitor characteristics of the cardiovascular system and communicate such information to another device and/or a caregiver. For example, such a device may monitor pulse rate, oxygenation of the blood, and/or electrical activity of the heart. Similarly, the sensor embodiments disclosed herein may be utilized for neurophysiological applications, such as monitoring electrical activity of neurons.

The sensor embodiments disclosed herein may be incorporated into implantable devices, such as implantable orthopedic implants, including flexible implants. Such sensor embodiments may be configured to collect information regarding the implant site and transmit this information to an external source. In some embodiments, an internal source may also provide power for such an implant.

The sensor embodiments disclosed herein may also be utilized for monitoring biochemical activity on the surface of the skin or below the surface of the skin, such as lactose buildup in muscle or sweat production on the surface of the skin. In some embodiments, other characteristics may be monitored, such as glucose concentration, urine concentration, tissue pressure, skin temperature, skin surface conductivity, skin surface resistivity, skin hydration, skin maceration, and/or skin ripping.

Sensor embodiments as disclosed herein may be incorporated into Ear, Nose, and Throat (ENT) applications. For example, such sensor embodiments may be utilized to monitor recovery from ENT-related surgery, such as wound monitoring within the sinus passage.

As described in greater detail below, the sensor embodiments disclosed herein may encompass sensor printing technology with encapsulation, such as encapsulation with a polymer film. Such a film may be constructed using any polymer described herein, such as polyurethane. Encapsulation of the sensor embodiments may provide waterproofing of the electronics and protection from local tissue, local fluids, and other sources of potential damage.

In certain embodiments, the sensors disclosed herein may be incorporated into an organ protection layer such as disclosed below. Such a sensor-embedded organ protection layer may both protect the organ of interest and confirm that the organ protection layer is in position and providing protection. Further, a sensor-embedded organ protection layer may be utilized to monitor the underlying organ, such as by monitoring blood flow, oxygenation, and other suitable markers of organ health. In some embodiments, a sensor-enabled organ protection layer may be used to monitor a transplanted organ, such as by monitoring the fat and muscle content of the organ. Further, sensor-enabled organ protection layers may be used to monitor an organ during and after transplant, such as during rehabilitation of the organ.

The sensor embodiments disclosed herein may be incorporated into treatments for wounds (disclosed in greater detail below) or in a variety of other applications. Non-limiting examples of additional applications for the sensor embodiments disclosed herein include: monitoring and treatment of intact skin, cardiovascular applications such as monitoring blood flow, orthopedic applications such as monitoring limb movement and bone repair, neurophysiological applications such as monitoring electrical impulses, and any other tissue, organ, system, or condition that may benefit from improved sensor-enabled monitoring.

Wound Therapy

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein) wound with or without reduced pressure, including for example a source of negative pressure and wound dressing components and apparatuses. The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein).

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some embodiments relate to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure and/or traditional advanced wound care, which is not aided by the using of applied negative pressure (may also be referred to as non-negative pressure therapy).

Advanced wound care may include use of an absorbent dressing, an occlusive dressing, use of an antimicrobial and/or debriding agents in a wound dressing or adjunct, a pad (for example, a cushioning or compressive therapy, such as stockings or bandages), or the like.

In some embodiments, treatment of such wounds can be performed using traditional wound care, wherein a dressing can be applied to the wound to facilitate and promote healing of the wound.

Some embodiments relate to methods of manufacturing a wound dressing comprising providing a wound dressing as disclosed herein.

The wound dressings that may be utilized in conjunction with the disclosed technology include any known dressing in the art. The technology is applicable to negative pressure therapy treatment as well as non-negative pressure therapy treatment.

In some embodiments, a wound dressing comprises one or more absorbent layer(s). The absorbent layer may be a foam or a superabsorbent.

In some embodiments, wound dressings may comprise a dressing layer including a polysaccharide or modified polysaccharide, a polyvinylpyrrolidone, a polyvinyl alcohol, a polyvinyl ether, a polyurethane, a polyacrylate, a polyacrylamide, collagen, or gelatin or mixtures thereof. Dressing layers comprising the polymers listed are known in the art as being useful for forming a wound dressing layer for either negative pressure therapy or non-negative pressure therapy.

In some embodiments, the polymer matrix may be a polysaccharide or modified polysaccharide.

In some embodiments, the polymer matrix may be a cellulose. Cellulose material may include hydrophilically modified cellulose such as methyl cellulose, carboxymethyl cellulose (CMC), carboxymethyl cellulose (CEC), ethyl cellulose, propyl cellulose, hydroxyethyl cellulose, hydroxypropyl cellulose, hydroxypropylmethyl cellulose, carboxyethyl sulphonate cellulose, cellulose alkyl sulphonate, or mixtures thereof.

In certain embodiments, cellulose material may be cellulose alkyl sulphonate. The alkyl moiety of the alkyl sulphonate substituent group may have an alkyl group having 1 to 6 carbon atoms, such as methyl, ethyl, propyl, or butyl. The alkyl moiety may be branched or unbranched, and hence suitable propyl sulphonate substituents may be 1- or 2-methyl-ethylsulphonate. Butyl sulphonate substituents may be 2-ethyl-ethylsulphonate, 2,2-dimethyl-ethylsulphonate, or 1,2-dimethyl-ethylsulphonate. The alkyl sulphonate substituent group may be ethyl sulphonate. The cellulose alkyl sulphonate is described in WO10061225, US2016/114074, US2006/0142560, or U.S. Pat. No. 5,703,225, the disclosures of which are hereby incorporated by reference in their entirety.

Cellulose alkyl sulfonates may have varying degrees of substitution, the chain length of the cellulose backbone structure, and the structure of the alkyl sulfonate substituent. Solubility and absorbency are largely dependent on the degree of substitution: as the degree of substitution is increased, the cellulose alkyl sulfonate becomes increasingly soluble. It follows that, as solubility increases, absorbency increases.

In some embodiments, a wound dressing also comprises a top or cover layer.

The thickness of the wound dressing disclosed herein may be between 1 to 20, or 2 to 10, or 3 to 7 mm.

In some embodiments, the disclosed technology may be used in conjunction with a non-negative pressure dressing. A non-negative pressure wound dressing suitable for providing protection at a wound site may comprise:
  an absorbent layer for absorbing wound exudate and
  an obscuring element for at least partially obscuring a view of wound exudate absorbed by the absorbent layer in use.

The obscuring element may be partially translucent.

The obscuring element may be a masking layer.

The non-negative pressure wound dressing may further comprise a region in or adjacent the obscuring element for allowing viewing of the absorbent layer. For example, the obscuring element layer may be provided over a central region of the absorbent layer and not over a border region of the absorbent layer. In some embodiments, the obscuring element is of hydrophilic material or is coated with a hydrophilic material.

The obscuring element may comprise a three-dimensional knitted spacer fabric. The spacer fabric is known in the art and may include a knitted spacer fabric layer.

The obscuring element may further comprise an indicator for indicating the need to change the dressing.

In some embodiments, the obscuring element is provided as a layer at least partially over the absorbent layer, further from a wound site than the absorbent layer in use.

The non-negative pressure wound dressing may further comprise a plurality of openings in the obscuring element for allowing fluid to move therethrough. The obscuring element may comprise, or may be coated with, a material having size-exclusion properties for selectively permitting or preventing passage of molecules of a predetermined size or weight.

The obscuring element may be configured to at least partially mask light radiation having wavelength of 600 nm and less.

The obscuring element may be configured to reduce light absorption by 50% or more.

The obscuring element may be configured to yield a CIE L* value of 50 or more, and optionally 70 or more. In some embodiments, the obscuring element may be configured to yield a CIE L* value of 70 or more.

In some embodiments, the non-negative pressure wound dressing may further comprise at least one of a wound contact layer, a foam layer, an odor control element, a pressure-resistant layer and a cover layer.

In some embodiments, the cover layer is present, and the cover layer is a translucent film. Typically, the translucent film has a moisture vapor permeability of 500 g/m2/24 hours or more.

The translucent film may be a bacterial bather.

In some embodiments, the non-negative pressure wound dressing as disclosed herein comprises the wound contact layer and the absorbent layer overlies the wound contact layer. The wound contact layer carries an adhesive portion for forming a substantially fluid tight seal over the wound site.

The non-negative pressure wound dressing as disclosed herein may comprise the obscuring element and the absorbent layer being provided as a single layer.

In some embodiments, the non-negative pressure wound dressing disclosed herein comprises the foam layer, and the obscuring element is of a material comprising components that may be displaced or broken by movement of the obscuring element.

In some embodiments, the non-negative pressure wound dressing comprises an odor control element, and in another embodiment the dressing does not include an odor control element. When present, the odor control element may be dispersed within or adjacent the absorbent layer or the obscuring element. Alternatively, when present the odor control element may be provided as a layer sandwiched between the foam layer and the absorbent layer.

In some embodiments, the disclosed technology for a non-negative pressure wound dressing comprises a method of manufacturing a wound dressing, comprising: providing an absorbent layer for absorbing wound exudate; and providing an obscuring element for at least partially obscuring a view of wound exudate absorbed by the absorbent layer in use.

In some embodiments, the non-negative pressure wound dressing is may be suitable for providing protection at a wound site, comprising: an absorbent layer for absorbing wound exudate; and a shielding layer provided over the absorbent layer, and further from a wound-facing side of the wound dressing than the absorbent layer. The shielding layer may be provided directly over the absorbent layer. In some embodiments, the shielding layer comprises a three-dimensional spacer fabric layer.

The shielding layer increases the area over which a pressure applied to the dressing is transferred by 25% or more or the initial area of application. For example the shielding layer increases the area over which a pressure applied to the dressing is transferred by 50% or more, and optionally by 100% or more, and optionally by 200% or more.

The shielding layer may comprise 2 or more sub-layers, wherein a first sub-layer comprises through holes and a further sub-layer comprises through holes and the through holes of the first sub-layer are offset from the through holes of the further sub-layer.

The non-negative pressure wound dressing as disclosed herein may further comprise a permeable cover layer for allowing the transmission of gas and vapor therethrough, the cover layer provided over the shielding layer, wherein through holes of the cover layer are offset from through holes of the shielding layer.

The non-negative pressure wound dressing may be suitable for treatment of pressure ulcers.

A more detailed description of the non-negative pressure dressing disclosed hereinabove is provided in WO2013007973, the entirety of which is hereby incorporated by reference.

In some embodiments, the non-negative pressure wound dressing may be a multi-layered wound dressing comprising: a fibrous absorbent layer for absorbing exudate from a wound site; and a support layer configured to reduce shrinkage of at least a portion of the wound dressing.

In some embodiments, the multi-layered wound dressing disclosed herein, further comprises a liquid impermeable film layer, wherein the support layer is located between the absorbent layer and the film layer.

The support layer disclosed herein may comprise a net. The net may comprise a geometric structure having a plurality of substantially geometric apertures extending therethrough. The geometric structure may for example comprise a plurality of bosses substantially evenly spaced and joined by polymer strands to form the substantially geometric apertures between the polymer strands.

The net may be formed from high density polyethylene.

The apertures may have an area from 0.005 to 0.32 mm 2.

The support layer may have a tensile strength from 0.05 to 0.06 Nm.

The support layer may have a thickness of from 50 to 150 µm.

In some embodiments, the support layer is located directly adjacent the absorbent layer. Typically, the support layer is bonded to fibers in a top surface of the absorbent layer. The support layer may further comprise a bonding layer, wherein the support layer is heat laminated to the fibers in the absorbent layer via the bonding layer. The bonding layer may comprise a low melting point adhesive such as ethylene-vinyl acetate adhesive.

In some embodiments, the multi-layered wound dressing disclosed herein further comprises an adhesive layer attaching the film layer to the support layer.

In some embodiments, the multi-layered wound dressing disclosed herein further comprises a wound contact layer located adjacent the absorbent layer for positioning adjacent a wound. The multi-layered wound dressing may further comprise a fluid transport layer between the wound contact layer and the absorbent layer for transporting exudate away from a wound into the absorbent layer.

A more detailed description of the multi-layered wound dressing disclosed hereinabove is provided in GB patent application filed on 28 Oct. 2016 with application number GB1618298.2, the entirety of which is hereby incorporated by reference.

In some embodiments, the disclosed technology may be incorporated in a wound dressing comprising a vertically lapped material comprising: a first layer of an absorbing layer of material, and a second layer of material, wherein the first layer being constructed from at least one layer of non-woven textile fibers, the non-woven textile fibers being folded into a plurality of folds to form a pleated structure. In some embodiments, the wound dressing further comprises a second layer of material that is temporarily or permanently connected to the first layer of material.

Typically the vertically lapped material has been slitted.

In some embodiments, the first layer has a pleated structure having a depth determined by the depth of pleats or by the slitting width. The first layer of material may be a moldable, lightweight, fiber-based material, blend of material or composition layer.

The first layer of material may comprise one or more of manufactured fibers from synthetic, natural or inorganic polymers, natural fibers of a cellulosic, proteinaceous or mineral source.

The wound dressing may comprise two or more layers of the absorbing layer of material vertically lapped material stacked one on top of the other, wherein the two or more layers have the same or different densities or composition.

The wound dressing may in some embodiments comprise only one layer of the absorbing layer of material vertically lapped material.

The absorbing layer of material is a blend of natural or synthetic, organic or inorganic fibers, and binder fibers, or bicomponent fibers typically PET with a low melt temperature PET coating to soften at specified temperatures and to act as a bonding agent in the overall blend.

In some embodiments, the absorbing layer of material may be a blend of 5 to 95% thermoplastic polymer, and 5 to 95 wt % of a cellulose or derivative thereof.

In some embodiments, the wound dressing disclosed herein has a second layer comprises a foam or a dressing fixative.

The foam may be a polyurethane foam. The polyurethane foam may have an open or closed pore structure.

The dressing fixative may include bandages, tape, gauze, or backing layer.

In some embodiments, the wound dressing as disclosed herein comprises the absorbing layer of material connected directly to a second layer by lamination or by an adhesive, and the second layer is connected to a dressing fixative layer. The adhesive may be an acrylic adhesive, or a silicone adhesive.

In some embodiments, the wound dressing as disclosed herein further comprises layer of a superabsorbent fiber, or a viscose fiber or a polyester fiber.

In some embodiments, the wound dressing as disclosed herein further comprises a backing layer. The backing layer may be a transparent or opaque film. Typically the backing layer comprises a polyurethane film (typically a transparent polyurethane film).

A more detailed description of the multi-layered wound dressing disclosed hereinabove is provided in GB patent applications filed on 12 Dec. 2016 with application number GB1621057.7; and 22 Jun. 2017 with application number GB1709987.0, the entirety of each of which is hereby incorporated by reference.

In some embodiments, the non-negative pressure wound dressing may comprise an absorbent component for a wound dressing, the component comprising a wound contacting layer comprising gel forming fibers bound to a foam layer, wherein the foam layer is bound directly to the wound contact layer by an adhesive, polymer based melt layer, by flame lamination or by ultrasound.

The absorbent component may be in a sheet form.

The wound contacting layer may comprise a layer of woven or non-woven or knitted gel forming fibers.

The foam layer may be an open cell foam, or closed cell foam, typically an open cell foam. The foam layer is a hydrophilic foam.

The wound dressing may comprise the component that forms an island in direct contact with the wound surrounded by periphery of adhesive that adheres the dressing to the wound. The adhesive may be a silicone or acrylic adhesive, typically a silicone adhesive.

The wound dressing may be covered by a film layer on the surface of the dressing furthest from the wound.

A more detailed description of the wound dressing of this type hereinabove is provided in EP2498829, the entirety of which is hereby incorporated by reference.

In some embodiments, the non-negative pressure wound dressing may comprise a multi layered wound dressing for use on wounds producing high levels of exudate, characterized in that the dressing comprising: a transmission layer having an MVTR of at least 300 gm2/24 hours, an absorbent core comprising gel forming fibers capable of absorbing and retaining exudate, a wound contacting layer comprising gel forming fibers which transmits exudate to the absorbent core and a keying layer positioned on the absorbent core, the absorbent core and wound contacting layer limiting the lateral spread of exudate in the dressing to the region of the wound.

The wound dressing may be capable of handling at least 6 g (or 8 g and 15 g) of fluid per 10 cm2 of dressing in 24 hours.

The wound dressing may comprise gel forming fibers that are chemically modified cellulosic fibers in the form of a fabric. The fibers may include carboxymethylated cellulose fibers, typically sodium carboxymethylcellulose fiber.

The wound dressing may comprise a wound contact layer with a lateral wicking rate from 5 mm per minute to 40 mm per minute. The wound contact layer may have a fiber density between 25 gm2 and 55 gm2, such as 35 gm2.

The absorbent core may have an absorbency of exudate of at least 10 g/g, and typically a rate of lateral wicking of less the 20 mm per minute.

The absorbent core may have a blend in the range of up to 25% cellulosic fibers by weight and 75% to 100% gel forming fibers by weight.

Alternatively, the absorbent core may have a blend in the range of up to 50% cellulosic fibers by weight and 50% to 100% gel forming fibers by weight. For example the blend is in the range of 50% cellulosic fibers by weight and 50% gel forming fibers by weight.

The fiber density in the absorbent core may be between 150 gm2 and 250 gm2, or about 200 gm2.

The wound dressing when wet may have shrinkage that is less than 25% or less than 15% of its original size/dimension.

The wound dressing may comprise a transmission layer and the layer is a foam. The transmission layer may be a polyurethane foam laminated to a polyurethane film.

The wound dressing may comprise one or more layers selected from the group comprising a soluble medicated film layer; an odor-absorbing layer; a spreading layer and an additional adhesive layer.

The wound dressing may be 2 mm and 4 mm thick.

The wound dressing may be characterized in that the keying layer bonds the absorbent core to a neighboring layer. In some embodiments, the keying layer may be positioned on either the wound facing side of the absorbent core or the non-wound facing side of the absorbent core. In some embodiments, the keying layer is positioned between the absorbent core and the wound contact layer. The keying layer is a polyamide web.

A more detailed description of the wound dressing of this type hereinabove is provided in EP1718257, the entirety of which is hereby incorporated by reference.

In some embodiments, the non-negative pressure wound dressing may be a compression bandage. Compression bandages are known for use in the treatment of oedema and other venous and lymphatic disorders, for example, of the lower limbs.

A compression bandage systems typically employ multiple layers including a padding layer between the skin and the compression layer or layers. The compression bandage may be useful for wounds such as handling venous leg ulcers.

The compression bandage in some embodiments may comprise a bandage system comprising an inner skin facing layer and an elastic outer layer, the inner layer comprising a first ply of foam and a second ply of an absorbent nonwoven web, the inner layer and outer layer being sufficiently elongated so as to be capable of being wound about a patient's limb. A compression bandage of this type is disclosed in WO99/58090, the entirety of which is hereby incorporated by reference.

In some embodiments, the compression bandage system comprises: a) an inner skin facing, elongated, elastic bandage comprising: (i) an elongated, elastic substrate, and
(ii) an elongated layer of foam, said foam layer being affixed to a face of said substrate and extending 33% or more across said face of substrate in transverse direction and 67% or more across said face of substrate in longitudinal direction; and b) an outer, elongated, self-adhering elastic bandage; said bandage having a compressive force when extended; wherein, in use, said foam layer of the inner bandage faces the skin and the outer bandage overlies the inner bandage. A compression bandage of this type is disclosed in WO2006/110527, the entirety of which is hereby incorporated by reference.

In some embodiments other compression bandage systems such as those disclosed in U.S. Pat. No. 6,759,566 and US 2002/0099318, the entirety of each of which is hereby incorporated by reference.

Negative Pressure Wound Dressing

In some embodiments, treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy (NPWT) involves placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria.

Some of the dressings used in NPWT can include many different types of materials and layers, for example, gauze, pads, foam pads or multi-layer wound dressings. One example of a multi-layer wound dressing is the PICO dressing, available from Smith & Nephew, includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg In addition, negative pressure that is "less" or "smaller" than X mmHg corresponds to pressure that is closer to atmospheric pressure (such as, −40 mmHg is less than −60 mmHg). Negative pressure that is "more" or "greater" than −X mmHg corresponds to pressure that is further from atmospheric pressure (such as, −80 mmHg is more than −60 mmHg). In some embodiments, local ambient atmospheric pressure is used as a reference point, and such local atmospheric pressure may not necessarily be, for example, 760 mmHG.

The negative pressure range for some embodiments of the present disclosure can be approximately −80 mmHg, or between about −20 mmHg and −200 mmHg Note that these pressures are relative to normal ambient atmospheric pressure, which can be 760 mmHg Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, or in synchronization with one or more patient physiological indices (such as, heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753, 894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No.

PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,908, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound dressing components, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158 A1 on Nov. 24, 2016, titled "FLUIDIC CONNECTOR FOR NEGATIVE PRESSURE WOUND THERAPY," the disclosure of each of which is hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump or associated electronics described herein may also be used in combination or in addition to those described in International Application PCT/EP2016/059329 filed Apr. 26, 2016, published as WO 2016/174048 on Nov. 3, 2016, entitled "REDUCED PRESSURE APPARATUS AND METHODS," the disclosure of which is hereby incorporated by reference in its entirety.

NPWT System Overview

FIG. 1A illustrates an embodiment of a negative or reduced pressure wound treatment (or TNP) system 102 comprising a wound filler 108 placed inside a wound cavity 104, the wound cavity sealed by a wound cover 106. The wound filler 108 in combination with the wound cover 106 can be referred to as wound dressing. A single or multi lumen tube or conduit 112 is connected the wound cover 106 with a pump assembly 114 configured to supply reduced pressure. The wound cover 106 can be in fluidic communication with the wound cavity 104. In any of the system embodiments disclosed herein, as in the embodiment illustrated in FIG. 1A, the pump assembly can be a canisterless pump assembly (meaning that exudate is collected in the wound dressing or is transferred via tube 112 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing.

The wound filler 108 can be any suitable type, such as hydrophilic or hydrophobic foam, gauze, inflatable bag, and so on. The wound filler 108 can be conformable to the wound cavity 104 such that it substantially fills the cavity. The wound cover 106 can provide a substantially fluid impermeable seal over the wound cavity 104. The wound cover 106 can have a top side and a bottom side, and the bottom side adhesively (or in any other suitable manner) seals with wound cavity 104. The conduit 112 or lumen or any other conduit or lumen disclosed herein can be formed from polyurethane, PVC, nylon, polyethylene, silicone, or any other suitable material.

Some embodiments of the wound cover 106 can have a port (not shown) configured to receive an end of the conduit 112. For example, the port can be RENASYS Soft Port available from Smith & Nephew. In other embodiments, the conduit 112 can otherwise pass through or under the wound cover 106 to supply reduced pressure to the wound cavity 104 so as to maintain a desired level of reduced pressure in the wound cavity. The conduit 112 can be any suitable article configured to provide at least a substantially sealed fluid flow pathway between the pump assembly 114 and the wound cover 106, so as to supply the reduced pressure provided by the pump assembly 114 to wound cavity 104.

The wound cover 106 and the wound filler 108 can be provided as a single article or an integrated single unit. In some embodiments, no wound filler is provided and the wound cover by itself may be considered the wound dressing. The wound dressing may then be connected, via the conduit 112, to a source of negative pressure, such as the pump assembly 114. The pump assembly 114 can be miniaturized and portable, although larger conventional pumps such can also be used.

The wound cover 106 can be located over a wound site to be treated. The wound cover 106 can form a substantially sealed cavity or enclosure over the wound site. In some embodiments, the wound cover 106 can be configured to have a film having a high water vapor permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 114 and tubing 112 so that the tubing 112 can be quickly and easily removed from the pump assembly 114 can facilitate or improve the process of dressing or pump changes, if necessary. Any of the pump embodiments disclosed herein can be configured to have any suitable connection between the tubing and the pump.

The pump assembly 114 can be configured to deliver negative pressure of approximately −80 mmHg, or between about −20 mmHg and 200 mmHg in some implementations. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 114.

In operation, the wound filler 108 is inserted into the wound cavity 104 and wound cover 106 is placed so as to seal the wound cavity 104. The pump assembly 114 provides a source of a negative pressure to the wound cover 106, which is transmitted to the wound cavity 104 via the wound filler 108. Fluid (such as, wound exudate) is drawn through the conduit 112, and can be stored in a canister. In some embodiments, fluid is absorbed by the wound filler 108 or one or more absorbent layers (not shown).

Wound dressings that may be utilized with the pump assembly and other embodiments of the present application include RENASYS-F, RENASYS-G, RENASYS AB, and Pico Dressings available from Smith & Nephew. Further description of such wound dressings and other components of a negative pressure wound therapy system that may be used with the pump assembly and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Wound Dressing Overview

Figure 1B:
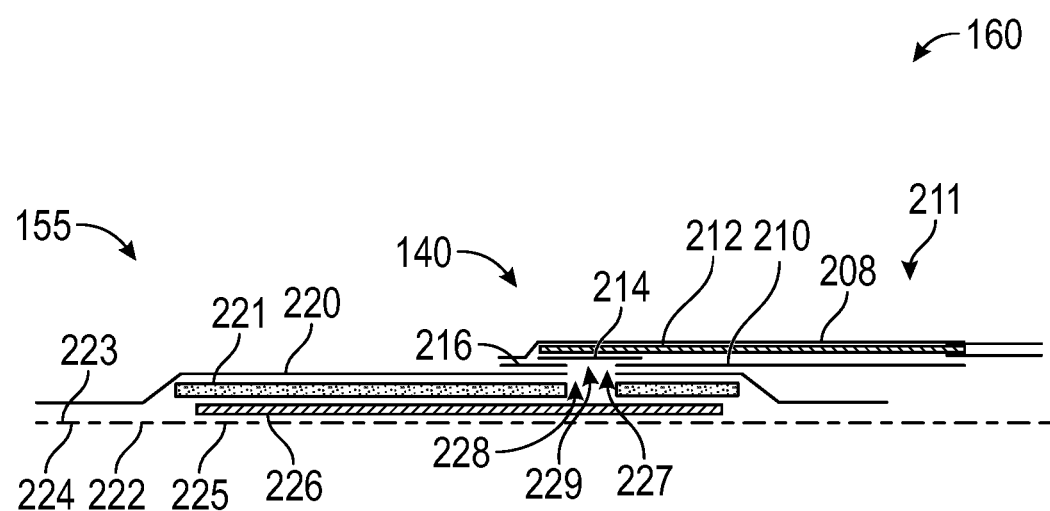
FIG. 1B illustrates a wound dressing according to some embodiments.

FIG. 1B illustrates a cross-section through a wound dressing 155 according to some embodiments. FIG. 1B also illustrates a fluidic connector 116 according to some embodiments. The wound dressing 155 can be similar to the wound dressing described in International Patent Publication WO2013175306 A2, which is incorporated by reference in its entirety. Alternatively, the wound dressing 155 can be any wound dressing embodiment disclosed herein or any combination of features of any number of wound dressing embodiments disclosed herein, can be located over a wound site to be treated. The wound dressing 155 may be placed as to form a sealed cavity over the wound, such as the wound cavity 104. In some embodiments, the wound dressing 155 includes a top or cover layer, or backing layer 220 attached to an optional wound contact layer 222, both of which are described in greater detail below. These two layers 220, 222 can be joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

The wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 (for example, facing the wound) and an upper surface 223 (for example, facing away from the wound). The perforations 225 can comprise through holes in the wound contact layer 222 which enable fluid to flow through the layer 222. The wound contact layer 222 helps prevent tissue ingrowth into the other material of the wound dressing. In some embodiments, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 155 while also creating an air tight seal around the absorbent pad in order to maintain negative pressure at the wound. In some embodiments, the wound contact layer is configured to allow unidirectional or substantially one-way or unidirectional flow of fluid through the wound contact layer when negative pressure is applied to the wound. For example, the wound contact layer can permit fluid to flow away from the wound through the wound contact layer, but not allow fluid to flow back toward the wound. In certain case, the perforations in the wound contact layer are configured to permit such one-way or unidirectional flow of fluid through the wound contact layer.

Some embodiments of the wound contact layer 222 may also act as a carrier for an optional lower and upper adhesive layer (not shown). For example, a lower pressure sensitive adhesive may be provided on the lower surface 224 of the wound dressing 155 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 155 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In particular, the transmission layer 226 can ensure that an open air channel can be maintained to communicate negative pressure over the wound area even when the absorbent layer has absorbed substantial amounts of exudates. The layer 226 can remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

In some embodiments, to improve the liquid flow across the transmission layer 226 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats or waxes used previously which might interfere with the hydrophilic capabilities of the transmission layer. An additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material can be provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 221 may also aid in drawing fluids towards the backing layer 220.

The material of the absorbent layer 221 may also prevent liquid collected in the wound dressing 155 from flowing freely within the dressing, and can act so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 or Chem-Posite™11C-450. In some embodiments, the absorbent layer 221 may comprise a composite comprising superabsorbent powder, fibrous material such as cellulose, and bonding fibers. In some embodiments, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 can be provided in the backing layer 220 to allow a negative pressure to be applied to the dressing 155. In some embodiments, the fluidic connector 116 is attached or sealed to the top of the backing layer 220 over the orifice 227 made into the dressing 155, and communicates negative pressure through the orifice 227. A length of tubing may be coupled at a first end to the fluidic connector 116 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 116 may be adhered and sealed to the backing layer 220 using an adhesive such as an acrylic, cyanoacrylate, epoxy, UV curable or hot melt adhesive. The fluidic connector 116 may be formed from a soft polymer, for example a polyethylene, a polyvinyl chloride, a silicone or polyurethane having a hardness of 30 to 90 on the Shore A scale. In some embodiments, the fluidic connector 116 may be made from a soft or conformable material.

In some embodiments, the absorbent layer 221 includes at least one through hole 228 located so as to underlie the fluidic connector 116. The through hole 228 may in some embodiments be the same size as the opening 227 in the backing layer, or may be bigger or smaller. As illustrated in FIG. 1B a single through hole can be used to produce an opening underlying the fluidic connector 116. It will be appreciated that multiple openings could alternatively be utilized. Additionally should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 can be provided in the absorbent layer 221 beneath the orifice 227 such that the orifice is connected directly to the transmission layer 226 as illustrated in FIG. 1B. This allows the negative pressure applied to the fluidic connector 116 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in International Patent Publication WO2014020440, the entirety of which is hereby incorporated by reference, may be provided over the absorbent layer 221 and beneath the backing layer 220.

The backing layer 220 is can be gas impermeable, but moisture vapor permeable, and can extend across the width of the wound dressing 155. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 220 and a wound site where a negative pressure can be established. The backing layer 220 can be sealed to the wound contact layer 222 in a border region around the circumference of the dressing, ensuring that no air is drawn in through the border area, for example via adhesive or welding techniques. The backing layer 220 protects the wound from external bacterial contamination (bacterial bather) and allows liquid from wound exudates to be transferred through the layer and evaporated from the film outer surface. The backing layer 220 can include two layers; a polyurethane film and an adhesive pattern spread onto the film. The polyurethane film can be moisture vapor permeable and may be manufactured from a material that has an increased water transmission rate when wet. In some embodiments the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIG. 1B, the absorbent layer 221 may define a smaller perimeter than that of the backing layer 220, such that a boundary or border region is defined between the edge of the absorbent layer 221 and the edge of the backing layer 220.

As shown in FIG. 1B, one embodiment of the wound dressing 155 comprises an aperture 228 in the absorbent layer 221 situated underneath the fluidic connector 116. In use, for example when negative pressure is applied to the dressing 155, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 11, or the orifice 227.

For example, in embodiments with a single fluidic connector 116 and through hole, it may be preferable for the fluidic connector 116 and through hole to be located in an off-center position. Such a location may permit the dressing 155 to be positioned onto a patient such that the fluidic connector 116 is raised in relation to the remainder of the dressing 155. So positioned, the fluidic connector 116 and the filter 214 may be less likely to come into contact with wound fluids that could prematurely occlude the filter 214 so as to impair the transmission of negative pressure to the wound site.

Turning now to the fluidic connector 116, some embodiments include a sealing surface 216, a bridge 211 with a proximal end (closer to the negative pressure source) and a distal end 140, and a filter 214. The sealing surface 216 can form the applicator that is sealed to the top surface of the wound dressing. In some embodiments a bottom layer of the fluidic connector 116 may comprise the sealing surface 216. The fluidic connector 116 may further comprise an upper surface vertically spaced from the sealing surface 216, which in some embodiments is defined by a separate upper layer of the fluidic connector. In other embodiments the upper surface and the lower surface may be formed from the same piece of material. In some embodiments the sealing surface 216 may comprise at least one aperture 229 therein to communicate with the wound dressing. In some embodiments the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer with optional spacer elements 215 configured to create a gap between the filter 214 and the transmission layer 226. In other embodiments, the sealing surface 216 may be positioned over an orifice in the cover layer and an aperture in the absorbent layer 220, permitting the fluidic connector 116 to provide air flow through the transmission layer 226. In some embodiments, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 can be encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge, and spacer elements 215 are configured to prevent the fluidic connector from contacting the transmission layer 226. These elements will be described in greater detail below.

Some embodiments may further comprise an optional second fluid passage positioned above the first fluid passage 212. For example, some embodiments may provide for an air leak may be disposed at the proximal end of the top layer that is configured to provide an air path into the first fluid passage 212 and dressing 155 similar to the suction adapter as described in U.S. Pat. No. 8,801,685, which is incorporated by reference herein in its entirety.

In some embodiment, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected can be suited to channeling wound exudate away from the wound and for transmitting negative pressure or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between −40 to −150 mmHg In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm. Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system can be conformable and soft, which may help to avoid pressure ulcers and other complications which may result from a wound treatment system being pressed against the skin of a patient.

In some embodiments, the filter element 214 is impermeable to liquids, but permeable to gases, and is provided to act as a liquid barrier and to ensure that no liquids are able to escape from the wound dressing 155. The filter element 214 may also function as a bacterial barrier. Typically the pore size is 0.2 μm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port or the cover film over the orifice. For example, the filter element 214 may be molded into the fluidic connector 116, or may be adhered to one or both of the top of the cover layer and bottom of the suction adapter 160 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments, filter element 214 comprises a support layer and an acrylic co-polymer membrane formed on the support layer. In some embodiments, the wound dressing 155 according to certain embodiments uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

The wound dressing 155 may comprise spacer elements 215 in conjunction with the fluidic connector 116 and the filter 214. With the addition of such spacer elements 215 the fluidic connector 116 and filter 214 may be supported out of direct contact with the absorbent layer 220 or the transmission layer 226. The absorbent layer 220 may also act as an additional spacer element to keep the filter 214 from contacting the transmission layer 226. Accordingly, with such a configuration contact of the filter 214 with the transmission layer 226 and wound fluids during use may thus be minimized.

Similar to the embodiments of wound dressings described above, some wound dressings comprise a perforated wound contact layer with silicone adhesive on the skin-contact face and acrylic adhesive on the reverse. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

Figure 1C:
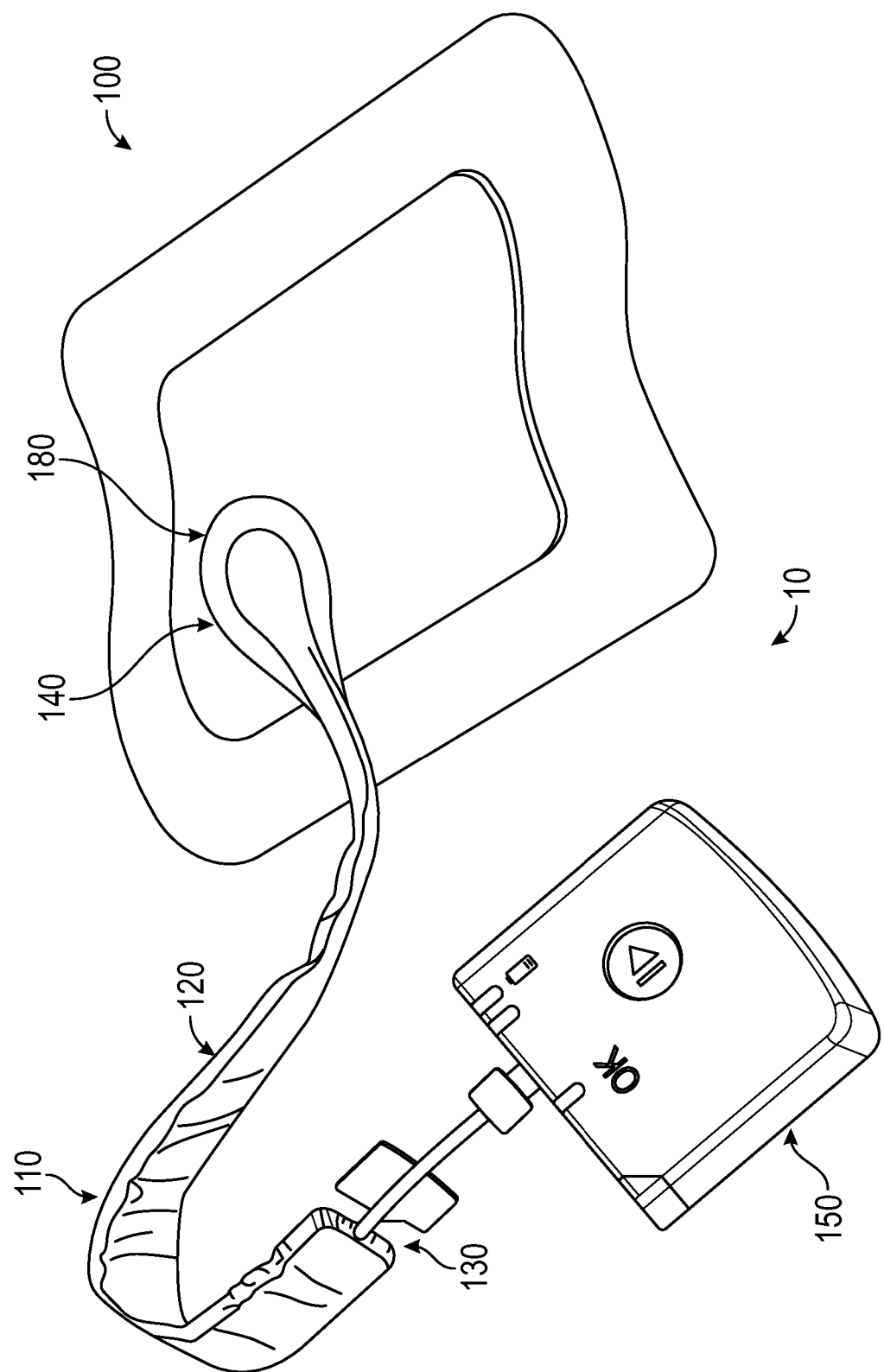
FIG. 1C illustrates a negative pressure wound treatment system employing a flexible fluidic connector and a wound dressing capable of absorbing and storing wound exudate according to some embodiments.
Figure 1D:
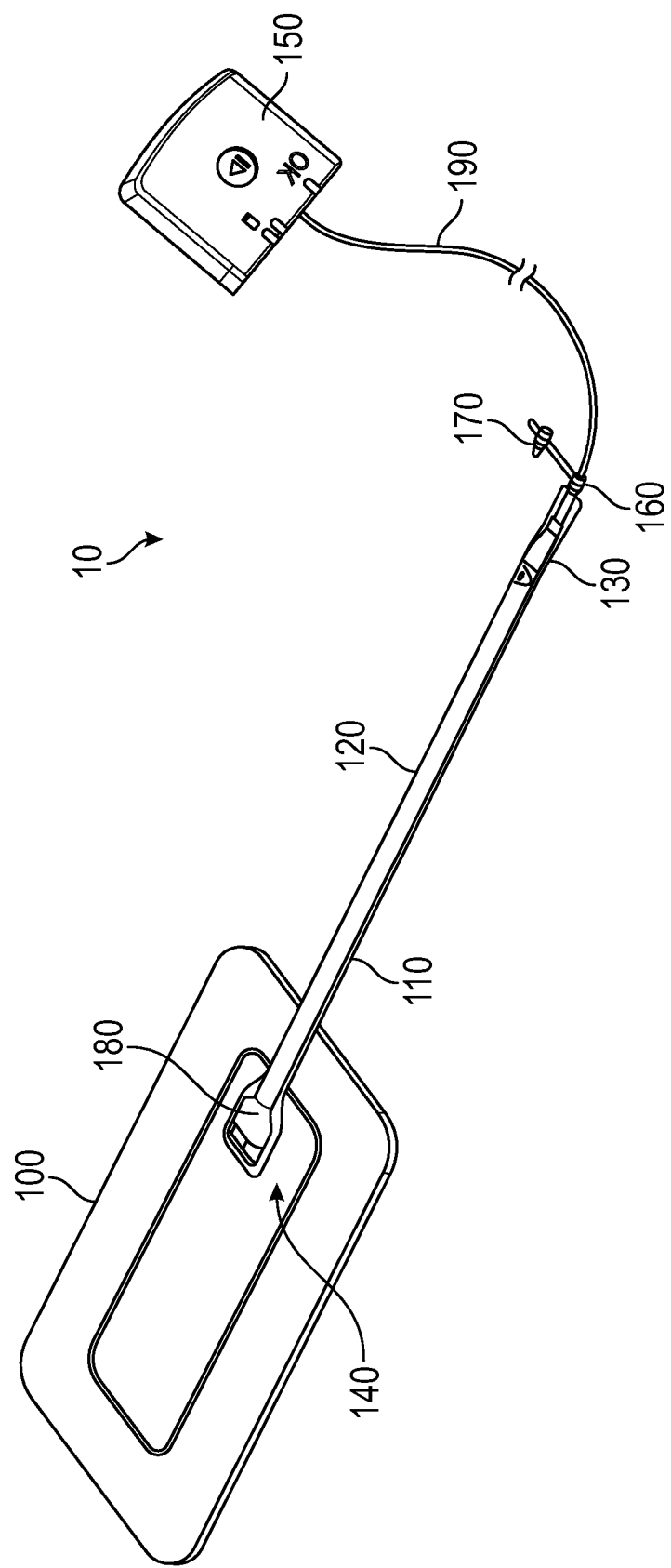
FIG. 1D illustrates a negative pressure wound treatment system employing a flexible fluidic connector and a wound dressing capable of absorbing and storing wound exudate according to some embodiments.

FIGS. 1C-1D illustrate embodiments of a negative pressure wound treatment system 10 employing a wound dressing 100 in conjunction with a fluidic connector 110. Here, the fluidic connector 110 may comprise an elongate conduit, for example, a bridge 120 having a proximal end 130 and a distal end 140, and an applicator 180 at the distal end 140 of the bridge 120. An optional coupling 160 can be disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, such as illustrated in FIGS. 1A-1B, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the dressing 100 is placed over a suitably-prepared wound, which may in some cases be filled with a wound packing material such as foam or gauze. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube 190 to the coupling 160, or is connected directly to the coupling 160 or to the bridge 120. The pump is then activated, thereby supplying negative pressure to the wound. Application of negative pressure may be applied until a desired level of healing of the wound is achieved.

Figure 1E:
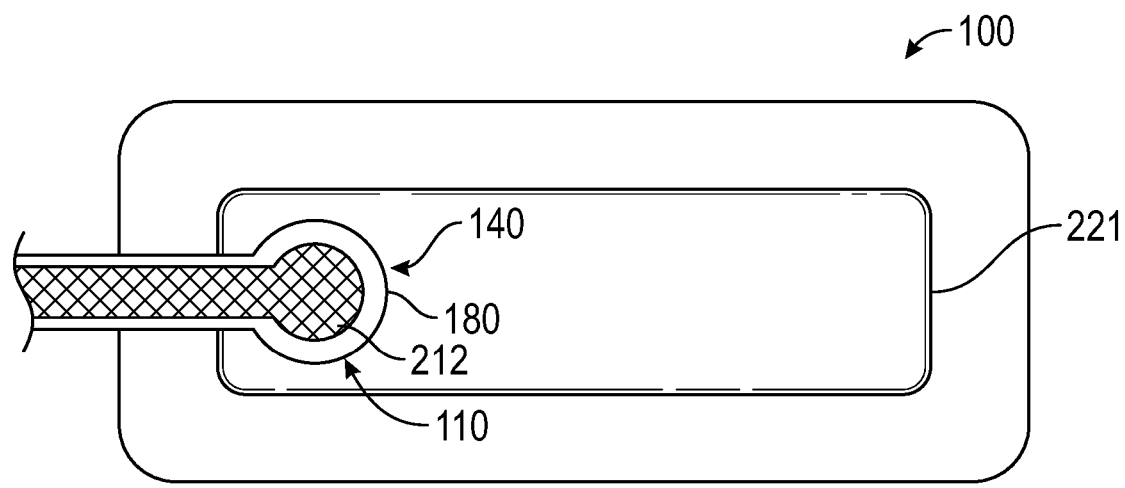
FIG. 1E illustrates a negative pressure wound treatment system employing a flexible fluidic connector and a wound dressing capable of absorbing and storing wound exudate according to some embodiments.

As shown in FIG. 1E, the fluidic connector 110 comprises an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 10 may comprise two or more fluidic connectors 110, each comprising one or more heads 140, in fluidic communication therewith. In an embodiment, the head 140 may measure 30 mm along its widest edge. The head 140 forms at least in part the applicator 180, described above, that is configured to seal against a top surface of the wound dressing.

Figure 1F:
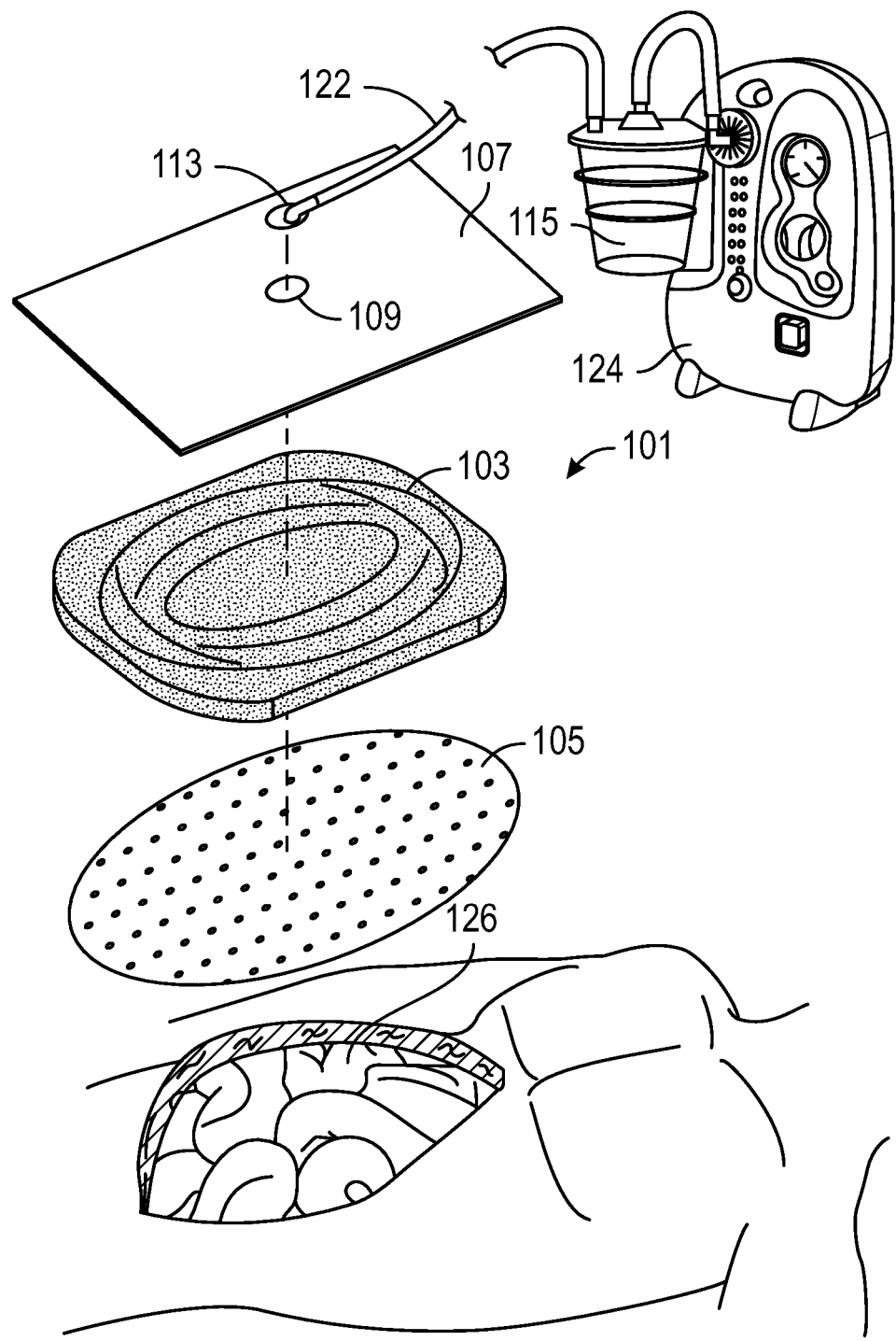
FIG. 1F illustrates of a negative pressure wound therapy system according to some embodiments.

Turning to FIG. 1F, treatment of other wound types, such as larger abdominal wounds, with negative pressure in certain embodiments uses a negative pressure treatment system 101 as illustrated schematically here. In this embodiment, a wound 126, illustrated here as an abdominal wound, may benefit from treatment with negative pressure. Such abdominal wounds may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening—particularly in the abdominal cavity—remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound. The application of reduced or negative pressure to a wound has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound 106 can be beneficial to a patient.

Accordingly, certain embodiments provide for a wound contact layer 105 to be placed over the wound 126. The wound contact layer can also be referred to as an organ protection layer and/or a tissue protection layer. Preferably, the wound contact layer 105 can be a thin, flexible material which will not adhere to the wound or the exposed viscera in close proximity. For example, polymers such as polyurethane, polyethylene, polytetrafluoroethylene, or blends thereof may be used. In one embodiment, the wound contact layer is permeable. For example, the wound contact layer 105 can be provided with openings, such as holes, slits, or channels, to allow the removal of fluids from the wound 126 or the transmittal of negative pressure to the wound 126. Additional embodiments of the wound contact layer 105 are described in further detail below.

Certain embodiments of the negative pressure treatment system 101 may also use a porous wound filler 103, which can be disposed over the wound contact layer 105. This pad 103 can be constructed from a porous material, for example foam, that is soft, resiliently flexible, and generally conformable to the wound 126. Such a foam can include an open-celled and reticulated foam made, for example, of a polymer. Suitable foams include foams composed of, for example, polyurethane, silicone, and polyvinyl alcohol. Preferably, this pad 103 can channel wound exudate and other fluids through itself when negative pressure is applied to the wound. Some pads 103 may include preformed channels or openings for such purposes. In certain embodiments, the pad 103 may have a thickness between about one inch and about two inches. The pad may also have a length of between about 16 and 17 inches, and a width of between about 11 and 12 inches. In other embodiments, the thickness, width, and/or length can have other suitable values. Other embodiments of wound fillers that may be used in place of or in addition to the pad 103 are discussed in further detail below.

Preferably, a drape 107 is used to seal the wound 126. The drape 107 can be at least partially liquid impermeable, such that at least a partial negative pressure may be maintained at the wound. Suitable materials for the drape 107 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfort and avoid skin maceration, the drapes in certain embodiments are at least partly breathable, such that water vapor is able to pass through without remaining trapped under the dressing. An adhesive layer may be provided on at least a portion the underside of the drape 107 to secure the drape to the skin of the patient, although certain embodiments may instead use a separate adhesive or adhesive strip. Optionally, a release layer may be disposed over the adhesive layer to protect it prior to use and to facilitate handling the drape 107; in some embodiments, the release layer may be composed of multiple sections.

The negative pressure system 101 can be connected to a source of negative pressure, for example a pump 114. One example of a suitable pump is the RENASYS EZ pump available from Smith & Nephew. The drape 107 may be connected to the source of negative pressure 114 via a conduit 122. The conduit 122 may be connected to a port 113 situated over an aperture 109 in the drape 107, or else the conduit 122 may be connected directly through the aperture 109 without the use of a port. In a further alternative, the conduit may pass underneath the drape and extend from a side of the drape. U.S. Pat. No. 7,524,315 discloses other similar aspects of negative pressure systems and is hereby incorporated by reference in its entirety and should be considered a part of this specification.

In many applications, a container or other storage unit 115 may be interposed between the source of negative pressure 124 and the conduit 122 so as to permit wound exudate and other fluids removed from the wound to be stored without entering the source of negative pressure. Certain types of negative pressure sources—for example, peristaltic pumps—may also permit a container 115 to be placed after the pump 124. Some embodiments may also use a filter to prevent fluids, aerosols, and other microbial contaminants from leaving the container 115 and/or entering the source of negative pressure 124. Further embodiments may also include a shut-off valve or occluding hydrophobic and/or oleophobic filter in the container to prevent overflow; other embodiments may include sensing means, such as capacitive sensors or other fluid level detectors that act to stop or shut off the source of negative pressure should the level of fluid in the container be nearing capacity. At the pump exhaust, it may also be preferable to provide an odor filter, such as an activated charcoal canister.

Figure 1G:
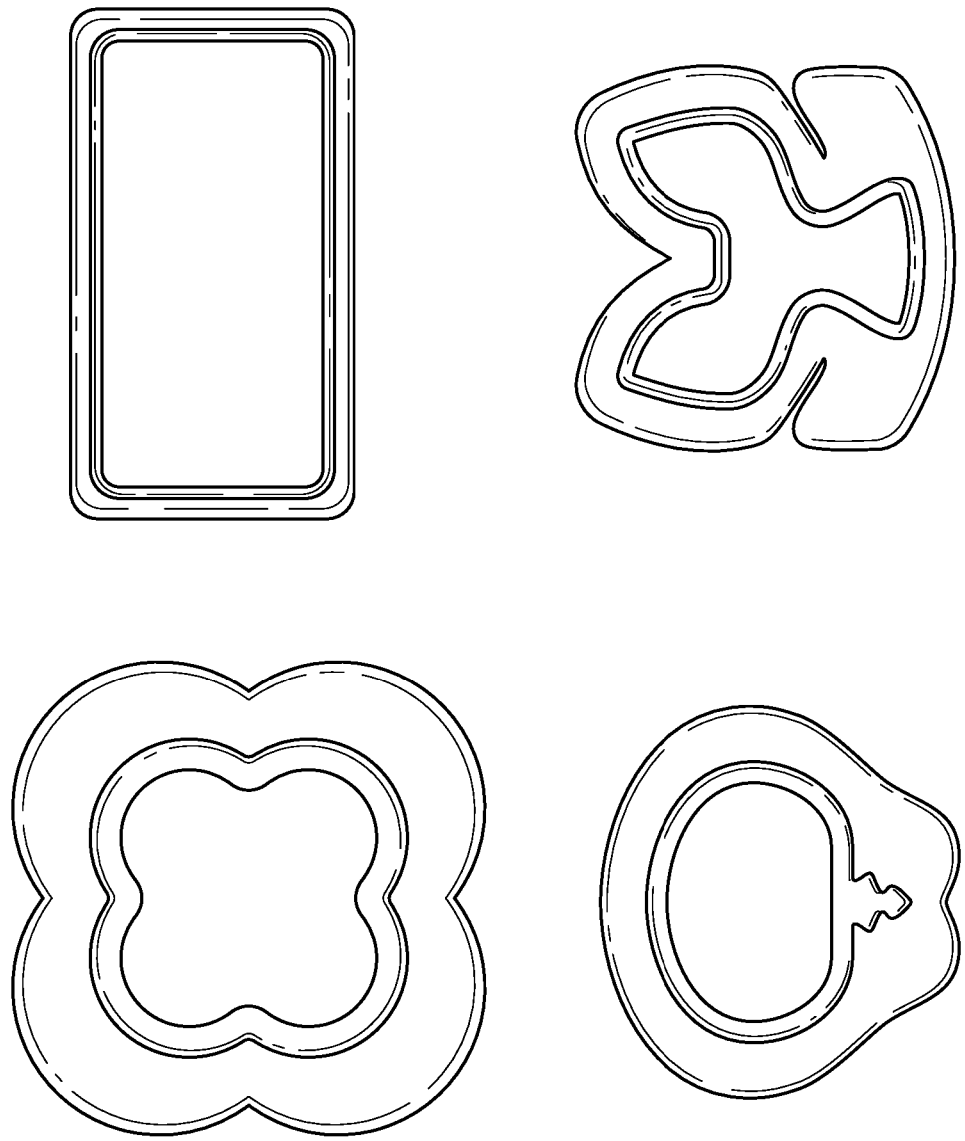
FIG. 1G illustrates a wound treatment system employing a wound dressing capable of absorbing and storing wound exudate to be used without negative pressure according to some embodiments.

FIG. 1G illustrates various embodiments of a wound dressing that can be used for healing a wound without negative pressure. As shown in the dressings of FIG. 1G, the wound dressings can have multiple layers similar to the dressings described with reference to FIGS. 1C-1F except the dressings of FIG. 1G do not include a port or fluidic connector. The wound dressings of FIG. 1G can include a cover layer and wound contact layer as described herein. The wound dressing can include various layers positioned between the wound contact layer and cover layer. For example, the dressing can include one or more absorbent layers and/or one or more transmission layers as described herein with reference to FIGS. 1C-1F. Additionally, some embodiments related to wound treatment comprising a wound dressing described herein may also be used in combination or in addition to those described in U.S. Application Publication No. 2014/0249495, filed May 21, 2014, entitled "WOUND DRESSING AND METHOD OF TREATMENT" the disclosure of which are hereby incorporated by reference in its entirety, including further details relating to embodiments of wound dressings, the wound dressing components and principles, and the materials used for the wound dressings.

Wound Dressing with Sensors

In some cases, one or more sensors can a wound dressing that incorporates a number of sensors can be utilized in order to monitor characteristics of a wound as it heals. Collecting data from the wounds that heal well, and from those that do not, can provide useful insights towards identifying measurands to indicate whether a wound is on a healing trajectory.

Figure 2:
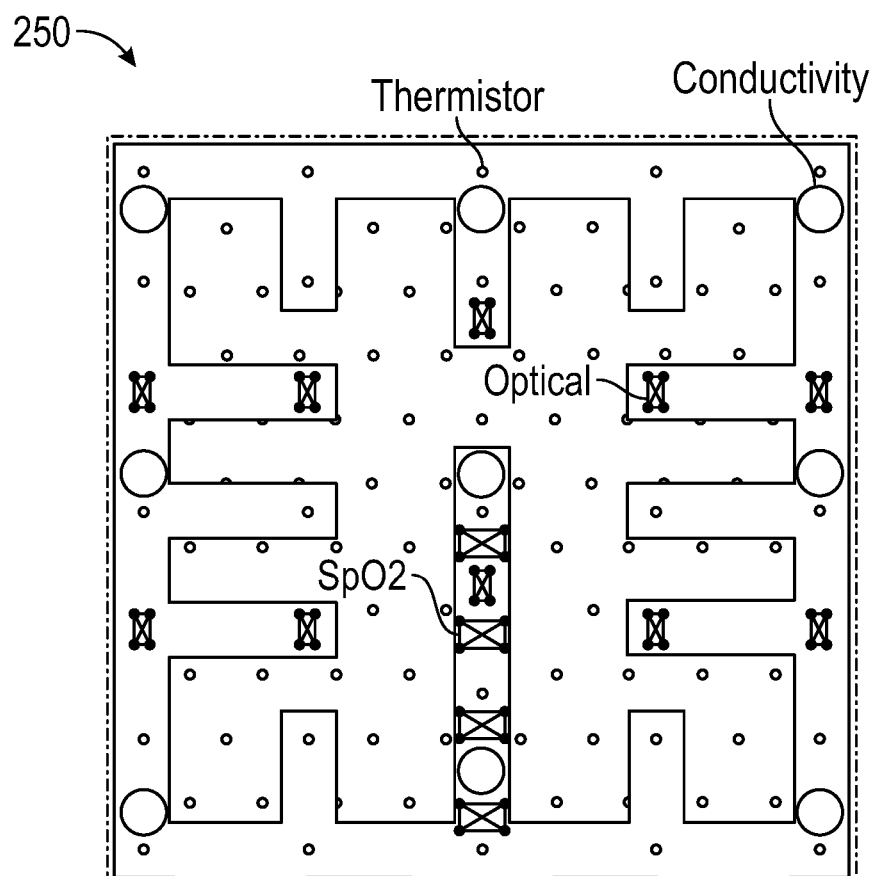
FIG. 2 illustrates a sensor array illustrating the sensor placement incorporated into a wound dressing according to some embodiments.
Figure 3A:
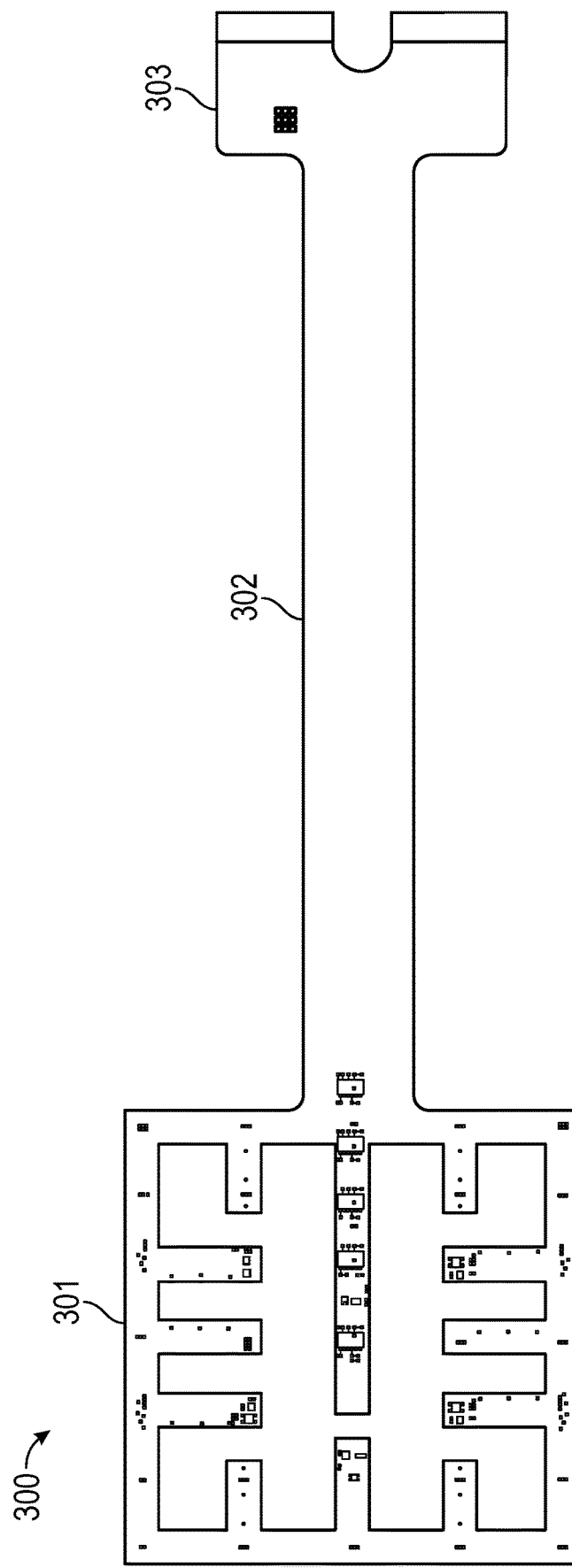
FIG. 3A illustrates a flexible sensor array including a sensor array portion, a tail portion and a connector pad end portion according to some embodiments.

In some implementations, a number of sensor technologies can be used in wound dressings or one or more components forming part of an overall wound dressing assembly. For example, as illustrated in FIGS. 2 and 3D, which depict wound dressings 250 and 320 with sensor arrays according to some embodiments, one or more sensors can be incorporated onto or into a wound contact layer, which may be a perforated wound contact layer as shown in FIG. 3D. The wound contact layer in FIGS. 2 and 3D is illustrated as having a square shape, but it will be appreciated that the wound contact layer may have other shapes such as rectangular, circular, oval, etc. In some embodiments, the sensor integrated wound contact layer can be provided as an individual material layer that is placed over the wound area and then covered by a wound dressing assembly or components of a wound dressing assembly, such as gauze, foam or other wound packing material, a superabsorbent layer, a drape, a fully integrated dressing like the Pico or Allevyn Life dressing, etc. In other embodiments, the sensor integrated wound contact layer may be part of a single unit dressing such as described herein.

The sensor-integrated wound contact layer can be placed in contact with the wound and will allow fluid to pass through the contact layer while causing little to no damage to the tissue in the wound. The sensor-integrated wound contact layer can be made of a flexible material such as silicone and can incorporate antimicrobials or other therapeutic agents known in the art. In some embodiments, the sensor-integrated wound contact layer can incorporate adhesives that adhere to wet or dry tissue. In some embodiments, the sensors or sensor array can be incorporated into or encapsulated within other components of the wound dressing such as the absorbent layer or spacer layer described above.

As shown in FIGS. 2 and 3D, five sensors can be used, including, for instance, sensors for temperature (such as, 25 thermistor sensors, in a 5×5 array, ~20 mm pitch), oxygen saturation or SpO2 (such as, 4 or 5 SpO2 sensors, in a single line from the center of the wound contact layer to the edge thereof, 10 mm pitch), tissue color (such as, 10 optical sensors, in 2×5 array, ~20 mm pitch; not all 5 sensors in each row of the array need be aligned), pH (such as, by measuring color of a pH sensitive pad, optionally using the same optical sensors as for tissue color), and conductivity (such as, 9 conductivity contacts, in a 3×3 array, ~40 mm pitch). As shown in FIG. 3A, the SpO2 sensors can be arranged in a single line from the center of or near the center of the wound contact layer to the edge of the wound contact layer. The line of SpO2 sensors can allow the sensor to take measurements in the middle of the wound, at the edge or the wound, or on intact skin to measure changes between the various regions. In some embodiments, the wound contact layer or sensor array can be larger than the size of the wound to cover the entire surface area of the wound as well as the surrounding intact skin. The larger size of the wound contact layer and/or sensor array and the multiple sensors can provide more information about the wound area than if the sensor was only placed in the center of the wound or in only one area at a time.

The sensors can be incorporated onto flexible circuit boards formed of flexible polymers including polyamide, polyimide (PI), polyester, polyethylene naphthalate (PEN), polyetherimide (PEI), along with various flyropolymers (FEP) and copolymers, or any material known in the art. The sensor array can be incorporated into a two-layer flexible circuit. In some embodiments, the circuit board can be a multi-layer flexible circuit board. In some embodiments, these flexible circuits can be incorporated into any layer of the wound dressing. In some embodiments, a flexible circuit can be incorporated into a wound contact layer. For example, the flexible circuit can be incorporated into a wound contact layer similar to the wound contact layer described with reference to FIG. 1B. The wound contact layer can have cutouts or slits that allow for one or more sensors to protrude out of the lower surface of the wound contact layer and contact the wound area directly.

In some embodiments, the sensor-integrated wound contact layer can include a first and second wound contact layer with the flexible circuit board sandwiched between the two layers of wound contact layer material. The first wound contact layer has a lower surface intended to be in contact with the wound and an upper surface intended to be in contact with flexible circuit board. The second wound contact layer has a lower surface intended to be in contact with the flexible circuit board and an upper surface intended to be in contact with a wound dressings or one or more components forming part of an overall wound dressing assembly. The upper surface of the first wound contact layer and the lower surface of the second wound contact layer can be adhered together with the flexible circuit board sandwiched between the two layers.

In some embodiments, the one or more sensors of the flexible circuit board can be fully encapsulated or covered by the wound contact layers to prevent contact with moisture or fluid in the wound. In some embodiments, the first wound contact layer can have cutouts or slits that allow for one or more sensors to protrude out of the lower surface and contact the wound area directly. For example, the one or more SpO2 sensors as shown in FIG. 3D are shown protruding out the bottom surface of the wound contact layer. In some embodiments, the SpO2 sensors can be mounted directly on a lower surface of the first wound contact layer. Some or all of the sensors and electrical or electronic components may be potted or encapsulated (for example, rendered waterproof or liquid-proof) with a polymer, for example, silicon or epoxy based polymers. The encapsulation with a polymer can prevent ingress of fluid and leaching of chemicals from the components. In some embodiments, the wound contact layer material can seal the components from water ingress and leaching of chemicals.

In some embodiments, gathering and processing information related to the wound can utilize three components, including a sensor array, a control or processing module, and software. These components are described in more detail herein.

FIG. 3A illustrates a flexible sensor array circuit board 300 that includes a sensor array portion 301, a tail portion 302, and a connector pad end portion 303 according to some embodiments. The sensor array portion 301 can include the sensors and associated circuitry. The sensor array circuit board 300 can include a long tail portion 302 extending from the sensor array portion 301. The connector pad end portion 303 can be enabled to connect to a control module or other processing unit to receive the data from the sensor array circuit. The long tail portion 302 can allow the control module to be placed distant from the wound, such as for example in a more convenient location away from the wound.

Figure 3B:
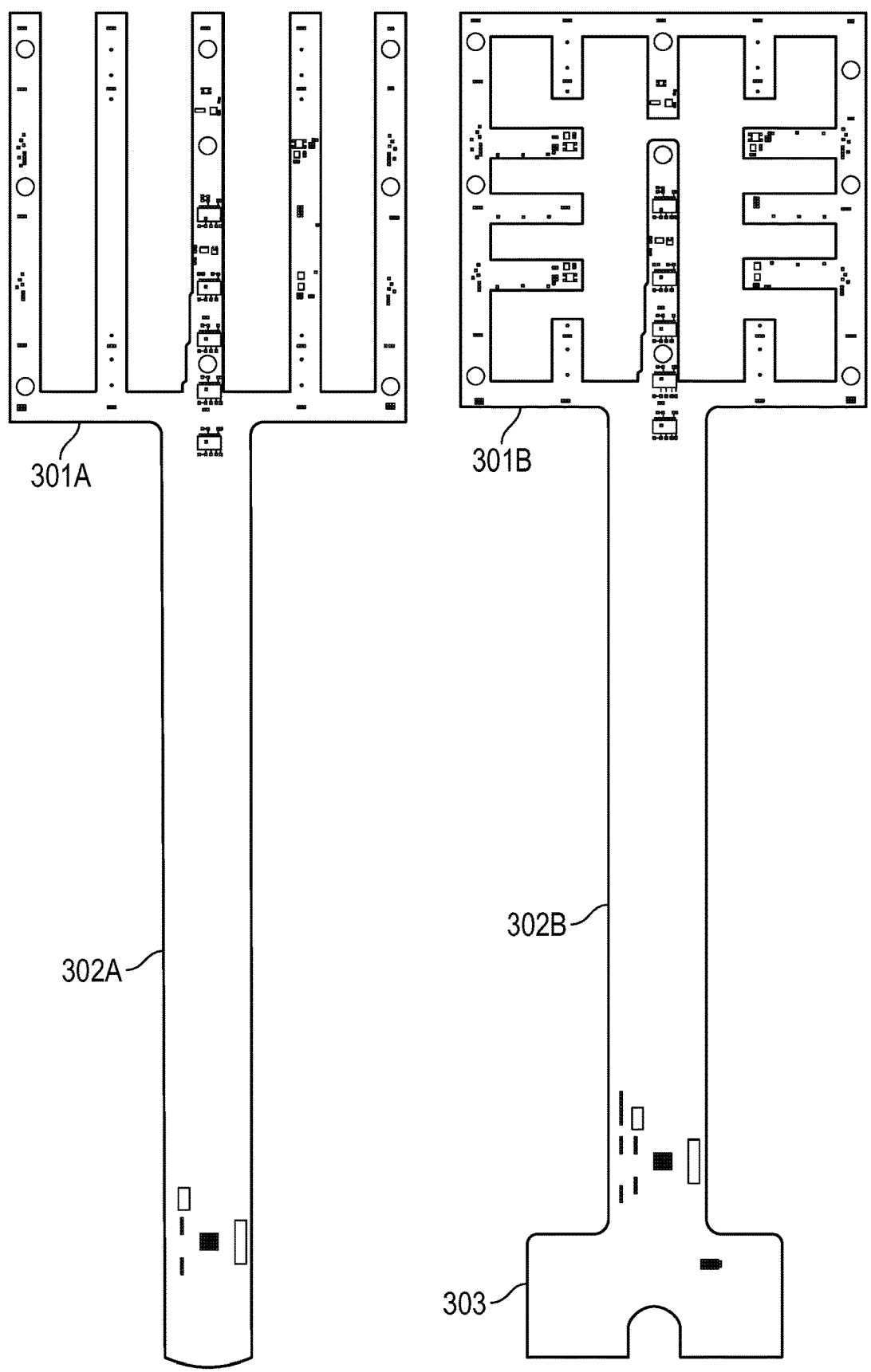
FIG. 3B illustrates flexible circuit boards with different sensor array geometries according to some embodiments.
Figure 3B:
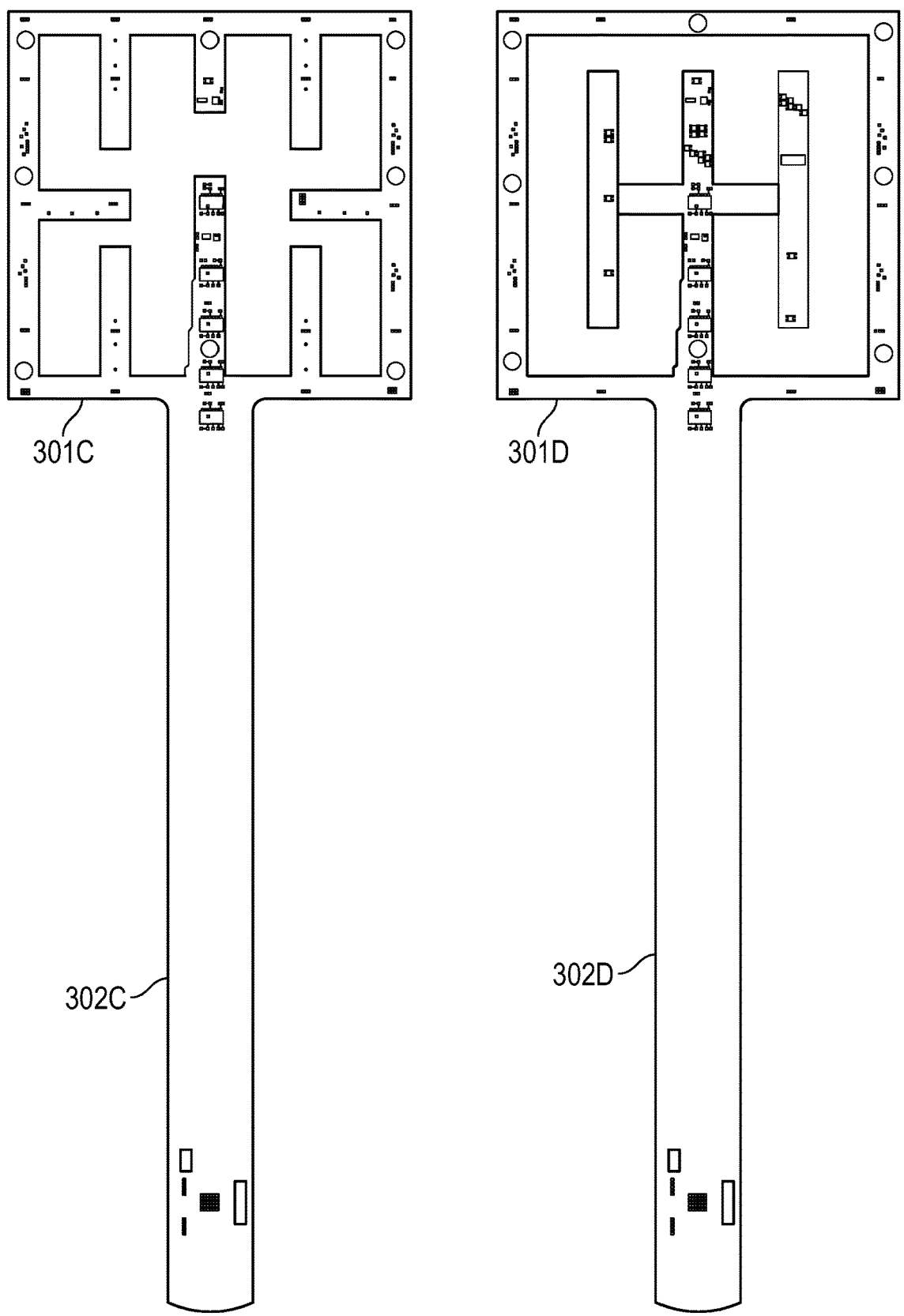

FIG. 3B illustrates embodiments of the flexible circuit boards with four different sensor array geometries 301A, 301B, 301C, and 301D according to some embodiments. The illustrated embodiments include tail portions 302A, 302B. 302C, and 302D. In some embodiments, four different sensor array geometries shown can be implemented in flexible circuits. While FIG. 3B show four different sensor array formats and configurations, the design 301B and 302B also includes the connector pads end portion 303 configured to provide electrical or electronic connection between the sponsor array 301B and a control module. One or more of the designs in 301A, 301C, or 301D can also include a connector pads end portion, such as the portion 303, to allow flexible circuit boards 301A, 301C, or 301D to communicate with a control module or other processing unit. In some embodiments, the sensor array communicates with the control module wirelessly and the tail portion may be omitted.

Figure 3C:
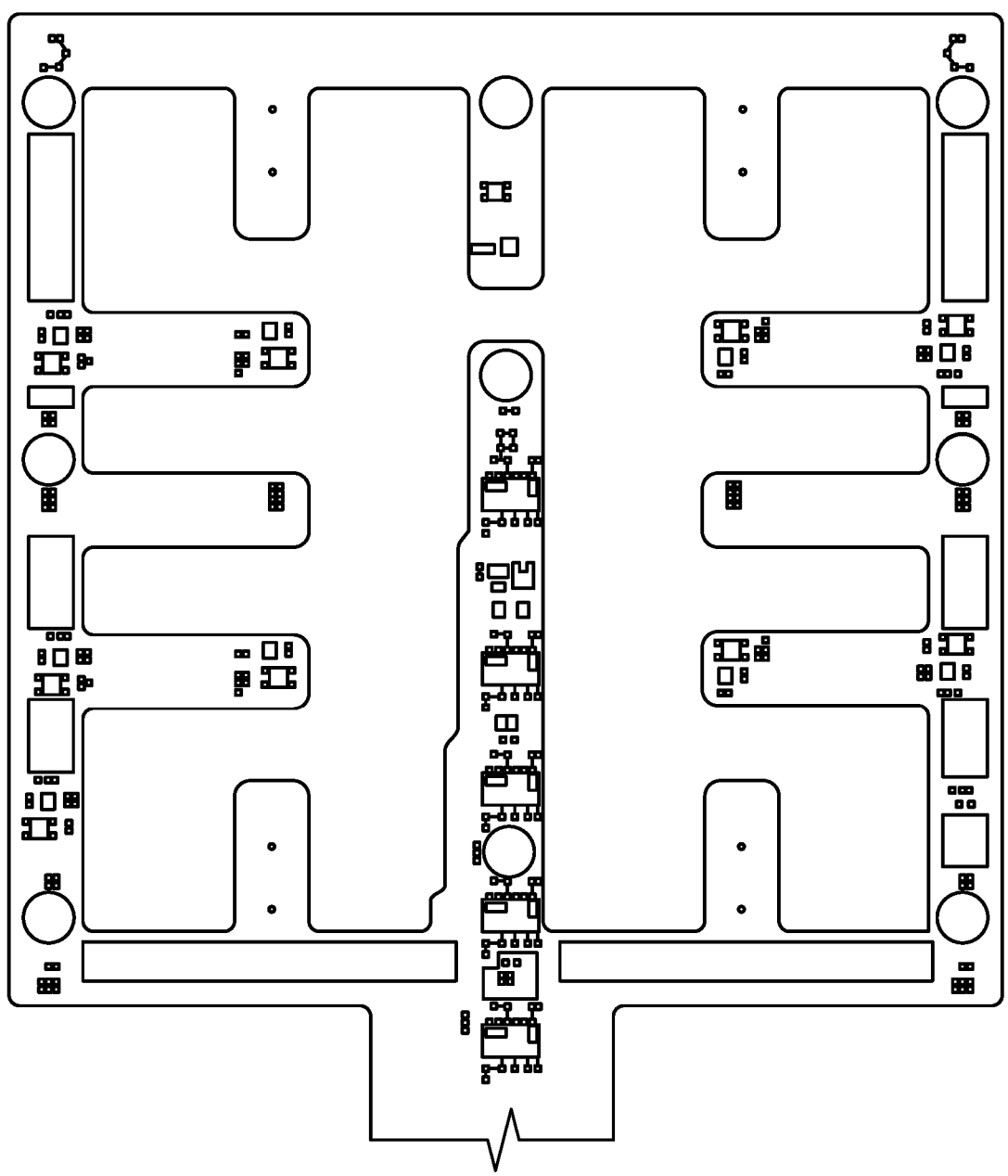
FIG. 3C illustrates the sensor array portion of a sensor array shown in FIG. 3B.
Figure 3D:
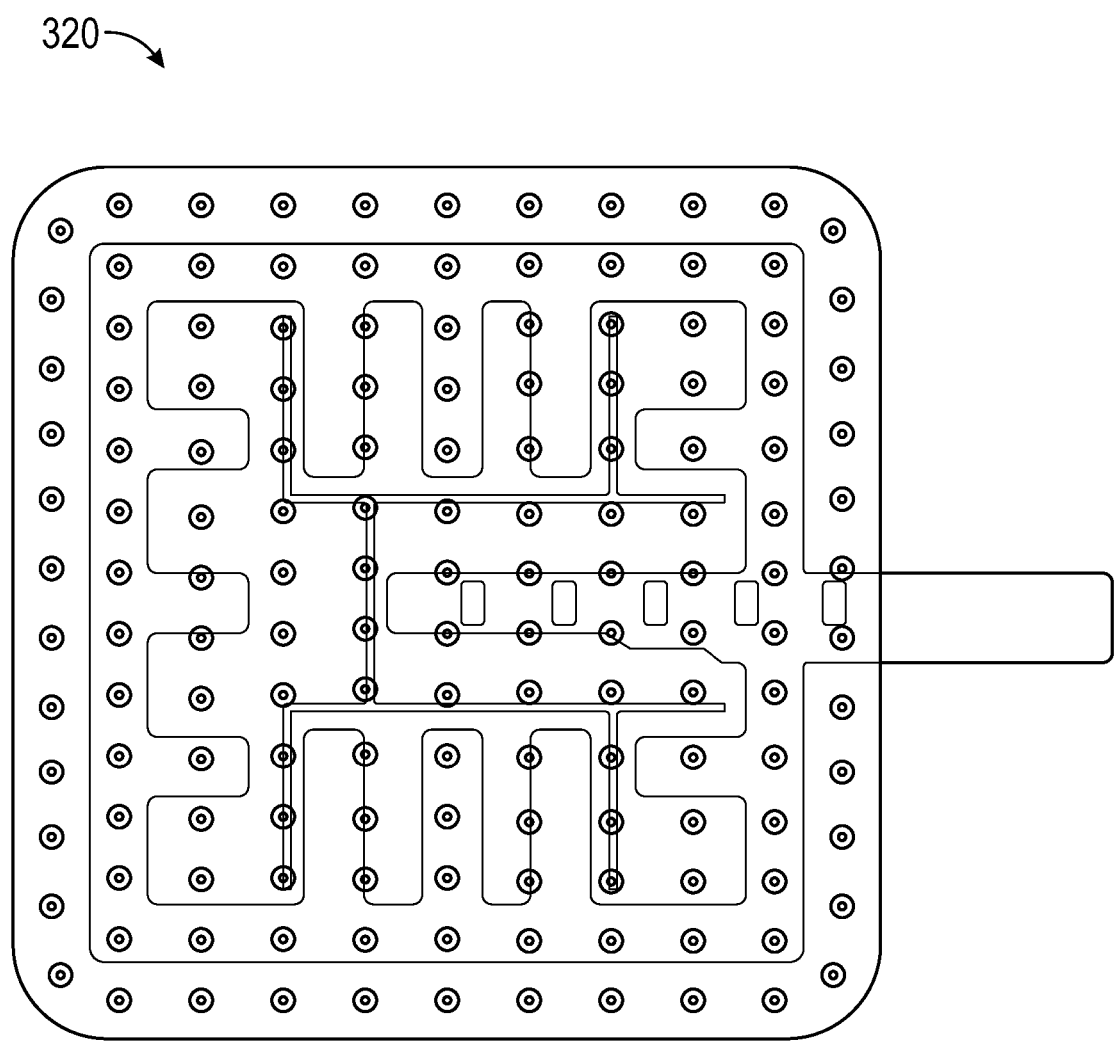
FIG. 3D illustrates a flexible sensor array incorporated into a perforated wound contact layer according to some embodiments.

FIG. 3C shows the sensor array portion 301B of the sensor array design shown of FIG. 3B in more detail. In any one or more of the embodiments of FIG. 2 or 3A-3D, the sensor array portion can include a plurality of portions that extend either around a perimeter of a wound dressing component such as a wound contact layer, or inward from an outer edge of the wound dressing component. For example, the illustrated embodiments include a plurality of linearly extending portions that may be parallel to edges of a wound dressing component, and in some embodiments, follow the entire perimeter of the wound dressing component. In some embodiments, the sensor array portion may comprise a first plurality of parallel linearly extending portions that are perpendicular to a second plurality of parallel linearly extending portions. These linearly extending portions may also have different lengths and may extend inward to different locations within an interior of a wound dressing component. The sensor array portion preferably does not cover the entire wound dressing component, so that gaps are formed between portions of the sensor array. As shown in FIG. 2, this allows some, and possibly a majority of the wound dressing component to be uncovered by the sensor array. For example, for a perforated wound contact layer as shown in FIGS. 2 and 3D, the sensor array portion 301 may not block a majority of the perforations in the wound contact layer. In some embodiments, the sensor array may also be perforated or shaped to match the perforations in the wound contact layer to minimize the blocking of perforations to fluid flow.

FIG. 3D illustrates a flexible sensor array incorporated into a perforated wound contact layer 320 according to some embodiments. As is illustrated, the sensor array can be sandwiched between two films or wound contact layers. The wound contact layers can have perforations formed as slits or holes as described herein that are small enough to help prevent tissue ingrowth into the wound dressing while allowing wound exudate to flow into the dressing. In some embodiments, the wound contact layers can have one or more slits that increase flexibility of the wound contact layer with integrated sensor array. In some embodiments, one of the wound contact layers can have extra cut outs to accommodate the sensors so that they can contact the skin directly.

Connectivity for the sensor array can vary depending on the various sensors and sensor array designs utilized. In some embodiments, for example as shown in FIG. 3B, a total of 79 connections can be used to connect the components of the sensor array. The sensor arrays can be terminated in two parallel 40-way 0.5 mm pitch Flat Flexible Cable (FFC) contact surfaces, with terminals on the top surface, designed to be connected to an FFC connector such as Molex 54104-4031.

In some embodiments, one or more of thermistors, conductivity sensors, SpO2 sensors, or color sensors can be used on the sensor array to provide information relating to conditions of the wound. The sensor array and individual sensors can assist a clinician in monitoring the healing of the wound. The one or more sensors can operate individually or in coordination with each other to provide data relating to the wound and wound healing characteristics.

Temperature sensors can use thermocouples or thermistors to measure temperature. The thermistors can be used to measure or track the temperature of the underlying wound or the thermal environment within the wound dressing. The thermometry sensors can be calibrated and the data obtained from the sensors can be processed to provide information about the wound environment. In some embodiments, an ambient sensor measuring ambient air temperature can also be used to assist in eliminating problems associated with environment temperature shifts.

Optical sensors can be used to measure wound appearance using an RGB sensor (for example, a red, green, blue, and clear (RGBC) sensor or red, green blue, and white (RGBW) sensor) with an illumination source. In some embodiments, both the RGB sensor and the illumination source would be pressed up against the skin, such that light would penetrate into the tissue and take on the spectral features of the tissue itself.

Light propagation in tissue can be dominated by two major phenomena, scattering and attenuation. For attenuation, as light passes through tissue, its intensity may be lost due to absorption by various components of the tissue. Blue light tends to be attenuated heavily, whilst light at the red end of the spectrum tends to be attenuated least.

Scattering processes can be more complex, and can have various "regimes" which must be considered. The first aspect of scattering is based on the size of the scattering center compared with the wavelength of incident light. If the scattering center is much smaller than the wavelength of light, then Rayleigh scattering can be assumed. If the scattering center is on the order of the wavelength of light, then a more detailed Mie scattering formulation must be considered. Another factor involved in scattering light is the distance between input and output of the scattering media. If the mean free path of the light (the distance between scattering events) is much larger than the distance traveled, then ballistic photon transport is assumed. In the case of tissue, scattering events are approximately 100 microns apart—so a 1 mm path distance would effectively randomize the photon direction and the system would enter a diffusive regime.

Ultra bright light emitting diodes (LEDs), an RGB sensor, and polyester optical filters can be used as components of the optical sensors to measure through tissue color differentiation. For example, because surface color can be measured from reflected light, a color can be measured from light which has passed through the tissue first for a given geometry. This can include color sensing from diffuse scattered light, from an LED in contact with the skin. In some embodiments, an LED can be used with an RGB sensor nearby to detect the light which has diffused through the tissue. The optical sensors can image with diffuse internal light or surface reflected light.

Additionally, the optical sensors can be used to measure autofluorescence. Autoflourescense is used because the tissue is absorbing light at one wavelength, and emitting at another. Additionally, dead tissue may not auto-fluoresce and so this could be a very strong indication as to if the tissue is healthy or not. Due to blue light (or even UV light) having such a short penetration depth, it may be very useful for example to have a UV light with a red sensitive photodiode nearby (or some other wavelength shifted band) to act as a binary test for healthy tissue, which would auto-fluoresce at a very particular wavelength.

Conductivity sensors can be used to determine the difference between living and dead tissue or to show a change in impedance due to a wound being opened up in morbid tissue. Conductivity sensors can include Ag/AgCl electrodes and an impedance analyzer. The conductivity sensors can be used to measure the change of impedance of a region of wound growth by measuring the impedance of the surrounding tissue/area. In some embodiments, the sensor array can utilize conductivity sensors to measure the change in conductivity on perimeter electrodes due to a wound size or wound shape change. In some embodiments, the conductivity sensors can be used in the wound bed or on the perimeter of the wound.

In some embodiments, pH changing pads can be used as a pH sensor. A spectrometer and a broadband white light source can be used to measure the spectral response of the pH dye. The illumination and imaging can be provided on the surface of the wound dressing that is in contact with the wound and at the same side as the fluid application, the bottom surface. Alternatively, in some embodiments, the illumination and imaging source can be provided on the surface of the wound dressing opposite the bottom surface and away from fluid application or the top surface of the dressing.

In some embodiments, pulse oximetry SpO2 sensors can be used. To measure how oxygenated the blood is and the pulsatile blood flow can be observed. Pulse oximetry measurements work by taking a time resolved measurement of light absorption/transmission in tissue at two different optical wavelengths. When hemoglobin becomes oxygenated, its absorption spectrum changes with regards to non-oxygenated blood. By taking a measurement at two different wavelengths, one gains a ratio metric measure of how oxygenated the blood is.

The components in the sensor array can be connected through multiple connections. In some embodiments, the thermistors can be arranged in groups of five. Each thermistor is nominally 10 kΩ, and each group of five has a common ground. There are five groups of thermistors, giving a total of 30 connections. In some embodiments, there can be nine conductivity terminals. Each conductivity terminal requires one connection, giving a total of 9 connections. In some embodiments, there can be five SpO2 sensors. Each SpO2 sensor requires three connections, plus power and ground (these are covered separately), giving a total of 15 connections. In some embodiments, there can be 10 color sensors. Each color sensor comprises an RGB LED and an RGB photodiode. Each color sensor requires six connections, however five of these are common to every sensor, giving a total of 15 connections. Power and ground are considered separately. In some embodiments, there can be 5 pH sensors. The pH sensors can be a color-change discs, and can be sensed using the color sensors described above. Therefore, the pH sensors require no additional connections. There can be three power rails, and seven ground return signals, giving a total of 10 common connections. In some embodiments, the sensor array can include 25 thermistor (Murata NCP15WB473E03RC), 9 conductivity terminal, 5 SpO2 (ADPD144RI), 10 RGB LED (such as KPTF-1616RGBC-13), 10 RGB Color Sensor, 10 FET, a printed circuit board (PCB), and an assembly.

A control module can be used to interface with the sensor array. In some embodiments, the control module can contain a power source, such as batteries, and electronics to drive the sensors. The control module can also log data at appropriate intervals and allow data transfer to an external computing device, such as a personal computer (PC). The control module can be customized to have various features depending on the sensors used in the sensor array and the data collected by the sensors. In some embodiments, the control module can be comfortable enough and small enough to be worn continuously for several weeks. In some embodiments, the control module can be positioned near the wound dressing or on the wound dressing. In some embodiments, the control module can be positioned in a remote location from the wound dressing and accompanying sensor array. The control module can communicate with the sensor array and wound dressing through electrical wires or through wireless communication whether positioned on the dressing, near the dressing, or remote from the wound dressing. In some embodiments, the control module can be adapted to be utilized with different sensor arrays and can enable easy replacement of the sensor array.

In some embodiments, the control module can include various requirements and combination of features including but not limited to the features listed in Table 1 below.

TABLE 1

Figure 3E:
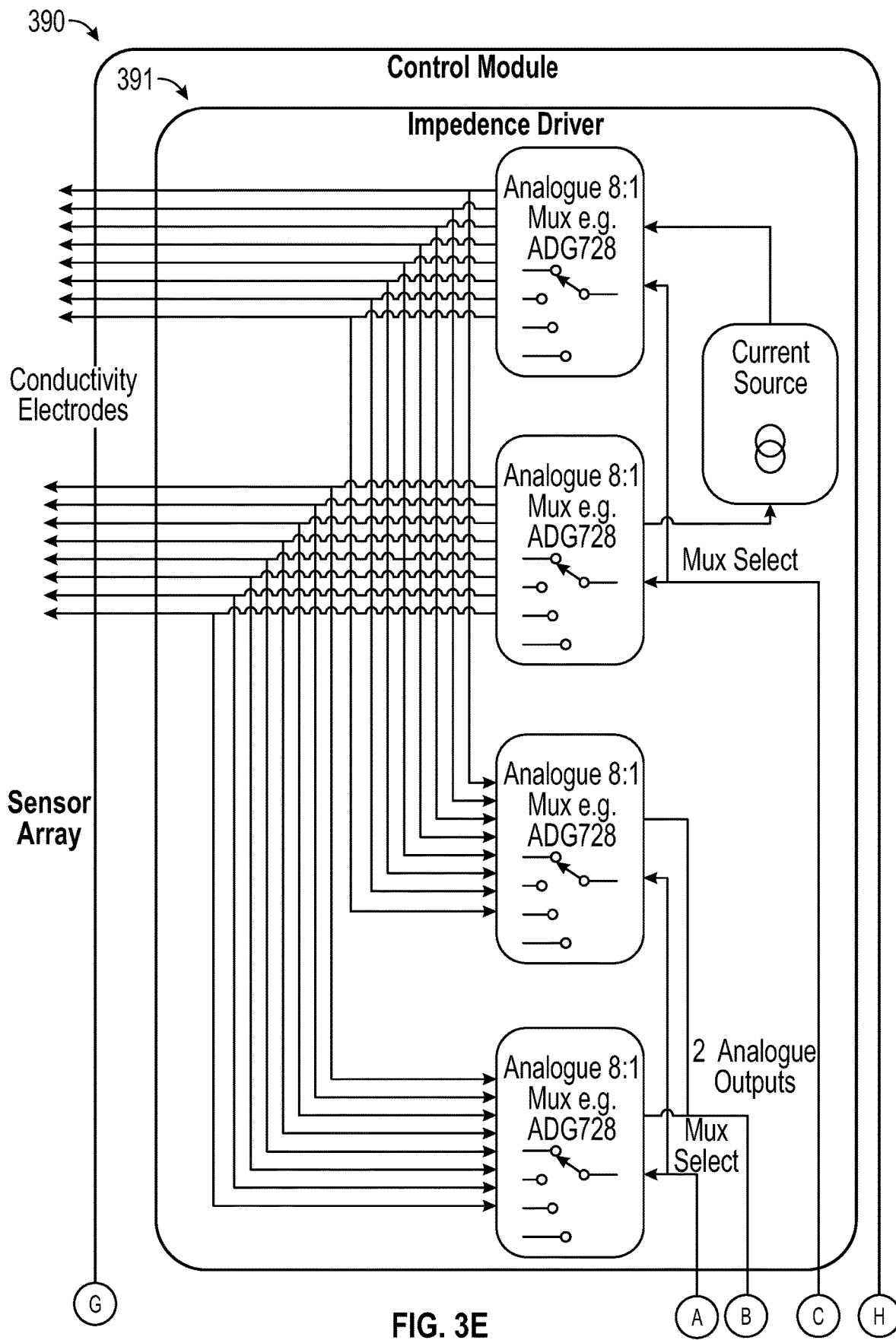
FIG. 3E illustrates a control module according to some embodiments.
Figure 3E:
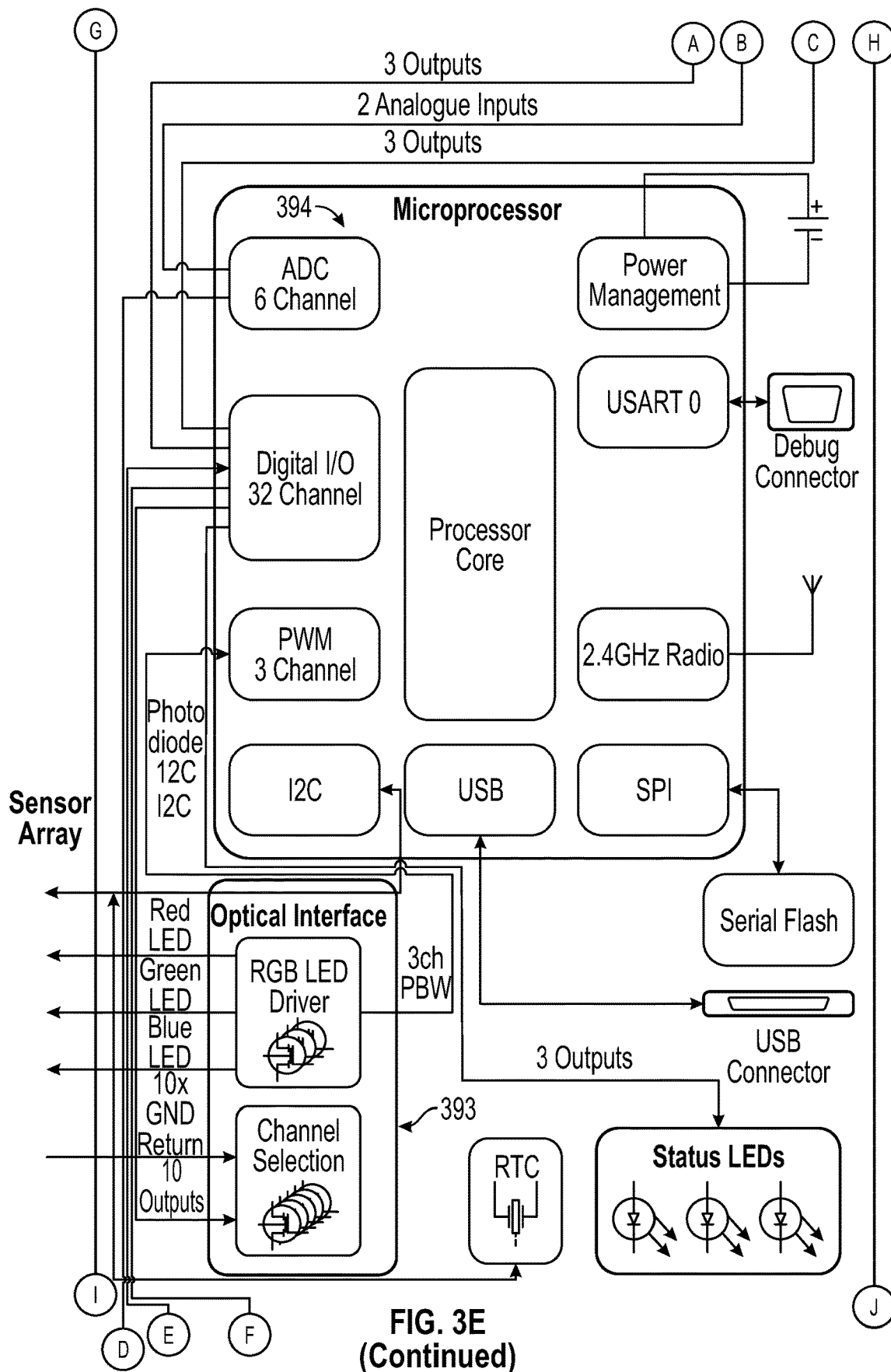
Figure 3E:
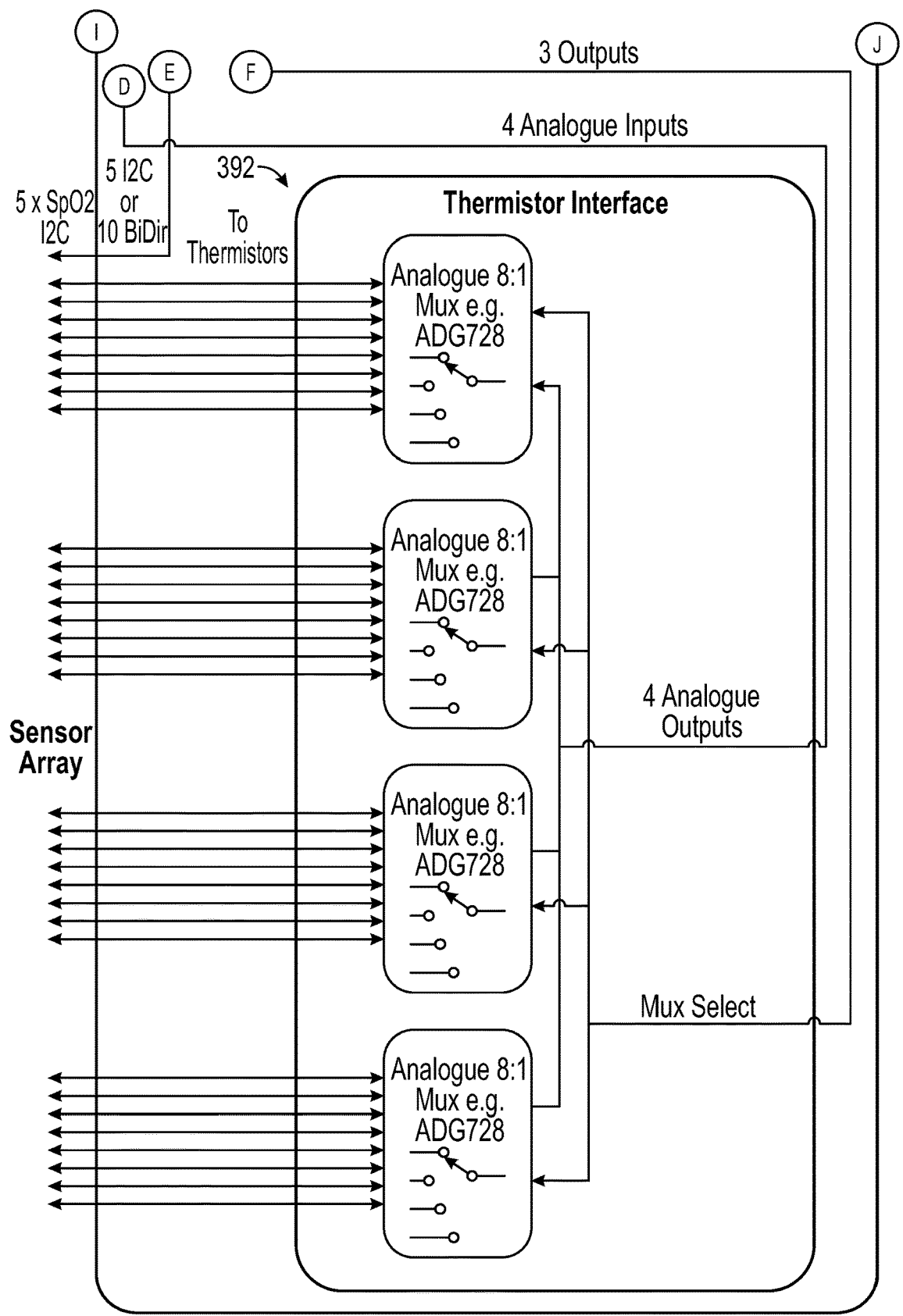

OPTIONAL FEATURES FOR CONTROL MODULE 7 day operation from a single set of batteries
28 day local, non-volatile, storage capacity
Easy to charge, or to replace battery
Wireless link to PC/tablet (such as Bluetooth)
Wired link to PC (optional, micro-USB)
Drive electronics for thermistors
Drive electronics for conductivity sensors
Drive electronics for optical sensors
Drive electronics for SpO2 sensors
Power management
Real Time Clock (RTC) to allow accurate data logging, and correlation with other measurands
Ability to change sample rates and intervals (useful for SpO2) for each sensor
Indication of status via LED, such as
(Green: Awake; Flashing green: Charging;
Blue: Wireless link established; Flashing blue: Wireless data transfer;
Yellow: Wired link established; Flashing yellow: Wired data transfer;
Red: Battery low; Flashing red: Battery very low FIG. 3E illustrates a block diagram 330 of a control module according to some embodiments. The block diagram of the control module includes a conductivity driver box 391 displaying features of the conductivity driver. Box 392 shows the features of the thermistor interface and box 393 shows the features of the optical interface. The control module can include a controller or microprocessor with features similar to those shown in box 394. Real time clock (RTC), Status LEDs, USB connector, Serial Flash, and Debug Connector can be included as features of the control module as shown in FIG. 3E.

In some embodiments, the microprocessor can have one or more of the following features: 2.4 GHz or another suitable frequency radio (either integrated, or external); Supplied Bluetooth software stack; SPI interface; USB (or UART for external USB driver); I2C; 3 channel PWM; 32 GPIO; or 6-channel ADC. In some embodiments, the device can require at least 48 I/O pins or possibly more due to banking limitations. Bluetooth stack typically requires ~20 kB on-board Flash, so a minimum of 32 kB can be required. In some embodiment, 64 kB can be required if complex data processing is considered. The processor core can be ARM Cortex M4 or a similar processor core. In some embodiments, the parts can include ST's STM32L433LC or STM32F302R8, which would require an external radio, or NXP's Kinetis KW range including integrated radio.

In some embodiment, the control module can include a memory component where the amount of local storage depends on the sample rate and resolution of the sensors. For example, an estimated data requirement of 256 Mb (32 MB) can be met by using a serial Flash device from a number of manufacturers (Micron, Spansion).

The control module can utilize one or more analogue switches. In some embodiments, analogue switches with good on resistance and reasonable bandwidth can be used. For example, Analog Devices' ADG72 or NXP's NX3L4051HR can be used. Based on the initial system architecture, 8 of these will be required.

The control module can incorporate a power source, such as a battery. For example a 300 mWh/day battery can be used. For 7 days this is 2100 mWh. This could be provided by: a 10 days, non-rechargeable, ER14250 (14.5 mm diameter×25 mm) LiSOCl$_2$ cell; or a 7 days, rechargeable, Li 14500 (14.5 mm diameter×500 mm) Li-Ion.

The control module can incorporate a real time clock (RTC). The RTC can be chosen from any RTC devices with crystal. The control module can also include miscellaneous resistors, capacitors, connectors, charge controllers, and other power supplies.

The PCB of the control module can be a 4-layer board, approximately 50 mm×20 mm, or 25 mm×40 mm. The type of PCB used can be largely driven by connection requirements to sensor array.

The enclosure of the control module can be a two part moulding, with clip features to allow easy access for changing sensor arrays or batteries.

The data collected through the sensor array can be passed through the control module and processed by host software. The software may be executed on a processing device. The processing device can be a PC, tablet, smartphone, or other computer capable of running host software. The processing device executing the software can be in communication with the control module through electrical wires or through wireless communication. In some embodiments, the software may be configured to provide access to the data held on the control module, but not to perform big-data analysis. The host software can include an interface to the control module via Bluetooth or USB. In some embodiments, the host software can read the status of control module, download logged data from control module, upload sample rate control to control module, convert data from control module into format suitable for processing by big-data analysis engine, or upload data to cloud for processing by analysis engine.

The software may be developed for PC (Windows/Linux), tablet or smartphone (Android/iOS), or for multiple platforms.

In some embodiments, a source of negative pressure (such as a pump) and some or all other components of the topical negative pressure system, such as power source(s), sensor(s), connector(s), user interface component(s) (such as button(s), switch(es), speaker(s), screen(s), etc.) and the like, can be integral with the wound dressing. In some embodiments, the components can be integrated below, within, on top of, or adjacent to the backing layer. In some embodiments, the wound dressing can include a second cover layer or a second filter layer for positioning over the layers of the wound dressing and any of the integrated components. The second cover layer can be the upper most layer of the dressing or can be a separate envelope that enclosed the integrated components of the topical negative pressure system.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

Wound Therapy and/or Treatment System

FIGS. 4A-4B illustrate an example wound therapy and/or treatment system 400. As illustrated, the system 400 includes a compression apparatus 402, a processor 404, and a one or more sensors 416. In some cases, the system 400 can be configured to increase a patient's blood circulation, prevent and/or treat ulcers, prevent blood clots, or aid a patient in avoiding ulceration (for example, in patients with venous insufficiency), among other things.

The compression apparatus 402 can be configured to provide compression to a patient, such as on a patient's calf, forearm, thigh, torso, chest, hand, foot, neck, head, ankle, or the like. For example, the compression apparatus 402 can include various pumps or compression components, including but not limited to, an intermittent pneumatic compression (IPC) device (non-limiting examples: a calf muscle pump (or calf pump), a forearm pump, a thigh pump, a torso pump, or other inflatable auxiliary sleeves, gloves or boots) or a passive compression component (non-limiting examples: compression bandaging, compression hosiery, compression wraps, or other compression sleeves).

In some embodiments, the compression apparatus 402 can be configured to trigger muscle activity. In the illustrated example, the compression apparatus 402 triggers calf muscle activity. However, in some cases, the compression apparatus can trigger forearm, thigh, torso, chest, hand, foot, neck, head, ankle, other muscle activity.

The one or more sensors 406 can include, but are not limited to, one or more of an electrical simulator (for example, as an electrode or an electrical probe), a motion detector (for example, an accelerometer, an electromyography (EMG) detector, a magnetometer or a gyroscope), a pressure sensor, temperature sensor (for example, a thermistor), an oxygen saturation (SpO2) sensor, a tissue color sensor (for example, an optical sensor), a pH sensor (for example, a sensor configured to measure a color of a pH sensitive pad), a simple-or-complex conductivity sensor, or a combination thereof.

The sensors 406 can include pads configured to adhere to skin or the wound over a thin layer of gel/paste. Alternatively, because sticking a sensor 406 to or removing an electrical stimulator from the wound site may cause the patient discomfort, one or more electrical stimulators can be supported by a wound dressing or otherwise not fixed to the wound dressing. For example, in some embodiments, the system 400 can include a wound dressing, such as wound dressing 100 or 155, that is configured to be positioned in contact with a wound of the patient and configured to support at least some of the sensors 406, the processor 404, or the compression apparatus 402.

As an example, the sensors 406 can include an electrical stimulator. The electrical stimulator can be configured to apply electrical stimulation to a patient and can include one or more electrodes.

As another example, the sensors 406 can include motion detector configured to detect movement of a patient. The motion detector can include at least one of an accelerometer, an electromyography (EMG) sensor or detector, a magnetometer, or a gyroscope.

The processor 404 can be in communication with and/or coupled to the compression apparatus 402. For example, as described in more detail below, the processor 404 determine a nerve or stimulation response based on a response detected due to muscle activity triggered by the compression apparatus 402. As a non-limiting example, the processor 404 can determine a nerve or stimulation response based on a response detected due to calf muscle activity triggered by the compression apparatus 402.

Furthermore, in some embodiments, the processor 402 can activate, deactivate, pause or start the compression apparatus 402. For example, the processor 402 can activate or deactivate the compression apparatus 402 based at least in part on a determination that the nerve response does not satisfy a response threshold. In some embodiments, the processor 404 is configured to activate the compression apparatus 402 based at least in part on a determination that patient movement detected by the motion detector satisfies a patient movement threshold.

The processor 404 can adjust the amount of muscle activity triggered by the compression apparatus 402. For example, the processor 404 can adjust how much compression the compression apparatus 402 applies to a patient's muscle. In some cases, the processor 404 can adjust the amount of muscle activity triggered by the compression apparatus 402 based at least in part on a determination that at least one of the nerve response does not satisfy a response threshold or patient movement detected by the motion detector satisfies a patient movement threshold.

Furthermore, the processor 404 can be in communication with and/or coupled to the one or more or sensors 406. In some cases, the processor can control the one or more sensors 406. For example, the processor 404 can cause the one or more sensors to activate, detect, turn on, turn off, activate, take a measurement, calibrate, send or receive data, or a combination thereof. In some cases, as described below, the processor 404 can utilize data from the one or more sensors 406 to determine one or more characteristics associated with the wound 408.

The processor 404 can be configured to operate or activate one or more sensors 406, such as an electrical stimulator. In some embodiments, the processor 404 is configured to activate one or more sensors 406 based at least in part on a determination that patient movement detected by the motion detector satisfies a patient movement threshold. In addition or alternatively, the processor 404 is configured to activate one or more sensors 406 based at least in part on a determination that an amount of muscle activity satisfies a threshold muscle activity.

In some embodiments, the processor 404 can adjust settings of one or more sensors 406. As a non-limiting example, the processor 404 can be configured to adjust an electrical stimulation applied by an electrical stimulator. For example, in some embodiments, the processor 404 can be configured to adjust an electrical stimulation based at least in part on at least one of a stimulation response or the patient movement. As another example, in some embodiments, the processor 404 can adjust the amount of muscle activity triggered by the electrical stimulation applied by the electrical stimulator. For example, the processor 404 can adjust the strength of the electrical stimulation applied to a patient's muscle. In some cases, the processor 404 can adjust the amount of muscle activity triggered by the electrical stimulation applied by the electrical stimulator based at least in part on a determination that at least one of the nerve response does not satisfy a response threshold or patient movement detected by the motion detector satisfies a patient movement threshold.

Furthermore, processor 404 can be configured to determine one or more wound characteristics based at least in part on at least one of the applied electrical stimulation or the stimulation response. Furthermore, processor 404 can be configured to provide an indication of the one or more wound characteristics.

In some embodiments, the processor 404 can receive sensor data from the one or more sensors 816. Using the sensor data or calculations from the sensor data, the processor 404 may evaluate a patient and/or a patient's wound. For example, can determine information related to the wound 408, the area surrounding the wound, or nerves or muscles associated with the wound 408. Furthermore, the processor 404 can determine information regarding the healing of the wound 408 (non-limiting example: an actual or estimated rate of healing, a heal status, a stage of the healing process of the wound), whether nerve damage is present, how the wound has healed over time, or whether damaged nerves are responding to treatment, etc. In some cases, the processor 404 can determine patient physiological information and/or information reflecting a pain experienced by a patient.

Calibrating Sensors

Difficulty in using electrical stimulation can arise when considering the placement of the electrical stimulator(s). For example, the accuracy in positioning an electrical stimulator over a nerve, muscle, or other location may be important to the level of voltage required to trigger muscle contraction. As another example, the thickness of tissue or fat over a nerve (for example, the thickness of fat behind the knee), muscle, or other location can also affect a required to contract a muscle. Furthermore, movement by the patient may cause skin to slide over the muscle, thereby changing the placement of the electrical stimulator and, consequently, altering the response.

While a higher voltage/stimulation could be utilized to trigger muscle contraction, a using a higher voltage increases the chance of the electrical impulse itself being painful to a patient. Additionally, if a large electrical impulse is used to overcome imperfect placement or thick fat, a patient may respond to the stimulation with movement (for example, it is painful for the patient). The movement can cause the skin to slide, thereby potentially altering the location of the electrical stimulator to an area where fat thins or the placement improves, resulting in a electrical stimulation that may be large and potentially painful.

In some embodiments, imperfect placement of electrical stimulators, varying thickness of body fat, patient movement, or electrical stimulator movement can be overcome by mounting the electrical stimulators as an array. For example, during treatment, such as during a calibration mode, the system 400 can activate one or more electrical stimulators in turn and determine which electrical stimulator returns a satisfactory or threshold response. In some cases, the satisfactory response may be the greatest response (for example, a response that causes the greatest muscle contraction). The satisfactory response may be any response within a response range, for example, fitting between a high threshold and a low threshold. In some cases, the satisfactory responses may be those that satisfy one or more stimulation response thresholds.

Each sensor may be calibrated (for example, tested in turn) and the sensor(s) identifying a satisfactory response is identified. Testing a sensor may include utilizing multiple electrodes for each of these two. For instance, a first electrical stimulator corresponding to a sensor at an end of a sensor array can be tested first (for example, the system 400 can cause the one sensor to transmit an electrical impulse and another sensor to monitor the response). Next, the electrical stimulator beside the first electrical stimulator can be tested second, and so on. In some instances, each electrical stimulator is tested in turn but in no particular order. In some embodiments, not all electrical stimulators are tested. For instance, one or more electrical stimulators can be tested until an acceptable (for example, satisfactory) response is received and the electrical stimulator which causes the acceptable response can be identified. In some cases, more than one electrical stimulator can be selected and used. For example, the two or three electrical stimulators that cause the most acceptable response may be identified and utilized.

Calibration of the sensors can be used to overcome imperfect placement and can be completed one time (for example, at the beginning of therapy) or periodically. For example, calibration can be performed at predefined intervals or in response to other factors, such as patient movement, electrical stimulator movement, expiration of a time interval, etc. Accordingly, electrical stimulator calibration allows for the imperfect placement of a compression apparatus 402, wound dressing or electrical stimulators, easing the human factors and minimizing the likelihood of poor response due to incorrect use.

In some cases, the system 400 may be able to predict which electrical stimulator(s) to use based on data received from one or more sensors. For example, where an accelerometer is included, the position of the limb or move of the patient can be identified so that an electrical stimulator can be chosen. By predicting which electrical stimulator(s) to use based on sensor data, the system 400 may advantageously avoid the necessity of testing all the electrical stimulators.

The system 400 may not be able to accurately predict which electrical stimulators to use based on the sensor data alone. However, in some cases, the system 400 can determine which electrical stimulators not to use and/or determine a group of electrical stimulators that should be tested. In some instances, once an electrical stimulator is selected, a calibration process will occur only if an unacceptable response is subsequently received.

For example, an accelerometer may indicate that the patient is lying down, and therefore may choose to operate a compression apparatus 402 or activate electrical stimulation in order to keep the blood from pooling in the patient's calf. However, if the patient's calf is raised, then the calf pump is not necessary, as blood will not pool. Thus, based on a stimulation response, the device can adjust compression or electrical stimulation (for example, pause stimulation until it is required again).

As a non-limiting example, some sensors may not be affected by patient movement. For example, a sensor 406 positioned on the side of the knee may be difficult to place initially, but will not be affected much during leg movement. However, a sensor 406 positioned on the back of the knee will tend to slide with leg movement. As such, while initial calibration may be required with both, ongoing calibration may only be required with one end and therefore not require as many test paths.

Adjusting Electrical Stimulation

Imperfect placement of electrical stimulators, varying thickness of body fat, patient movement, or electrical stimulator movement may be overcome by adjusting an electrical impulse. In some cases, imperfect placement refers to the position of the sensor 406 (for example, an electrical stimulator) relative a desired muscle or nerve (for example, a peroneal nerve). During treatment, such as during a calibration mode, the system 400 can activate an electrical stimulator at a first intensity level and monitor the response. If the response is unsatisfactory (for example, if the desired muscle or nerve is not stimulation), then the system 400 can adjust the intensity to another intensity level (for example, by adjusting the voltage, current, pulse rate frequency, waveform, duty cycle, etc.), activate the electrical stimulator, and monitor the new response. The system 400 can continue this process until a satisfactory response has been received, at which point, the system 400 can identify the appropriate intensity level. The measurement or recording of the response can verify that the device has had the correct response on the patient.

The first intensity level can be a relatively low intensity level and subsequent intensity levels can be larger (for example, increased by a predetermined amount.) Advantageously, by starting at a low intensity level, the system 400 can reduce the chance of the electrical impulse itself being painful to a patient. It should be noted, however, that in some embodiments, the first intensity level can be any intensity level such as the highest intensity level, the middle intensity level, an intensity level based on a past intensity level, etc. In some embodiments, a single electrical stimulator is configured to adjust in intensity. In other embodiments, the system 400 includes a plurality of electrical stimulators configured to transmit electrical impulses at different intensities and the system 400 can selectively activate the different electrical stimulators, for example, based on a desired intensity.

Adjustment of electrical stimulation intensity can be completed a single time (for example, at the beginning of therapy) or periodically. For example, this technique can be performed at predefined intervals or in response to other factors, such as patient movement, electrical stimulator movement, expiration of a time interval, etc. Accordingly, this technique allows for the imperfect placement of a compression apparatus 402, wound dressing or electrical stimulators, easing the human factors and minimizing the likelihood of poor response due to incorrect use.

Motion Sensor

In some cases, the processor 404 can utilize sensor data to correct or compensate for various difficulties such as, but not limited to, imperfect placement of sensors 406 (for example, electrical stimulators), varying thickness of body fat, patient movement, or electrical stimulator movement.

For example, the one or more sensors 406 can include a motion detector, such as accelerometer, or other sensor, such as an electromyography (EMG) sensor or detector, a magnetometer or a gyroscope. The motion detector(s) can be included in a wound dressing or compression apparatus 402. In addition or alternatively, the motion detector(s) can be attached to an extremity of a patient such as an arm or leg. In some instances, the motion detector is attached within close proximity to a wound such that movement (such as elevation, walking, bending, etc.) at or near the wound can be monitored.

The motion detector can detect if the patient is moving or can determine how a patient is moving (for example, standing, sitting, walking, running, raising or bending a limb, bending over, twisting, shaking, lying down, etc.). For example, when a patient is moving his foot, the movement of the patient's foot is itself a calf pump. Thus, blood flow increases through the veins of the patient, thereby reducing a need for compression (for example, from a compression apparatus 402) or muscle stimulation (for example, from an electrical stimulator). Accordingly, if a patient is moving (as identified by the motion detector), the system 400 may not need to trigger compression or muscle stimulation because the work is already being done (for example, blood flow is already increasing). Thus, by reducing or pausing therapy, the system 400 can reduce battery usage and increase the life of the device, as well as avoid providing electrical stimulation while the patient is moving.

Additionally, as the patient moves, the device can identify whether the electrical stimulators are causing an increased/decreased stimulation response. The device can then employ one or more techniques as described herein to re-optimize (for example, calibrate) the electrical stimulation, thereby minimizing the chance of the electrical impulse itself being painful to the patient.

In addition or alternatively, the device may have access to one or more stored moving profiles, from which the device may retrieve electrical stimulator settings. For instance, the device (for example, the motion detector) may determine the patient is walking and can identify the optimum electrical stimulator setting for the particular user from the stored profile. In some instances, the stored moving profile can include parameters corresponding to standing, sitting, walking, running, raising or bending a limb, bending over, twisting, shaking, or lying down. The device can then employ one or more techniques as described herein to change the transmitted electrical impulse to one that will give the correct response. A feedback loop can then further optimize.

In cases where a compression apparatus 402 or electrical stimulation device is used while the patient is moving (e.g. walking), the device may operate in parallel with the steps (or other movement) so the muscle trigger is in the same direction as that caused by the moving motion. For example, the system 400 can identify a walking pace of the patient and apply the muscle trigger at a time corresponding to when a patient's foot is on the walking surface (or when a patient's foot is off the walking surface.) This means that the user will not have conflicting muscular operation, which can minimize pain or annoyance caused by the device.

Electrical stimulation may be utilized to generate blood flow around the wound. However, because patient movement (for example, walking, standing, running, raising a limb, bending over, twisting, bending an arm or leg, etc.) can also increase blood flow around the wound, in some instances, when the monitored movement satisfies a movement threshold, the electrical stimulation may be turned off or paused. This is because the patient's movement is already effectuating blood flow around the wound. By not applying electrical stimulation, battery usage can be minimized and the life of the device can be increased. Alternatively, in some embodiments, electrical stimulation is applied despite satisfaction of a movement threshold. For instance, satisfaction of a movement threshold can cause the process to adjust one or more parameters of the electrical stimulation, such as reduced intensity of the electrical stimulation.

In some embodiments, the system 400 can determine whether a satisfactory amount of blood is flowing through a location of interest, and, based on that determination, can determine whether to apply electrical stimulation. For example, the system 400 may identify a satisfactory blood flow using one or more of a color sensor, a charged coupling device (CCD) video-camera, or the like in the location of interest, which may include the wound periphery.

In some embodiments, one or more other sensors 406 such as an electromyography (EMG) sensor or detector, magnetometer or gyroscope may be used in place of or in addition to an accelerometer. For instance, the system 400 can suitably arbitrate between characteristics determined using multiple monitoring techniques. In certain embodiments, the system 400 can execute one of the techniques, such utilizing an accelerometer incorporated into the wound dressing, and utilize one or more other techniques as needed. In various embodiments, the process can utilize one or more other techniques in cases the determined movement is perceived to be inaccurate or unreliable. In some embodiments, the sensor 406 includes one or more electrical stimulators, such as one or more electrical stimulators described herein.

Identify a Nerve or Stimulation Response

Figure 5:
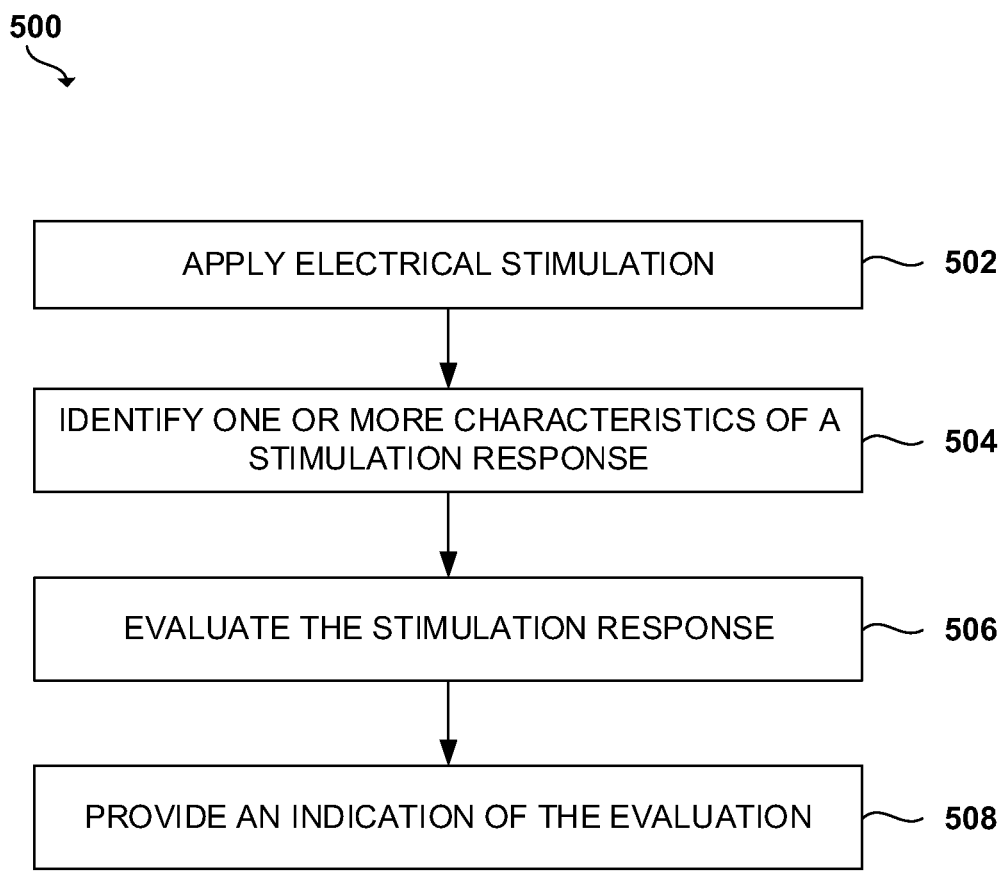
FIG. 5 illustrates a flow diagram of a process for evaluating a stimulation response to electrical stimulation according to some embodiments.

FIG. 5 is a flow diagram illustrative of an embodiment of a routine 500 for identifying a nerve or stimulation response to electrical stimulation. One skilled in the relevant art will appreciate that the elements outlined for routine 500 can be implemented by a system (such as the systems 102 or 400), one or more computing devices or components that are associated with a system (non-limiting examples: compression apparatus 402, the control module illustrated in FIG. 31 or processor 404), or the like. For ease of reference, routine 500 has been logically associated as being generally performed by system 400. However, the following illustrative embodiment should not be construed as limiting.

At block 502, one or more sensors 406 apply electrical stimulation to a patient. For example, as described herein, one or more of the sensors 406 can include one or more electrical stimulators, such as an electrode, or a plurality of electrical stimulators, such as an electrical stimulator array.

The electrical stimulation can be applied at or near a wound 408 or periwound, at or near one or more nerves, at or near one or more muscles, or the like. For example, the electrical stimulator(s) can apply electrical stimulation a wound, such as the middle of the wound or an edge or the wound, the intact skin surrounding the wound, or on the skin in direct or indirectly proximity to the muscles or nerves to be stimulated.

The one or more electrical stimulators can be positioned on, at, or near a wound 408, a periwound, a muscle or a nerve. For example, the electrical stimulators can be positioned or attached directly to the skin or wound of the patient. As another example, an electrical stimulator can be supported by or incorporated into a wound dressing such as an absorbent layer or spacer layer described herein. In some embodiments, the wound dressing can be larger than the size of the wound to cover the entire surface area of the wound as well as the surrounding intact skin. The larger size of the wound dressing can allow for more electrical stimulators or more spaced-apart electrical stimulators, thereby providing a broader range of electrical stimulation than if the electrical stimulators were placed in the center of the wound or only in another area.

The electrical stimulation can include a plurality of electrical impulses. The electrical impulses can include an electrical current such as direct current (DC), alternating current (AC), or pulsed current. Pulsed current can be delivered in either monophasic- or biphasic-pulsed waveforms, whereby current is delivered by the sensors at a certain frequency or via a number of pulses per second (pps). In some cases, high-voltage monophasic-pulsed current, low-voltage monophasic-pulsed current or low-voltage biphasic-pulse current can be employed.

The voltage associated with the electrical impulses can vary across embodiments. For example, the voltage can depend on the frequency of the signal, the overall RMS value, or whether AC or DC is used. For example, the voltage may fall within a range of voltages, such as any voltage between about 1V to about 100V RMS. Likewise, the frequency of the electrical impulses can vary across embodiments. For example, the frequency may fall within a range of frequencies, such as about 1 Hz to about 10 Hz or about 0.1 Hz to about 100 Hz. Furthermore, the current associated with the electrical impulses can vary across embodiments. For example, the current may fall within a range of current, such as about 10 microamps to about 500 microamps or less than about 100 microamps. However, it should be noted that any suitable voltage, frequency, current, waveform, duty cycle, etc. can be utilized.

At block 504, the system 400 can identify one or more characteristics of a stimulation response to the electrical stimulation or a response to compression. The characteristics can include can include any measurable response to the electrical stimulation by the patient including, but not limited to, such as muscle activity, the neural or muscular function at or near a wound, muscle contraction, movement by the patient, a color absorption characteristic, a reactive electrical signal in the muscle itself, a pain experienced by the patient, or other physiological responses.

For example, the electrical impulses generated by the electrical stimulator can mimic action potential (also called a nerve impulse) coming from the central nervous system. The electrical impulses can travel down a nerve, through a nerve/muscle junction and into a muscle. The electrical impulse(s) can spread throughout a muscle and cause or elicit contraction of the muscle fibers (sometimes referred to as muscle contraction).

In some cases, the controller can identify or parameterize muscle contraction associated with electrical stimulation. Electrical impulses can travel down a nerve pathway, and, in some cases, electrical stimulators can be placed along the way to detect a nerve conduction velocity or a strength of the nerve signal. Furthermore, the system 400 can determine a time it takes for the electrical impulse to travel from a stimulation site to a recording site, sometimes referred to as latency (which can be measured in milliseconds). The intensity of the response (sometimes referred to as the amplitude) can also be measured, for example in millivolts (mV). In some instances, electrical activity of muscles (non-limiting example: muscle contraction) and nerves can be measured using electromyography (EMG), where a small needle is inserted through the skin into the muscle and used to measure the electrical activity of the muscles. In contrast, a sensor 406 can be configured to measure the twitch caused by an electrical charge.

Furthermore, characteristics of the stimulation response can include an amount of movement by the patient that has been triggered by the electrical stimulation. As a non-limiting example, electrical stimulators may be positioned on the patient, such as on the back and/or outside of the patient's knee. The electrical stimulators may apply electrical stimulation, such as a short pulse, to a nerve, such as the peroneal nerve. Under normal conditions in which a healthy peroneal nerve is stimulation, the effect of triggering the nerve is a twitch of the foot. This may be due to operation of the muscles in the lower leg. The physical effects include a 'foot pump' (for example, the movement of the foot in an up-down motion relative to the lower leg) and a 'calf pump' (for example, the outside of the calf moves outwards, the inside moves inwards and the skin on the back of the calf raises and moves backwards slightly). Accordingly, in some embodiments, the system may utilize a motion detector such as an accelerometer to identify a patient's movement in response to the electrical stimulation.

Moreover, in some cases, characteristics of the stimulation response a flush of blood (for example, color absorption), a reactive electrical signal in the muscle itself, or other physiological responses.

At block 506, the system 400 can evaluate the stimulation response based on the characteristics of the stimulation response. For example, based on the characteristics of the stimulation response, the system 400 can determine if or where nerve damage is present or if or how damaged nerves are responding to treatment.

In some cases, the processor 404 can identify characteristics of a wound or peri-wound based on one or more of a speed, a strength, a latency, or an amplitude associated with the electrical stimulation. For example, speed can refer to a nerve conduction velocity, strength or amplitude can refer to a stimulation power, level or intensity, and latency can refer to the time it takes for the electrical impulse to travel from the stimulation site to the measuring site. In some cases, the processor 404 can receive data from the one or more sensors and determine the characteristics. As a non-limiting example, nerve conduction velocity electrical signals can travel faster and can be stronger in healthy nerves than in damages nerves. For example, in healthy nerves, nerve conduction velocity electrical signals can travel at up to 120 miles per hour. If the nerve is damaged, however, the signal may be slower and weaker. Accordingly, the system 400 can determine an extent of injury to a nerve or muscle based at least in part on a nerve conduction velocity or strength. Similar determinations can be made based on a distance between the different sensors, a position of the sensors, or a measured nerve conduction velocity, strength, latency, or amplitude.

Injuries or diseases that affect nerves and muscles can slow or halt the movement of these electrical signals. Accordingly, by measuring the electrical activity of muscles and nerves, the system can determine whether nerve damage is present or can determine whether damaged nerves are responding to treatment. For example, if the muscle or nerves are not healthy or not as healthy (for example, when they are wounded or otherwise injured), fewer or no muscle contractions result in response to the electrical stimulation. In some cases, the processor 404 can compare a value associated with the muscle contraction to one or more threshold muscle contraction values. In some cases, the one or more threshold muscle contraction values correspond to differing levels of wound health. For example, if the muscle responds to the electrical stimulation with a large muscle contraction (for example, satisfies a threshold muscle contraction), the controller can determine that the wound and/or muscle is healed or close to being healed. In contrast, if the muscle responds to the electrical stimulation with a small muscle contraction (for example, does not satisfy a threshold muscle contraction), the processor 404 can determine that the wound is not healed and/or can determine that the wound is not close to healing. In some cases, the muscle contraction thresholds can include a plurality of thresholds, each of which correspond to a differing degree of wound health. In some embodiments, the processor 404 can determine information reflecting a pain experienced by a patient.

The characteristics of the stimulation response can be used to identify whether the nerves underlying the wound are functioning, have regrown, etc. In contrast to traditional techniques that may require patient perception to identify nerve function and proliferation, some of the presently disclosed techniques determine wound characteristics based on the physics and chemistry of a patient's reflex. For example, some traditional techniques included a physician using a set of sprung cantilevers to identify nerve function and proliferation. Each of the sprung cantilevers would have are different strength, and the physician would use a sprung cantilever and ask the patient whether she perceived or felt the particular sprung cantilever. As such, by removing or limiting the requirement of the patient's perception of pain or feeling, the system advantageously includes a more empirical way of measuring or determining nerve function or proliferation.

In some embodiments, the system can determine one or more characteristics of a wound based at least in part on a pain response to a nerve stimulus. For example, a measured response to electrical stimulation may be used to detect tissue damage from the wound or from other factors such as neuropathy (for example, diabetes). In some instances, pain response could be used as an indicator to determine how the wound is healing due to changes in pain response. For example, one or more sensors (for example, a pressure sensor) can be used to measure the pain relationship or determine the existence or extent of a patient's pain.

As another example, the system 400 can evaluate the stimulation response based on a patient movement that is responsive to the electrical stimulation or the compression. For example, the one or more sensors 406 can include an accelerometer from which the system 400 can receive data indicative of patient movement. Based on sensor data, the system can determine whether a patient is moving. In some cases, the system 400 can determine a specific orientation of the patient (for example, lying down, standing up, etc.) or an orientation of a patient's limb (for example, arm raised, leg raised, etc.). In some embodiments, the system can determine how a patient is moving (for example, walking, running, standing, bending, climbing stairs, laying, sitting, etc.). In addition or alternatively, the system can utilize a motion detector to measure a patient's movement in response to the electrical stimulation. In some embodiments, little to no movement by the patient in response to the stimulation can indicate damaged nerves, because for example, it may indicate that the patient did not feel the stimulation. In contrast, detected movement can indicate healthy nerves.

At block 508, the system 400 can provide an indication of the evaluation, as described herein. The processor 404 can determine information regarding the healing of the wound 408 (non-limiting example: an actual or estimated rate of healing, a heal status, a stage of the healing process of the wound), whether nerve damage is present, how the wound has healed over time, or whether damaged nerves are responding to treatment, etc. For example, a healed wound may exhibit a different stimulation response than an unhealed wound. Similarly, a partially healed wound may exhibit a different stimulation response than either a healed wound or an unhealed wound. In some cases, the wound may heal over time, and each "stage" of wound healing (for example, slight progressions in healing) may exhibit a different stimulation response. For example, a wound that has not regrown its skin will not have the same nerve endings as wound dressing that has regrown its skin. Thus, the wounds would not respond to the stimulation in the same way. Accordingly, tissue regrowth may therefore be identified. For example, the skin may first protect deeper nerves from triggering (for example, exhibiting a stimulation response). Then, once the nerves regrow or heal, the wound may become sensitive again, thus exhibiting a response to stimulation.

In some embodiments, the system 400 can indicate a healing phase of the wound (for example, blood clotting (hemostasis), inflammation, tissue growth (proliferation) or tissue remodeling (maturation)). As another example, the system 400 can provide an indication of wound size (or reduction in wound size), wound healing rate (for example, predicted time remaining until wound is partially or fully healed), or percent healed (for example, 10, 20, 30, 40, 50, 60, 70, 80, 90, or 100% healed). As another example, the system 400 can provide an indication of healthy nerves or damaged nerves (for example, neuropathy). In some embodiments, the system 400 can indicate whether a patient has one or more diseases, such as diabetic neuropathy.

In some embodiments, the system 400 can record data associated with the monitored stimulation response or the evaluation. For instance, data such as the speed, strength, latency, and amplitude of the nerve response or the location of the electrical stimulators or the distance between electrical stimulators can be recorded. The system 400 can compare current aspects of the stimulation response with past stimulation response data and to determine if or how much progress (for example, healing) has occurred. In some embodiments, the system 400 can cause a display to display a map of areas of a wound, as described herein with respect to FIG. 8.

It will be understood that the various blocks described herein can be implemented in a variety of orders, and that the system 400 can implement one or more of the blocks concurrently and/or change the order, as desired. For example, the system 400 can concurrently apply the electrical stimulation and identify characteristics of a stimulation response. Similarly, the system 400 can concurrently determine a wound status, provide an indication of wound status, and/or adjust electrical stimulation. Furthermore, it will be understood that fewer, more, or different blocks can be used as part of the routine 500. For example, the routine 500 can omit any combination of blocks 502, 504, 506, or 508.

Electrical Stimulation Adjustment

Figure 6:
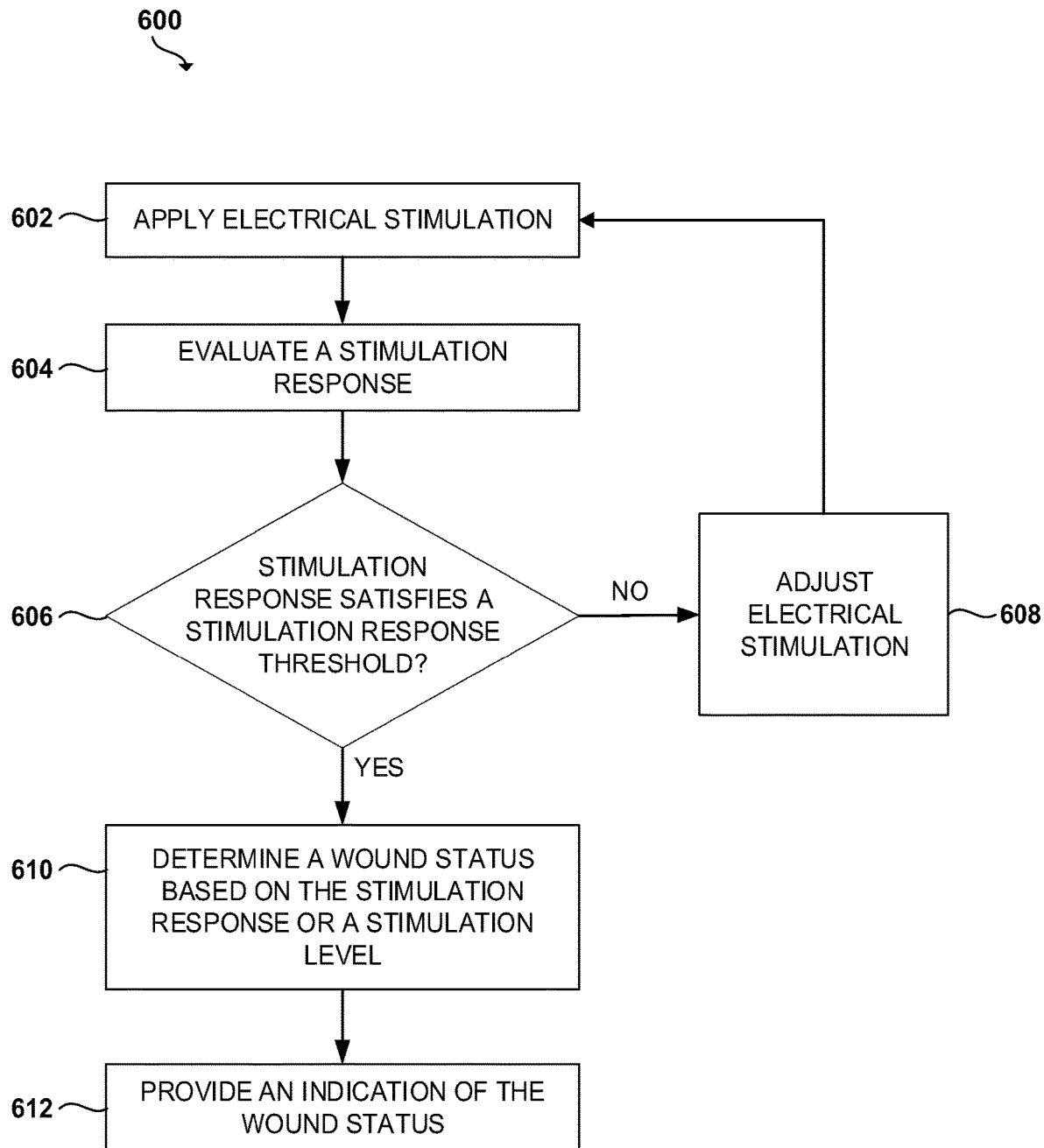
FIG. 6 illustrates a flow diagram of a process for evaluating a stimulation response to electrical stimulation and adjusting the electrical stimulation based at least in part on the stimulation response according to some embodiments.

FIG. 6 is a flow diagram illustrative of an embodiment of a routine 600 for evaluating a stimulation response to electrical stimulation and adjusting electrical stimulation based at least in part on the stimulation response. One skilled in the relevant art will appreciate that the elements outlined for routine 600 can be implemented by a system (such as the systems 102 or 400), one or more computing devices or components that are associated with a system (non-limiting examples: compression apparatus 402, the control module illustrated in FIG. 31 or processor 404), or the like. For ease of reference, routine 600 has been logically associated as being generally performed by processor 404. However, the following illustrative embodiment should not be construed as limiting.

At block 602, similar to block 502 of FIG. 5, the system 400 applies electrical stimulation. As described herein, the electrical stimulation can include a plurality of electrical impulses generated by electrical stimulators such as one or more electrical stimulators. In some embodiments, the system can include a plurality of electrical stimulators. One or more of the plurality of electrical stimulators can be configured to provide electrical impulses at an intensity (for example, voltage, current, pulse rate, etc.) different from another one of the plurality of electrical stimulators. In some embodiments, one or more of the plurality of electrical stimulators have an adjustable intensity. For instance any suitable, voltage, current, pulse rate (or frequency), waveform, duty cycle, etc. of stimulation can be utilized.

At block 604, similar to blocks 504 and 506 of FIG. 5, the system 400 can identify one or more characteristics of a stimulation response (non-limiting examples: such as a degree of muscle contraction, nerve conduction velocity, strength of the nerve signal, latency, or amplitude) and can evaluate the stimulation response.

At block 606, the system 400 determines whether one or more of the detected characteristics of the stimulation response satisfies one or more stimulation response thresholds. For example, the one or more thresholds can correspond to an acceptable level of muscle contraction, which may be a measurable muscle contraction or a muscle contraction having a certain intensity. Filtering out unacceptable muscle contractions can minimize variability, thereby improving outcomes. Thus, this step can verify that the stimulation caused correct response of the patient. In addition or alternatively, the one or more thresholds can correspond to an acceptable level of neural or muscular function at or near a wound, movement by the patient, a color absorption characteristic, a reactive electrical signal in the muscle itself, or other physiological responses.

In some embodiments, the one or more stimulation response thresholds can be determined by the system 400. For example, the one or more thresholds can be based at least in part on one or more of a patient's gender, age, ethnicity, race, or fitness level and/or based at least in part on one or more of the location, stage of healing, size, or shape of the wound. In some embodiments, the one or more of the thresholds can be higher or lower than acceptable muscle contractions, for example, to allow for variability during operation. In some embodiments, the one or more stimulation response thresholds include at least one of a muscle contraction threshold, nerve conduction velocity threshold, strength threshold, latency threshold, amplitude threshold, pain threshold, etc.

If the stimulation response does not satisfy (for example, is below or otherwise not substantially equal to) a stimulation response threshold, the system 400 transitions to block 608, where it adjusts the electrical stimulation. For example, the system 400 can cause one or more electrical stimulators to increase or decrease intensity of stimulation, such as voltage, current, or pulse rate, etc. Alternatively, or in addition, the system 400 can cause one or more electrical stimulators to turn ON or OFF. For example, a plurality of electrical stimulators can be mounted as an array, wherein at least some of the plurality of electrical stimulators can transmit at a similar or different voltage, current, or pulse rate. During treatment, the system 400 can try one or more different electrical stimulators until a response that satisfies the one or more stimulation response threshold is detected. In some embodiments, the system 400 will try each electrical stimulator in turn and identify the greatest response. Accordingly, by adjusting the intensity of the transmitted electrical impulse, the electrical stimulators do not need to placed or positioned in an exact location to cause an acceptable stimulation response. Advantageously, the likelihood of a poor response (such as one that does not satisfy a threshold) due to, for instance, incorrect use or placement of electrical stimulators is minimized. After the system 400 adjusts the electrical stimulation, the process transitions back to block 602, where electrical stimulation is applied.

In some embodiments where the process adjusts the intensity of the electrical stimulation, the system 400 can initially apply the electrical stimulation at a lower intensity (such as, relatively low voltage, current, frequency, etc.). By applying a relatively low intensity initially, the process can advantageously reduce the likelihood of the electric stimulation itself being painful to a patient. For example, because the placement of the one or more electrical stimulators can affect the response, an imperfect placement can cause the electrical stimulator to be positioned on or near a sensitive area of the patient's body. Accordingly, by applying a relatively low intensity and then slowly increasing the intensity until an acceptable response is detected, the likelihood of patient discomfort is diminished. It should be noted, however, that in some cases the system 400 may begin by transmitting relatively high or moderate intensity impulses.

If a characteristic of the stimulation response satisfies a stimulation response threshold (for example, the characteristic is substantially equal to or is above a stimulation response threshold), the system 400 can transition to block 610 where a wound status can be determined based at least in part on the stimulation response or the detected electrical impulse. For example, the wound status can be based at least in part on one or more characteristics of the stimulation response such as a degree of muscle contraction, nerve conduction velocity, strength of the nerve signal, latency, amplitude, degree of pain experienced by the patient, etc. Alternatively or in addition, the wound status can be based at least in part on one or more characteristics of the one or more electrical impulses that caused the current stimulation response. For instance, the one or more electrical impulses can include at least one of voltage, current, pulse rate, phase, a number of impulses, or a number of electrical stimulators utilized. In some instances, the wound status can additionally or alternatively be based at least in part on at least one of a distance between one or more electrical stimulators, a position, size, color, shape, stage of healing, etc. of the wound. In some instances, the wound status can alternatively or additionally be based at least in part on ethnicity, race, and/or fitness level.

At block 612, similar to block 508 of FIG. 5, the system 400 can provide an indication of the wound status determined at block 610. In some embodiments, the indication of wound status can include one or more of: at which stage of the healing phase the wound resides (for example, blood clotting (hemostasis), inflammation, tissue growth (proliferation) or tissue remodeling (maturation)); wound size or shape, including reduction in wound size; wound healing rate (for example, predicted time remaining until wound is partially or fully healed); percent healed (for example, 10, 20, 30, 40, 50, 60, 70, 80, 90, or 100% healed); a percentage of healthy nerves or damaged nerves (for example, degree of neuropathy); a projected recovery time; whether a patient has one or more diseases, such as diabetic neuropathy; or any other data which might be helpful in analyzing the wound or its healing process.

In some embodiments, the system 400 can provide an indication by causing one or more displays to display a representation of a wound, such as a map of one or more areas determined to have neuropathy or nerve growth. For example, the map can be similar to the map described herein. Additionally or alternatively, the indication can be provided audibly, tactually, etc.

It will be understood that the various blocks described herein can be implemented in a variety of orders, and that the system 400 can implement one or more of the blocks concurrently and/or change the order, as desired. For example, the system 400 can concurrently apply the electrical stimulation and identify characteristics of a stimulation response. Similarly, the system 400 can concurrently determine a wound status, provide an indication of wound status, and/or adjust electrical stimulation. Furthermore, it will be understood that fewer, more, or different blocks can be used as part of the routine 600. For example, the routine 600 can omit any combination of blocks 602, 604, 606, 608, 610, or 612.

Electrical Stimulation and Patient Movement

Figure 7:
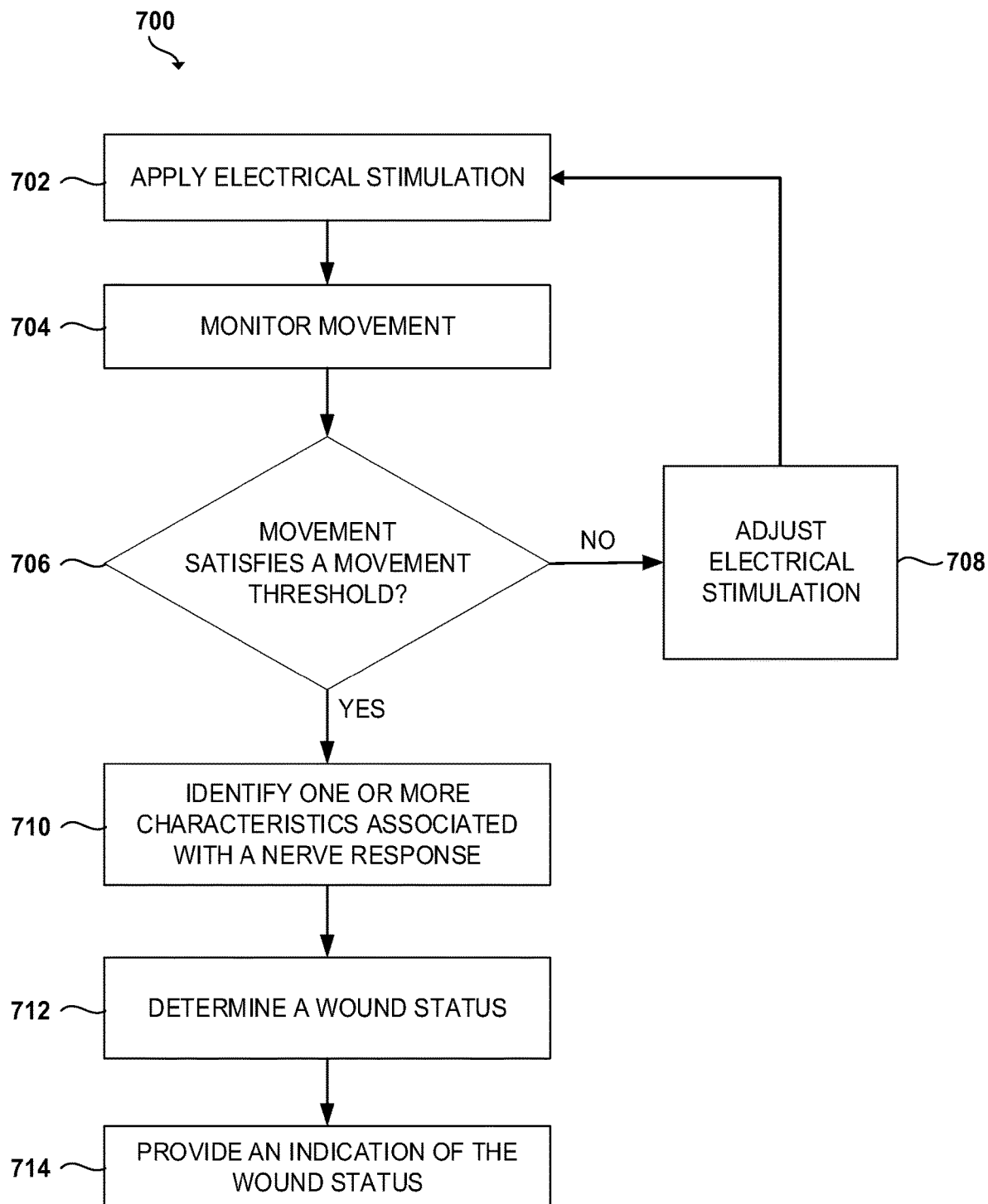
FIG. 7 illustrates a flow diagram of a process for controlling electrical stimulation based at least in part on the monitored patient movement according to some embodiments.

FIG. 7 is a flow diagram illustrative of an embodiment of a routine 700 for controlling electrical stimulation based at least in part on the monitored patient movement. One skilled in the relevant art will appreciate that the elements outlined for routine 700 can be implemented by a system (such as the systems 102 or 400), one or more computing devices or components that are associated with a system (non-limiting examples: compression apparatus 402, the control module illustrated in FIG. 31 or processor 404), or the like. For ease of reference, routine 700 has been logically associated as being generally performed by processor 404. However, the following illustrative embodiment should not be construed as limiting.

At block 702, similar to block 502 of FIG. 5 and block 602 of FIG. 6, the system 400 applies electrical stimulation.

At block 704, the system 400 monitors movement of the patient and/or one or more sensors 404. For example, the system 400 can utilize one or more of the movement monitoring techniques described herein, such as utilizing a motion sensor.

In some embodiments, the system 400 can suitably arbitrate between movement determined using multiple movement monitoring techniques. In certain embodiments, the system 400 can execute one of the techniques, such utilizing an accelerometer incorporated into the wound dressing, and utilize one or more other techniques as needed. In various embodiments, the system 400 can utilize one or more other techniques in cases the determined movement is perceived to be inaccurate or unreliable. In some embodiments, the sensor 406 includes one or more electrical stimulators, such as one or more electrodes described herein.

At block 706, the system 400 determines whether monitored patient or electrical stimulator movement meets or satisfies (for example, is substantially equal to or exceeds) one or more movement thresholds. For example, with respect to patient movement, a movement threshold can be satisfied if the system 400 determines that the patient is standing, walking, running, raising a limb, bending over, twisting, bending an arm or leg, etc. As another example, with respect to sensor 406 (such as, an electrical stimulator) movement, a movement threshold can be satisfied if the system 400 determines that the sensor 406 has shifted in the wound dressing, becomes unattached to a patient, or is otherwise displaced from an ideal or desired location relative to the wound.

If the monitored movement satisfies one or more movement thresholds, the system 400 transitions to block 708, where it adjusts the electrical stimulation, similar to block 608 of FIG. 6. For example, the system 400 can cause one or more electrical stimulators to increase or decrease intensity, such as voltage, current, or pulse rate, etc. Alternatively, or in addition, the system 400 can cause one or more electrical stimulators to turn ON or OFF. Accordingly, by adjusting the intensity of the transmitted electrical impulse, the system 400 can compensate for the detected movement and potential displacement of the electrical stimulators. Advantageously, the likelihood of a poor response (for example, one that does not satisfy a stimulation response threshold) due to, for instance, movement is minimized. After the system 400 adjusts the electrical stimulation, the process transitions back to block 702, where electrical stimulation is applied.

If the monitored movement does not satisfy (for example, is below or otherwise not substantially equal to) a movement threshold, the system 400 transitions to block 710, where one or more characteristics of the stimulation response can be detected, as described herein. In some embodiments, as describe with respect to FIG. 6, the system 400 can adjust the electrical stimulation based at least in part on whether one or more of the detected characteristics of the stimulation response satisfy (for example, is substantially equal to or exceeds) one or more stimulation response thresholds. In addition or alternatively, the process can continuously monitor patient or sensor movement and adjust the electrical stimulation accordingly. Thus, in some embodiments, the system 400 can verify that the electrical stimulators are applying an appropriate electrical impulse based at least in part on at least one of the detected response, the detected movement, the position of an electrical stimulator, or the location of the wound, etc.

If a characteristic of the stimulation response satisfies (for example, the characteristic is substantially equal to or is above a stimulation response threshold) the stimulation response threshold, the system 400 can transition to block 712, where a wound status is determined based at least in part on at least one of the stimulation response, the electrical impulse, or the monitored movement. For example, the wound status can be based at least in part on one or more characteristics of the stimulation response, such as a degree of muscle contraction, nerve conduction velocity, strength of the nerve signal, latency, amplitude, degree of pain experienced by the patient, etc. Alternatively or in addition, the wound status can be based at least in part on one or more characteristics of the one or more electrical impulses that caused the current stimulation response. For instance, the one or more electrical impulses can include voltage, current, pulse rate, phase, a number of impulses, or a number of electrical stimulators utilized. In some instances, the wound status can additionally or alternatively be based at least in part on a distance between one or more electrical stimulators, a position, size, color, shape, stage of healing, etc. of the wound. In some instances, the wound status can be based at least in part on ethnicity, race, or fitness level. Alternatively or in addition, the wound status can be based at least in part on the monitored movement. For example, the process may determine a position of the electrical stimulators on the patient's body based at least in part on the monitored movement.

At block 714, similar to block 612 of FIG. 6, the system 400 can provide an indication of the wound status.

It will be understood that the various blocks described herein can be implemented in a variety of orders, and that the system 400 can implement one or more of the blocks concurrently and/or change the order, as desired. For example, the system 400 can concurrently apply the electrical stimulation and identify characteristics of a stimulation response. Similarly, the system 400 can concurrently determine a wound status, provide an indication of wound status, and/or adjust electrical stimulation. Furthermore, it will be understood that fewer, more, or different blocks can be used as part of the routine 700. For example, the routine 700 can omit any combination of blocks 702, 704, 706, 708, 710, 712, or 714.

Mapping Nerve Growth

Based on sensor data, the system 400 can provide useful insights for identifying measurands that may indicate whether a wound is on a positive or negative healing trajectory. For example, by collecting and recording data corresponding to wounds that heal well, and from those that do not, the system can determined or project a healing rate of one or more regions of a wound. For example, a particular wound may include regions that heal more quickly or more slowly than other regions of the wound. Accordingly, in some embodiments, one or more areas of neuropathy or nerve growth can be mapped or charted to provide an indication of healing of the wound.

Figure 8:
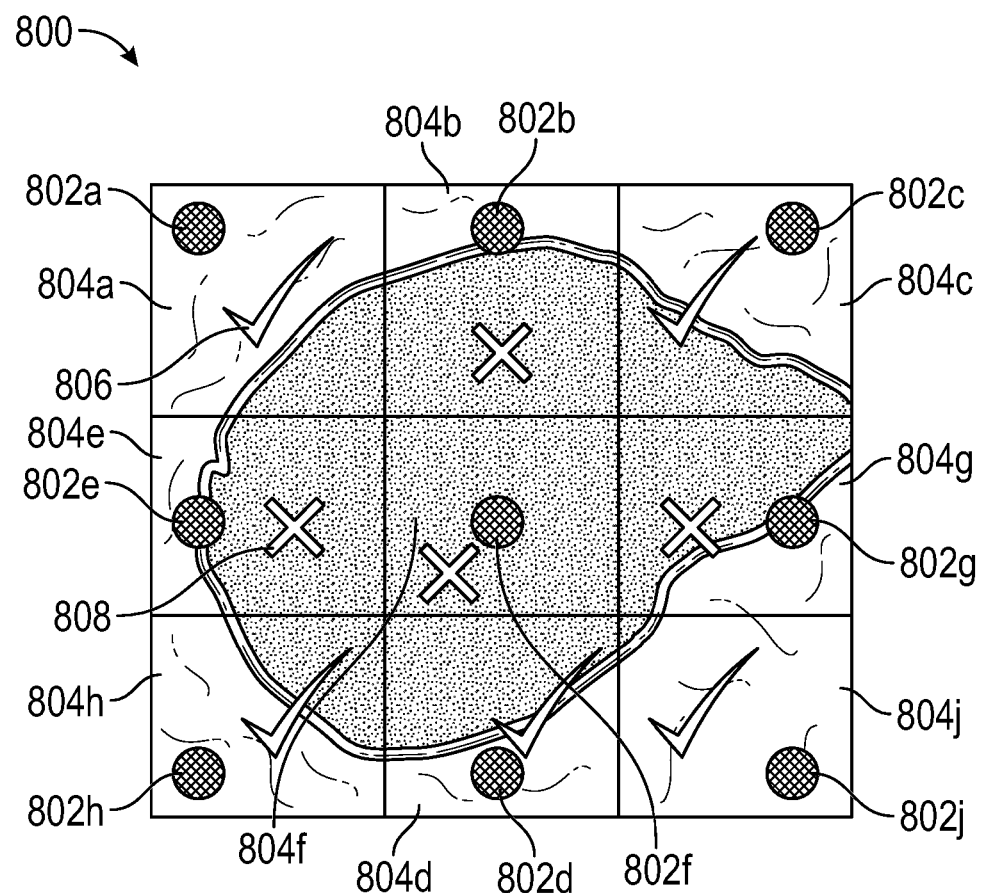
FIG. 8 illustrates an embodiment of a wound map corresponding to an example wound.

FIG. 8 illustrates an embodiment of a wound map 800 corresponding to an example wound. The wound map 800 includes an image of a wound and periwound that has be separated into a plurality of regions or areas.

As illustrated, the wound has separated the wound into nine areas 804*a*-I, where each of the areas corresponds to a single sensor 406. Using each sensor, the system can perform one of the techniques described herein and can determine whether a satisfactory (for example, threshold) stimulation response was received. In some cases, if a satisfactory response was received, the area(s) corresponding to the satisfactory stimulation response can receive a positive indication. In this example, the positive indication is a check 406. However, it will be understood that other indications can be utilized.

If a satisfactory response was not received, the area(s) corresponding to the electrical stimulator includes a negative indication. In this example, the negative indication is an "x" 408. However, it will be understood that other indication can be utilized.

In some embodiments, a map can be generated which corresponds to how the areas are healing over time (for example, whether the stimulation response has improved). In some implementations, the system can determine any suitable characteristics of the wound, which can likewise be depicted in a wound map. For example, a map can show whether nerve damage is present or damaged nerves are responding to treatment, the extent of injury to a nerve, etc. In some embodiments, the system can collect and record wound characteristic data and use a map to track how the wound has healed over time or a progress of the healing of the wound. The mapping and trend of these wound characteristics may identify a progress of nerve growth or neuropathy.

For example, one or more sensors (for example, electrodes) may apply electrical stimulation to one or more nerves in, on, or around the wound. In addition, one or more sensors (for example, electrodes) may identify a stimulation response to the applied electrical stimulation. Based at least in part on the applied electrical stimulation and/or the stimulation response, the system can identify characteristics of the wound, such as characteristics of nerves or muscles corresponding to the wound. For example, the system may be able to determine whether nerve damage exists (for example, the nerve is neuropathic) or may be able to determine how well a wound, or portions of a wound, is healing.

In some cases, the system 400 can determine a position of a sensor relative to a wound of a patient, and can further determine characteristics of the wound. For example, the system, via a sensor, can apply electrical stimulation to the patient and can identify a stimulation response. Based at least in part on the stimulation, the system can determine a position of the sensor. For example, where nerve response is normal (for example, corresponds to an expected stimulation response of healthy nerves, satisfies a normal threshold response, etc.), the system can determine that the electrical stimulator is likely to be on normal skin outside the wound area, rather than on the wound itself. As another example, when little or no stimulation response is elicited by the applied electrical stimulation, or when the stimulation response is deeper or farther away from the wound, the system can determine that the electrical stimulator is likely on the wound area, rather than on the skin around the wound area. Similarly, if a stimulation response is not normal (for example, does not corresponds to an expected stimulation response of a healthy nerve, does not satisfy a normal threshold response, etc.), the system can determine that the electrical stimulator is likely on the wound area, rather than on the skin around the wound area.

The system 400 can determine characteristics of the wound. For example, a wound that has not regrown its skin will have a different stimulation response than a wound that has regrown its skin because skin first protects the deep nerves from triggering a response. Then, once the nerves regrow through, the area becomes sensitive again. Thus, based on the stimulation response, the system may identify that an electrical stimulator is positioned on the wound, and may further identify an amount of healing (for example, a level of tissue regrowth).

The system may also determine a level of damage to a nerve based at least in part on the applied electrical stimulation and/or the stimulation response. For example, a first partially healed nerve may elicit a different response than a second partially healed nerve because the first nerve may be close to being fully healed. Accordingly, the system can apply electrical stimulation and, based at least in part on an identified stimulation response, the system can identify a level of damage to the nerve. For example, the system can determine a certain degree to which a nerve is damaged (for example, 20% damaged, 50%, damaged, 80% damaged, etc.).

Measurements of a response can be taken in various locations. For example, electrical stimulation can be applied to a nerve at or near a wound site, and the system can identify whether a corresponding muscle contraction occurred. Similarly, electrical stimulation can be applied to a nerve away from the wound site and the wound site can be monitored to identify an effect at the wound. Regardless of how the electrical stimulation is applied, the non-conduction of a twitch (for example, muscle contraction) may identify a compromised (and therefore unhealthy) nerve pathway.

In some cases, the system may determine whether one or more nerves (or portions of nerves) are damaged or neuropathic based at least in part on a determination that applied stimulation does not trigger a satisfactory response, such as expected twitching or contraction. Similarly, the system may determine that one or more nerves are healthy nerves based at least in part on a determination that applied stimulation triggers a satisfactory response. As described herein, a satisfactory response can be a response within a response range, for example, fitting between a high threshold and a low threshold.

It will be understood that although the wound map 800 of the illustrated embodiment of includes nine wound areas 804a-i, the wound and/or periwound can be separated into any suited number of areas. Moreover, in some embodiments, one or more areas can correspond to one or more sensors.

Furthermore, although an example map is illustrated in FIG. 8, the system can provide various outputs indicative of the characteristics of the wound. For example, the characteristics can be displayed, audibly produced, tactually produced, or the like Other Variations In some implementations, the area surrounding the protruding electronic components can be substantially filled with padding, such as by with flocking material, to substantially even out or smooth the wound-facing surface of the wound dressing. In some embodiments, non-woven material may be used to flock the area around the protrusions to prevent tissue ingrowth.

Any controller described herein can include features of any of the other described wound dressing embodiments. Further, any device, component, or module described in a certain embodiment can include features of any of the other described embodiments of the device, component, or module.

In some embodiments, one or more electronic components can be positioned on the side of a wound contact layer opposite the side that faces the wound. Systems and methods described herein are equally applicable to such wound contact layers. Any wound dressing embodiment described herein can include features of any of the other described wound dressing embodiments. Similarly, any controller described herein can include features of any of the other described wound dressing embodiments. Further, any device, component, or module described in a certain embodiment can include features of any of the other described embodiments of the device, component, or module.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A wound monitoring and/or therapy apparatus, comprising:
    an electrical stimulator configured to apply an electrical stimulation to a patient;
    a motion detector configured to detect a movement of the patient;
    a wound dressing configured to be positioned over a wound of the patient and configured to support the electrical stimulator; and
    one or more processors coupled to the electrical stimulator and the motion detector, the one or more processors configured to:
        operate the electrical stimulator to apply an electrical stimulation;
        adjust the electrical stimulation based at least in part on at least one of a stimulation response or the movement of the patient;
        determine one or more wound characteristics based at least in part on at least one of the electrical stimulation or the stimulation response, wherein determination of the one or more wound characteristics comprises determination of a nerve response in at least a portion of the wound; and
        provide an indication of the one or more wound characteristics.

2. The apparatus of claim 1, wherein the electrical stimulator is further configured to detect the stimulation response.

3. The apparatus of claim 1, wherein the stimulation response includes at least one of patient movement responsive to the electrical stimulation or an electrical signal that is reactive to the electrical stimulation.

4. The apparatus of claim 1, wherein the motion detector includes at least one of an accelerometer, an electromyography (EMG) detector, a magnetometer, or a gyroscope.

5. The apparatus of claim 1, wherein the electrical stimulator comprises a plurality of electrodes.

6. The apparatus of claim 5, wherein the plurality of electrodes are mounted on the wound dressing as an array.

7. The apparatus of claim 5, wherein the one or more processors are configured to operate each electrode in turn and identify which electrode causes the greatest muscle contraction.

8. The apparatus of claim 7, wherein the one or more processors are configured to determine the one or more wound characteristics based at least in part on the stimulation response to the electrical stimulation from the electrode identified as causing the greatest muscle contraction.

9. The apparatus of claim 1, wherein the one or more processors are configured to adjust the electrical stimulation based on a determination that the stimulation response does not satisfy a stimulation response threshold.

10. The apparatus of claim 1, wherein the one or more processors are further configured to determine one or more areas of neuropathy or nerve growth in at least the portion of the wound based at least in part on the one or more wound characteristics, and wherein the indication of the one or more wound characteristics comprises a visual map of the one or more areas of neuropathy or nerve growth.

11. The apparatus of claim 1, wherein the one or more wound characteristics include an indication of nerve health, and wherein the one or more processors are configured to provide the indication of the one or more wound characteristics by displaying a map corresponding to the nerve health.

12. A wound monitoring and/or therapy apparatus, comprising:
an electrical stimulator configured to apply an electrical stimulation to a patient;
a motion detector configured to detect a movement of the patient;
a wound dressing configured to be positioned over a wound of the patient and configured to support the electrical stimulator; and
one or more processors coupled to the electrical stimulator and the motion detector, the one or more processors configured to:
operate the electrical stimulator to apply an electrical stimulation;
adjust the electrical stimulation based at least in part on at least one of a stimulation response or the movement of the patient;
determine one or more wound characteristics based at least in part on at least one of the electrical stimulation or the stimulation response;
provide an indication of the one or more wound characteristics; and
reduce intensity of or pause the electrical stimulation responsive to the movement of the patient satisfying one or more movement thresholds.

13. A method for controlling a wound monitoring and/or therapy apparatus, the method comprising:
applying an electrical stimulation to a wound at a first stimulation level via an electrical stimulator supported by a wound dressing configured to be positioned in over the wound;
detecting a first stimulation response to the electrical stimulation at the first stimulation level;
based at least in part on determining that the first stimulation response does not satisfy a stimulation response threshold:
adjusting the electrical stimulation to a second stimulation level,
applying the electrical stimulation to the wound at the second stimulation level, and
detecting a second stimulation response to the electrical stimulation at the second stimulation level;
determining a wound status based at least in part on at least one of the first or second stimulation levels or the first or second stimulation responses, wherein determining the wound status comprises determining a nerve response in at least a portion of the wound based at least in part on at least one of the first or second stimulation levels or the first or second stimulation responses; and
providing an indication of the wound status,
wherein the method is performed under control of a controller of the apparatus.

14. The method of claim 13, further comprising:
monitoring a patient movement; and
responsive to the patient movement satisfying a movement threshold, adjusting the electrical stimulation to the second stimulation level.

15. The method of claim 13, wherein the wound status includes an indication of nerve health, and wherein providing the indication of the wound status includes displaying a map corresponding to the nerve health.

16. The method of claim 13, wherein the electrical stimulator includes a plurality of electrodes.

17. The method of claim 16, wherein the plurality of electrodes are mounted on the wound dressing as an array.

18. The method of claim 17, wherein each electrode of the plurality of electrodes is configured to transmit a different intensity level of electrical stimulation, and wherein adjusting the electrical stimulation comprises operating a different electrode.

19. The method of claim 18, further comprising identifying an electrode that caused the first stimulation response to satisfy the stimulation response threshold and determining a progress of wound healing based on a determined stimulation response to the electrode.

20. The method of claim 13, further comprising determining one or more areas of neuropathy or nerve growth in at least the portion of the wound based at least in part on the nerve response, wherein the indication of the wound status comprises a visual map of the one or more areas of neuropathy or nerve growth.

21. The method of claim 13, further comprising:
monitoring a patient movement; and
reducing intensity of or pausing the electrical stimulation responsive to the patient movement satisfying one or more movement thresholds.

* * * * *

UNITED STATES PATENT AND TRADEMARK OFFICE
CERTIFICATE OF CORRECTION

PATENT NO. : 11,839,464 B2
APPLICATION NO. : 16/651119
DATED : December 12, 2023
INVENTOR(S) : Varuni Rachindra Brownhill et al.

It is certified that error appears in the above-identified patent and that said Letters Patent is hereby corrected as shown below:

In the Specification

Column 10, Line 67, delete "bather." and insert -- barrier. --.

Column 16, Line 23, delete "mmHg" and insert -- mmHg. --.

Column 16, Line 35, delete "mmHg" and insert -- mmHg. --.

Column 16, Line 37, delete "mmHg" and insert -- mmHg. --.

Column 23, Line 10, delete "bather)" and insert -- barrier) --.

Column 25, Line 8 (approx.), delete "mmHg" and insert -- mmHg. --.

Column 43, Line 22, delete "FIG. 31" and insert -- FIG. 3I --.

Column 47, Line 49, delete "FIG. 31" and insert -- FIG. 3I --.

Column 50, Line 14, delete "FIG. 31" and insert -- FIG. 3I --.

Signed and Sealed this
Thirtieth Day of January, 2024

Katherine Kelly Vidal
*Director of the United States Patent and Trademark Office*